(12) United States Patent
Willson et al.

(10) Patent No.: US 7,220,828 B2
(45) Date of Patent: May 22, 2007

(54) HAEMOPOIETIN RECEPTOR AND GENETIC SEQUENCE ENCODING SAME

(75) Inventors: Tracy Willson, North Balwyn (AU); Nicos A. Nicola, Mont Albert (AU); Douglas J. Hilton, Warrandyte (AU); Jian-Guo Zhang, North Melbourne (AU); Alison Farley, Port Fairy (AU); Warren Alexander, Moonee Ponds (AU); Steven Rakar, Avondale Heights (AU); Yasufumi Kikuchi, Shizuoka (JP); Tetsuo Kojima, Shizuoka (JP); Masatsugu Maeda, Ibraki (JP); Louis Fabri, Diamond Creek (AU); Andrew Nash, Kew (AU)

(73) Assignee: Zenyth Operations Pty Ltd, Richmond, Victoria (AU)

( * ) Notice: Subject to any disclaimer, the term of this patent is extended or adjusted under 35 U.S.C. 154(b) by 0 days.

(21) Appl. No.: 09/037,657

(22) Filed: Mar. 10, 1998

(65) Prior Publication Data

US 2002/0045741 A1 Apr. 18, 2002

Related U.S. Application Data

(63) Continuation-in-part of application No. 08/928,720, filed on Sep. 11, 1997, now abandoned.

(30) Foreign Application Priority Data

| Oct. 23, 1995 | (AU) | ................................. PN6135 |
| Dec. 22, 1995 | (AU) | ................................. PN7276 |
| Sep. 9, 1996 | (AU) | ................................. PO2208 |

(51) Int. Cl.
*C07K 14/715* (2006.01)
*C12N 15/09* (2006.01)
*A61K 38/00* (2006.01)

(52) U.S. Cl. .................... 530/350; 435/69.1; 514/2; 514/8; 514/12; 536/23.5

(58) Field of Classification Search ................ 530/350, 530/351; 514/2, 8, 12; 536/23.5
See application file for complete search history.

(56) References Cited

FOREIGN PATENT DOCUMENTS

| EP | 138133 A | * | 4/1985 |
| WO | WO9008822 A | * | 8/1990 |

OTHER PUBLICATIONS

George et al. Macromolecular Sequencing and Synthesis, Alan R.Liss, Inc; New York, Chapter 12, pp. 127-149, 1988.*

Marra et al. (Accession No. W66776), The WashU-HHMI Mouse EST Project, Jun. 1996.*

Baumann, et al. (Oct. 25, 1991) "Interleukin—11 Regulates the Hepatic Expression of the Same Plasma Protein Genes as Interleukin—6", *The Journal of Biological Chemistry* 266 (30) :20424-20427.

Bazan (Sep. 1990) "Structural Design and Molecular Evolution of a Cytokine Receptor Superfamily", *Proc. Natl. Acad. Sci. USA* 87:6934-6938.

Burstein,. et al. (1992) "Leukemia Inhibitory Factor and Interleukin-11 Promote Maturation of Murine and Human Megakaryocytes In Vitro", *Journal of Cellular Physiology* 153:305-312.

Cwirla, et al. (Jun. 13, 1997) "Peptide Agonist of the Thrombopoietin Receptor as Potent as the Natural Cytokine", *Science* 276:1696-1699.

Davis, et al. (Dec. 27, 1996) "Isolation of Angiopoietin-1, a Ligand for the TIE2 Receptor, by Secretion-Trap Expression Cloning", *Cell* 87:1161-1169.

De Vos, et al. (Jan. 17, 1992) "Human Growth Hormone and Extracellular Domain of its Receptor: Crystal Structure of the Complex", *Science* 255:306-312.

Du, et al. (Apr. 15, 1994) "Interleukin-11: A Multifunctional Growth Factor Derived From the Hematopoietic Microenvironment", *Blood* 83(8):2023-2030.

Gearing, et al. (Jul. 12, 1991) "Homology of the p40 Subunit of Natural Killer Cell Stimulatory Factor (NKSF) with the Extracellular Domain of the Interleukin-6 Receptor", *Cell* 66:9-10.

Hangoc, et al. (Feb. 15, 1993) "In Vivo Effects of Recombinant Interleukin-11 on Myelopoiesis in Mice", *Blood* 81 (4):965-972.

Hirata, et al. (1994) "ADP Ribosyl Cyclase Activity of a Novel Bone Marrow Stromal Cell Surface Molecule", *FEBS Letters* 356:244-248.

Kawashima, et al. (1991) "Molecular Cloning of cDNA Encoding Adipogenesis Inhibitory Factor and Identity with Interleukin-11", *FEBS Letters* 283(2):199-202.

(Continued)

Primary Examiner—Eileen B. O'Hara
Assistant Examiner—Fozia Hamud
(74) Attorney, Agent, or Firm—Scully, Scott, Murphy & Presser, P.C.

(57) ABSTRACT

The present invention relates generally to a novel haemopoietin receptor or derivatives thereof and to genetic sequences encoding same. Interaction between the novel receptor of the present invention and a cytokine ligand facilitates proliferation, differentiation and survival of a wide variety of cells. The novel receptor and its derivatives and the genetic sequences encoding same of the present invention are useful in the development of a wide range of agonists, antagonists, therapeutics and diagnostic reagents based on ligand interaction with its receptor.

7 Claims, 53 Drawing Sheets

OTHER PUBLICATIONS

Keller, et al. (Sep. 1, 1993) "Interleukin-11 Inhibits Adipogenesis and Stimulates Myelopoiesis in Human Long-Term Marrow Cultures", *Blood* 82(5):1428-1435.

Layton, et al. (Sep. 1992) "A Major Binding Protein for Leukemia Inhibitory Factor in Normal Mouse Serum: Identification as a Soluble Form of a Cellular Receptor", *Proc. Natl. Acad. Sci. USA* 89:8616-8620.

Livnah, et al. (Jul. 26, 1996) "Functional Mimicry of a Protein Hormone by a Peptide Agonist: The EPO Receptor Complex at 2.8 Å", *Science* 273: 464-471.

Merberg, et al. (1992) "Sequence Similarity Between NKSF and the IL-6/G-CSF Family", *Immunology Today* 13(2):77-78.

Mizushima, et al. (1990) "pEF-BOS, a Powerful Mammalian Expression Vector", *Nucl. Acids Research* 18(17):5322.

Musashi, et al. (Sep. 15, 1991) "Synergistic Interactions Between Interleukin-11 and Interleukin-4 in Support of Proliferation of Primitive Hematopoietic Progenitors of Mice", *Blood* 78(6):1448-1451.

Paul, et al. (Oct. 1990) "Molecular Cloning of a cDNA Encoding Interleukin 11, a Stromal Cell-Derived Lymphopoietic and Hematopoietic Cytokine", *Proc. Natl. Acad. Sci. USA* 87:7512-7516.

Yang, et al. (1992) "Interleukin-11 and its Receptor", *Biofactors* 4(1):15-21.

Yonemura, et al. (1992) "Synergistic Effects of Interleukin 3 and Interleukin 11 on Murine Megakaryopoiesis in Serum-Free Culture", *Exp. Hematol.* 20:1011-1016.

Schibler, et al. (Aug. 15, 1992) "Effect of Interleukin-11 on Cycling Status and Clonogenic Maturation of Fetal and Adult Hematopoietic Progenitors", *Blood* 80(4):900-903.

Suri, et al. (Dec. 27, 1996) "Requisite Role of Angiopoietin-1, a Ligand for the TIE2 Receptor, During Embryonic Angiogenesis", *Cell* 87:1171-1180.

Toga, et al. (Aug. 11, 1989) "Interleukin-6 Triggers the Association of its Receptor With a Possible Signal Transducer, gp130", *Cell* 58:573-581.

Teramura, et al. (Jan. 15, 1992) "Interleukin-11 Enhances Human Megakaryocytopoiesis *In Vitro*", *Blood* 79(2):327-331.

Tsuji, et al. (Jun. 1, 1992) "Enhancement of Murine Hematopoiesis by Synergistic Interactions Between Steel Factor (Ligand for c-kit), Interleukin-11, and Other Early Acting Factors in Culture", *Blood* 79(11):2855-2860.

Wrighton, et al. (Jul. 26, 1996) "Small Peptides as Potent Mimetics of the Protein Hormone Erythropoietin", *Science* 273:458-463.

* cited by examiner

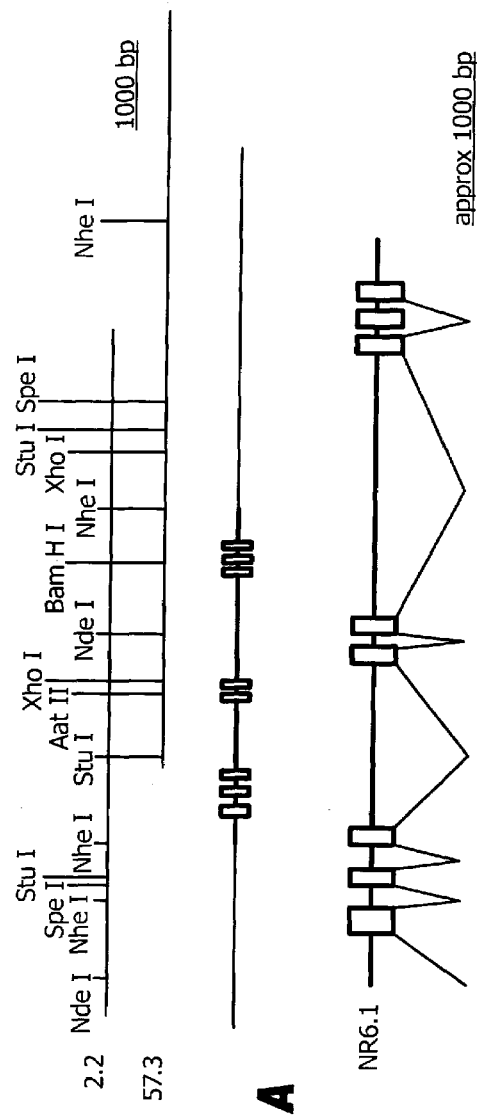
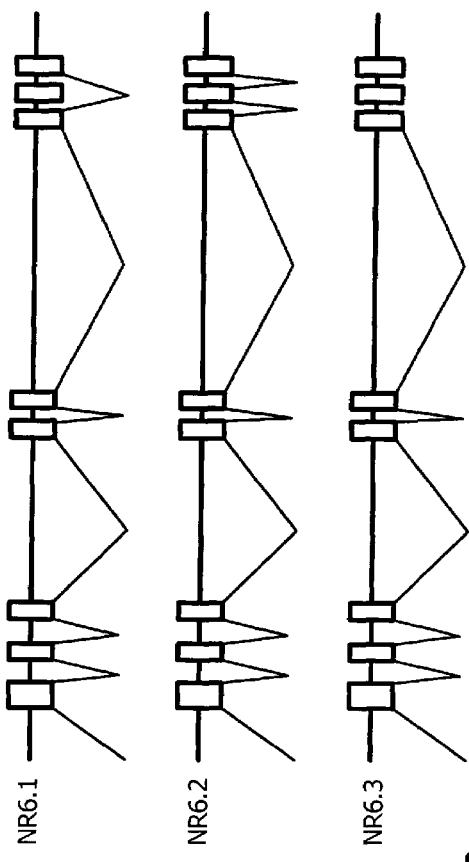
Fig. 1A
Fig. 1B

```
g1                 cccagaactcttggacgctgaggcaggaggattccca
g38       agtttcaagacagtgtgtttctaggtaatgagaccctgtcaagaa
g83       aagaaaagaaataaagagacaagaaaatgtttataggctgtgaga
g128      cagcttggtgggtaaggggcacttgcctccaatcaagatgacctc
g173      agccccatccctaggaatccatggtagaaggagaaagcaaactcg
g218      cagctgctgacctccatacatgtgctccaatgtgcacacacacag
g263      ggagacataatcaattaataggatgtatttgcttagatttgagta
g308      ggcatttatgactgatgttttaaaattttatttgattttatgaa
g353      aatatacctgtttgtatttggtttggtttggtttgagttttgttt
g398      atttgagacagggcttctctgtgtagtcctggctgtccttggaac
g443      tcactctgtagaccaggctggccttgaactcagaaatccgcctgc
g488      ttgtgcttcccaagtgcttagattaaaggtgtgcactgccattca
g533      gcaaaattgcatactttaaccccagtatttgggaggcagaggcag
g578      actaatgtgtgaattccaggctagccaaggatacagagtgagacc
g623      ctattcttaccctcccccccaaaacccaaaatgtatttgtgc
g668      ttgtgtatgtacatgtgtgttgcagcacgtaaatgtccaaggaca
g713      acttgtagaagttctctccgttcacagtctaagtcctgaattcaa
g758      actaaggtcctcaggcttagccacagtcttctttatgtactgagc
g803      catttcactggccctggattgactgatgaattaattttgagata
g848      aggtctcttgtagctctagctaggctcaaactatgaactcccaag
g893      gtcatcttgagctgctggtactcttgcttccaccccaagtggtgg
g938      aatgatactcaggcagcacttctctggggaaggggctggccttgg
g983      ccttgatttgttgcctcagcttcaatgagtgcttgggtctcgtt
g1028     gtttcttttctttatctgtgaaatgggtgaacacctgttcaagac
g1073     ttcctgactcttgaaacatccaggcagggtgagggacttgaagtg
```

```
A- - · - · - · - · - · - · - · - · - · - · - A
g1118   ggctcatcccatgcctaacaaagtgtcgtctttgaccccagacac
                             D  P  T  L  L  I  G  S  S
g1163   agctgtaatcagcccccagGACCCCACCCTTCTCATCGGCTCCTC L  Q  A  T  C  S  I  H  G  D  T  P  G  A  T
g1208   CCTGCAAGCTACCTGCTCTATACATGGAGACACACCTGGGGCCAC A  E  G  L  Y  W  T  F  N  G  R  R  L  P  S
g1253   CGCTGAGGGGCTCTACTGGACCTTCAATGGTCGCCGCCTGCCCTC E  L  S  R  L  L  N  T  S  T  L  A  L  A  L
g1298   TGAGCTGTCCCGCCTCCTTAACACCTCCACCCTGGCCCTGGCCCT A  N  L  N  G  S  R  Q  Q  S  G  D  N  L  V
g1343   GGCTAACCTTAATGGGTCCAGGCAGCAGTCAGGAGACAATCTGGT C  H  A  R  D  G  S  I  L  A  G  S  C  L  Y
g1388   GTGTCACGCCCGAGACGGCAGCATTCTGGCTGGCTCCTGCCTCTA
         V  G
g1433   TGTTGGCTgtaagtggggccccagacactcagagatagatggggg g1478   ttggcaatgacagatttagagcctgggtcttctgtcctggggcag
g1523   agccatgggctctcacttgcatgcaggcatggtcatacccagcac
g1568   aggcattgcaactctagggacagctgtggctgcactgtcccctgt L
g1613   gtacccacagctttagaaaagctgtcatgttttccttgtagTGC
B- · - · - · - · - · - · - · - · - · - · - B
```

Fig. 2(2)

```
B-  ·  -  ·  -  -  -  -  -  -  -  -  -  ·  -  -  -  ·  B g1658      P   P   E   K   P   F   N   I   S   C   W   S   R   N   M
           CCCCTGAGAAGCCCTTTAACATCAGCTGCTGGTCCCGGAACATGA g1703      K   D   L   T   C   R   W   T   P   G   A   H   G   E   T
           AGGATCTCACGTGCCGCTGGACACCGGGTGCACACGGGGAGACAT g1748      F   L   H   T   N   Y   S   L   K   Y   K   L   R
g1793      TCTTACATACCAACTACTCCCTCAAGTACAAGCTGAGgttggtac
g1838      ccagccaagccttgctgtgtgacttctggcaatacttaccttctc
           tgatcaaatatgttcctgtttatgaactcaaaagggactctcgca W   Y   G   Q   D   N   T   C   E   E   Y   H
g1883      cctccacagGTGGTACGGTCAGGATAACACATGTGAGGAGTACCA T   V   G   P   H   S   C   H   I   P   K   D   L   A   L
g1928      CACTGTGGGCCCTCACTCATGCCATATCCCCAAGGACCTGGCCCT F   T   P   Y   E   I   W   V   E   A   T   N   R   L   G
g1973      CTTCACTCCCTATGAGATCTGGGTGGAAGCCACCAATCGCCTAGG S   A   R   S   D   V   L   T   L   D   V   L   D   V
g2018      CTCAGCAAGATCTGATGTCCTCACACTGGATGTCCTGGACGTGGg g2063      tgagcccccagtgtccacctgtgttctgccctagaccttataggg
g2108      cgcctcccccatcccccagactttttggttcttctagaggtc
g2153      ttagccacagccacggtggttgcaggacagtggttgttcataact
g2198      taatgcaaagactttcccccaagacagtcaagatttttcccctcc

```
g2243   ccaccccccaacacacacatacacacacactctgcagagaacacct
g2288   ggcctgaccaccctccctctctacagcccaggtgttcagaaggga
g2333   gtcctaggggactgagaggaggcgcccaggtctgaaggcgcccca
g2378   ggaagccgaggccttgagctggggggggggcgagggttggaggc
g2423   acgaactggatgatccctgagcacaactgggcctaatctaattag
g2468   ggtgttcccagcccaaagcagcctgggccatttaaccctttcaagt
g2513   gcctcactgaagactcaggggagagatcagcttgtactctctcca
g2558   tggtccccaggagggttcctgggtgcccctggctcattcccaca
g2603   tccagaggttttgtgtcttcctggcatctaaccctcagttgtgct
g2648   ctgtggctggcacagctgccccgtggaggctcttggtaatgtaca
g2693   aggcatcagaggtggacatgggatggggatacatagggatggagc
g2738   caaatagcacctcaaggtggggtgatatacaataaagcttgtcac
g2783   cctgacgctcagaaagcctactcatgatgatcacaattgttgaca
g2828   tcactctgggacatgtagtgagaccctagctcaaaacacagacag
g2873   tagctttaagagtcagcttgtgacttaatactggaactcagggcc
g2918   taataggtgctgggtgatgctcgcctcactccctgtttagtgaga
g2963   tctctgcgctaatctccaccccagctgggtgggctgctctgtccc
g3008   cttgagggcaggaatgtgtgtcttccatcagagataggacccgtg
g3053   gtagcagcaactgctgctggctgtttctggaatattaaatgacag
g3098   taatctatcaggcctgggtgagtagctaacaggggtgggggcgtg
g3143   gtctggaaaacgcagatagggtcataggagccactgcagcctaga
g3188   ttacaccactgggtgttctgtcactaggccattctcaccaagcag
g3233   tcctcagaactgggagcactgttgccagcatttaatgccagcatt
g3278   taatgccagcattaggggaggcagaggcagaaggatctctctgag
g3323   ttcaaggccatcctgaatttacataaagagctccaggccagccag
g3368   ggtgcgcagtaaaaccttgtctcaaaaaacaaagcatctttagtg
```

```
D- · - - - - - - - - - - - · - - · D
                            V  T  T  D  P  P  P  D
g3413    accaggcttgctccaccccagTGACCACGGACCCCCCACCCGAC V  H  V  S  R  V  G  G  L  E  D  Q  L  S  V
g3458    GTGCACGTGAGCCGCGTTGGGGGCCTGGAGGACCAGCTGAGTGTg R  W  V  S  P  P  A  L  K  D  F  L  F  Q  A
g3503    CGCTGGGTCTCACCACCAGCTCTCAAGGATTTCCTCTTCCAAGCC K  Y  Q  I  R  Y  R  V  E  D  S  V  D  W  K
g3548    AAGTACCAGATCCGCTACCGCGTGGAGGACAGCGTGGACTGGAAG
g3593    gtgcccgtcccgccccggacccgcccctgaccccgcccccgcat V  V  D  D  V  S  N
g3638    ctgactcctccctcaccgtgcagGTGGTCGATGACGTCAGCAACC Q  T  S  C  R  L  A  G  L  K  P  G  T  V  Y
g3683    AGACCTCCTGCCGTCTCGCGGGCCTGAAGCCCGGCACCGTTTACT F  V  Q  V  R  C  N  P  F  G  I  Y  G  S  K
g3728    TCGTCCAAGTGCGTTGTAACCCATTCGGGATCTATGGGTCGAAAA K  A  G  I  W  S  E  W  S  H  P  T  A  A  S
g3773    AGGCGGGAATCTGGAGCGAGTGGAGCCACCCCACCGCTGCCTCCA T  P  R  S
g3818    CCCCTCGAAGTGgtgagcacctctccagggctggctggcccatgg
g3863    aatccccaatccatcctgttccttcccccccaccctttttttgag

```
g3908    acagcgtcttcaggtagcgcatgctggccttaaattcagtatgta
g3953    gtcaaggatgacctcgagctcctggtcttttcgtctccacttaga
g3998    gacaatggccagtggccatcaccacctttgggagactagccatgg
g4043    agtctatttagcctgtcatttggtgacagatggagtacaacagtg
g4088    tgacctcttgtaagagaactgaagacaggctgttttaacccca
g4133    tatcctaggctctctagaggttaactttatataaaatagagacta
g4178    ttacagccagttatcacatggtcccacagaaccttttgtcacaca
g4223    acctatagaccacagtgcctgtgcctaccacataagggtctctac
g4268    tgctggcccaccctccaacccttaaaaggtaacctaggcagcct
g4313    taatatttgcaatcctcctacctcagcctcttgaatgctcagaaa
g4358    ccaggcattaacccaagttctcttctctgggtccctttcttaag
g4403    gtgggagggcctaaagatgacttcctttgtcctgaagactctccg
g4448    agcccatggatctgcactctctaatatgaaatatattgcataaaa
g4493    tgtctggcctcagtttccccacctgtcaggtttaggcagcacagt
g4538    cggtccaagacacttcattatttgcaggcagtataagaagaagct
g4583    cccatccccaccgcttcctccggtccctaagacagaatacttc
g4628    tacactgaaactgaactctcgcagacgcatatgctcactttaatg
g4673    atgatgaaataatggggaaactgaggctccgagagattcctggag
g4718    gaagagggtcaaaaccagctccaggaagctctccagcccccatcc
g4763    gggcctctccaggttctgggcttggcgggagtgaacacagctggg
g4808    aggggctggagcctgggagctttggcccttgctcgtgcccagcac
g4853    ctgcgattcttgcacgggagccagcaggcggctgcgtccgcccga
g4898    gagactgaagaagccgggggtagggttggagggaggtaagcaggg
g4943    gctgtggggccgaagcttgtgcagggcctgtcagcgagtcccc
g4988    agttttatttatggcgtgaggccgatgtccttatccgctggcctg
g5033    ctgggggatggctgcggctggggattggacccaagggctggcttc
```

```
g5078      ccactcagtcctccagcccactccatgtcacacccgtgcattctc
g5123      tgaggcttatcttgggaacccgcccttgttctgtgctgtctgtct
g5168      ctatttctgtcattcactttcccagagcctttttttatgctttt
g5213      aatataactacgttttaaaaattgcttttgtataatgtgtgtgcc
g5258      ttcgtgagcgtgcgtgccacaacacacacgtgaaggttagagaac
g5303      tttgttgagtaggctccttccaccatgtgggactagggctggcga
g5348      caagagcaattactgagtcatctcgccagcccctcacccctcact
g5393      tcccatcctgtttggatagtcataggtaatcgaaggtaaatcgct
g5438      ggctttaatttcgtagctatcctgcctcagcctaccaagtgctgt
g5483      gctaccacgtttgtgggaggggctctcctcccagtgtctgggggt
g5528      gacacagtcccaagatctctgctttctaggtctttgtcttagttt
g5573      gccccttgctttgtccgtgtccctagagtctccggccccacttatc
g5618      cattgactggtctttcctttaccgaatactcggttttacctccca
g5663      ctgatttgactccctcctttgcttgtctccatcgccgtggcattg
g5708      ccattcctctgggtgactctgggtccacacctgacacctttccca
g5753      actttccccagccgaagctggtctggtatgggaggccgccgtccc
g5798      gcgcgcgcctcctgctggccgcgccccaacactgccgctccattc
```

```
                   E  R  P  G  P  G  G  V  C  E  P  R
g5843      tctttagAGCGCCCGGGCCCGGGCGGCGGGGTGTGCGAGCCGCGG
```

```
           G  G  E  P  S  S  G  P  V  R  R  E  L  K  Q
g5888      GGCGGCGAGCCCAGCTCGGGCCCGGTGCGGCGCGAGCTCAAGCAG
           F  L  G  W  L  K  K  H  A  Y  C  S  N  L  S
g5933      TTCCTCGGCTGGCTCAAGAAGCACGCATACTGCTCGAACCTTAGT
```

F  R  L  Y  D  Q  W  R  A  W  M  Q  K  S  H
g5978   TTCCGCCTGTACGACCAGTGGCGTGCTTGGATGCAGAAGTCACAC

K  T  R  N  Q  V  G  K  L  G  E  A  C  V  G
g6023   AAGACCCGAAACCAGGTAGGAAAGTTGGGGGAGGCTTGCGTGGGG

G  K  G  A  E  E  E  R  D  P  G  E  Q  P  P
g6068   GGTAAAGGAGCAGAGGAAGAGAGAGACCCGGGTGAGCAGCCTCCA

Q  H  R  T  L  L  S  K  H  R  T  R  G  S  C
                                              D  E  G  I  L
g6113   CAACACCGCACTCTTCTTTCCAAGCACAGGACGAGGGGATCCTGC

P  R  A  D  G  V  R  R  E  V  R  G  S  G  *
         P  S  G  R  R  R  G  A  A  R
g6158   CCTCGGGCAGACGGGGTGCGGCGAGAGGTAAGGGGGTCTGGGTGA
g6203   GTGGGGCCTACAGCAGTCTAGATGAGGCCCTTTCCCCTCCTTCGG
g6248   TGTTGCTCAAAGGGATCTCTTAGTGCTCATTTCACCCACTGCAAA
g6293   GAGCCCCAGGTTTTACTGCATCATCAAGTTGCTGAAGGGTCCAGG

V  L  P  A  K  L
                                        G  P  A  G  *
g6338   CTTAATGTGGCCTCTTTTCTGCCCTCAGGTCCTGCCGGCTAAACT

*
g6383   CTAAGGATAGGCCATCCTCCTGCTGGGTCAGACCTGGAGGCTCAC

```
g6428   CTGAATTGGAGCCCCTCTGTACCATCTGGGCAACAAAGAAACCTA
g6473   CCAGAGGCTGGGCACAATGAGCTCCCACAACCACAGCTTTGGTCC
g6518   ACATGATGGTCACACTTGGATATACCCCAGTGTGGGTAGGGTTGG
g6563   GGTATTGCAGGGCCTCCCAAGAGTCTCTTTAAATAAATAAAGGAG
g6608   TTGTTCAGGTcccgatggccagtgtgtttggggcctatgtgctgg
g6653   ggtgggggga
```

Fig. 2(9)

```
GCGGCCGCTG CAGTGATTAC TCACCGCGTG GCGCACCCCA CCCGCGGGCC GCTGAGTGGA    60

TTTTTCCGTG GGGGATGTG AAGAAGTTTA GGGAGAACTC TTCTGCACCG ATGGAACTA    120

GGAATGCAGG GTTCGGTCCC GTTCCCCAAA GGACACACCT CTCCCCATAA GCCCACTCAT    180

AAGGGCTCCC TGCACGCGCT CCGGGACATC CCCATATCCA ATACCCGCAG ATATGATAGT    240

TGAGAAGGGA CCAGAGGCCG GAGACTCCCT CCCTGCCTTC TGGCTTTCCC CCCCCCCTGC    300

ACGAAACGAG ACTACAGCGA TGGGAGAGGT GGCATGAAGG CTTAGGGTGG GGATCGGTAG    360

GACCCATGCA CCCAGAGAAA GGGACTGGTG GCAACTTTCA AACTCTCTGG GGAAGGAAGA    420

AGGGCTGAAA GAGGATGAAC GGGCTCAGGT ACTGCTCAAT GTGTGTGTGG CGGACCAAAG    480
```

*Fig. 3(1)*

```
TGGGTATGGG  GGCCCCGTAA  GAGGGGGCGGG  GAAGGTGGAT  AGGAAGGATC  CCGGTAGACT   540

GGAGGGGATC  CTGGAAAAGC  ACCAGGGCTG  CGAGCTAGGA  ACCCATTCGG  AGTTAAGGGT   600

ACAGGATCCC  AGATGAGGGG  GTGGGAAGCC  TGGGACGGGC  GGGACCAGAG  AGGGAGGTCC   660

CACGGGCTGG  TGGGGAAAGA  GTGGGGGGCT  TCGCGCAGGA  GGATGGGACG  TTCAGGAGTG   720

GTAACTGGGC  GGAGGCCCGC  CGGGCGGGGC  GCGGGTGCC   CGCGGGCCGT  GGGAAGGCCG   780

GTGCGGGGCC  CACGATCAAC  CCCCCCCCAG  GGGCGGGGCC  GGGCCGGGGG  CGGGGCCGGG   840

CGGGGCGAGC  GGCGCATTAG  CGCCTTGTCA  ATTTCGGCTG  CTCAGACTTG  CTCCGGCCTT   900

CGCTGTCCGC  GCCCAGTGAC  GCGCGTGAGG  ACCCGAGCCC  CAATCTGCAC  CCCGCAGACT   960
```

*Fig. 3(2)*

```
CGCCCCCGCC CCATACCGGC GTTGCAGTCA CCGCCCGTTG CGGCCACCC  CCATGCCCGC   1020
GGGTCGCCCG GGCCCCGTCG CCCAATCCGC GCGGGGCCG  CCGCGGGCCGC TGTCCTCGCT   1080
GTGGTCGCCT CTGTTGCTCT GTGTCCTCGG GGTGCCTCGG GGCGGATCGG GAGCCCGTGA   1140
GTACCGTGCG CCCTGCTCCC CACCTCCCCA GGGAAGCCGG GATCCGGCGC CCCGGGGGT    1200
AGTCGCGGGG GATGGAAGAA GGGGCGCGAG CGCCACCTGG ACGTCCCGGG AACAAAGGAA   1260
GGCGGCCCTC GGGGCGCCCT CACCTGTGGG GCTCATGGCA CCACCACCCA GCCTCCCAAG   1320
```

*Fig. 3(3)*

```
AGTACCCCGT TATACATCAG AGGCCTCTTA TCTGTATCCC CTTTGCCAGG CTGTCTGCCC    1380

AGGCTCAGTT TGAAGGACAT CGCAGTGTCC TGGGACCCCC CTCCTTCAGG GTGCTGGGAC    1440

GCTTCGGGGC GCACGCCTGT GTCTTGGATA TCAGAGCGGA AGGGAAGCCT CCCTGGCCGG    1500

GGGCGCACGC TTGGGTGCGT TGGGTTGGGT GCTGGCGCAA AGTGGGGTCC CCTCCCCCAT    1560

GAAGTGATGA TCCCCGGGGG GAGGGTGGGG CGTTATCGTG AGCCCTCCTG TCCGCCTGGC    1620

ATGCGGCCCG GCGTCCCCTCG GGACTTGCCT CTCCGTGGGG TCGGCGCCGC CCCCTCCCCC    1680

CTATAGCAGA CTCCATGCTT TGGTATCCTC GAAGTCCTCT CCACTGGTGG GGCTCACAAC    1740

CGGTCTCCATT CAGGCTGCGC TGGGTTGAGA GCCTCTAGCG ACTGAAATTT CGGTGAGGAG    1800
```

Fig. 3(4)

| | | | | |
|---|---|---|---|---|
| CGAGAGCAAG | CGTGTCCGGG | CACCGGCGAGC | CCAGACTTCA | TTGTCTAAGG | GGCACCCAGT | 1860 |
| GGGGGTCAGC | TGCCGAGAGA | ATCCCACTGT | CCCAGGAGGA | ACTCCTGGCC | TTGAGCCCCC | 1920 |
| ATCACCCCAAC | GCACACATCC | CCGCCAGGAT | GCGGTCTCCA | CATCCAGACC | CTCTCTGGGA | 1980 |
| CACACCCAAA | GACACACACA | AGAGCCCCAC | TGGCTTATGT | CCCGTCACCC | TGCCCTCCGA | 2040 |
| CGCGCGGCTGC | AGCCCAGATG | CGTATTCGCA | CACCATCGCG | GCGCTCGCAT | TCCATCCTCT | 2100 |
| ACACACACAC | ACACACACAC | ACACACACAC | ACACACAGAC | ACACACACAC | ACGCACACAC | 2160 |
| ACACGCACGC | ACACACACGC | ACGCCCGCAC | TCGTGGTCCC | ACATTTATTT | CACAGGGGAG | 2220 |
| GCAACACCGG | GGTACGCATA | TGGTTGAGTG | CACTGGAGAT | CTTTCCCCAC | CACTCTCAGG | 2280 |

Fig. 3(5)

```
ACCCCATCCG GAGACACAGG CCACACCGCA GGGGCACCAC GCTGCGCTGC TGCTCTGGGC    2340

TAGTAGTCTT GTGCAGTTTG TCCGCGGTGT CTGTGGACGC CCTCCCGCTC TTGTCAGGGG    2400

ACAGGAACCT ACACTCCTGC TTGCCCAAGG CGGCTGGGCA GGTGATGTGG TGACACCCG     2460

GACCTTTCCG GGGAGTTGGT GTTGCTGCCA AGCCTGGGTA GTTTTTGAAT GCCACCAATA    2520

GCGCTAAGCT TTGTTTCCGG GCGGGCTGCA GAGCAACAGG CGAAGGTGGC GGAGTGGGGG    2580

TGGCGCGTGT GTTTTTTCTT TTAAGGGGGA GAGAAATTAA ATAAGAGGTT CTCACACCTC    2640

TGCAATCTGT TTGTACTTAC CGTGTGTCTT AACACCTGAC CAGCCAGCCG GTGGGTCGTA    2700

AAAGTGTATG CAGGTACCAG CGGGACAGGA GATGGGGGCC CCTGGGGTAT GGCTGGGATG    2760
```

Fig. 3(6)

```
GAGGCCACCT TCCCGTTGGC CTTTCAGGGA ATCTCACACT TTTCCCTTTT AAAACACATG   2820

GTGTTCTTTT TAATAACGGC AGCAACTCCG CATTGGGAAA GGGGGAAATA AGCTTGTATA   2880

GGCCCCGGCT TTGTGGAAAG GAGGGGAAGA GGGAAGAAAA AAGGAGGGGT GTCTCCTCCA   2940

GGCTTAGGGG GCTGTCAGCT GCTGCTCTGT CTAGCTTGGC ATGTGTGTGC CCCAGTCCCC   3000

AGTGGCTTTG GCCCATTGTT TGTGGAAGCC AAGAGGGAGA CTGGAGTCCT CTATCTCTGG   3060

TACTCCAGAG TCAGGCTTCT CAGTCCGAGC CCAGAGAACG TCTTCCCTGT TTTATGGAGG   3120

GAATCAGGGA AGGGGGTGCC AGTGGACTA CGTTCTGCTG AGGACTGTAC CAGTCGCTCG   3180

AAGGAGAAAG CTTGGGCTTG CCCCCCCTCCC CCCTCAAGCC ACGAAGGGCA GCTGCTAGGC   3240
```

Fig. 3(7)

```
TAGTGTGGTA AAAGGGCATT ACTCCCCAGC CAGGACCCCC CAGAGAGTCC CCTTCCTGGC    3300

CAGACAAATG CTGGGGAGGG ACAGAGGGGT GTGATCATTG CCCAGGAGTG CAGACAGTGG    3360

GGTCCCGGGT CGGGCAGTGC CTCCCACCCT GCTGAGGGGG GCGCCCAGGC AGGAAGCGGT    3420

GGGTGGGCCG GGGTAGAGAC GCTGGCACGT CCCAGTTCAT GCCGAAGGAA TTCTGAATTA    3480

GCGGGGGGCT GGCTGCCTGG GACCTCCGGG GCGGCCCCCT GGCCCCCGCC GCTCCGTCTG    3540

GCCTGCTCCT CCTGCTCCTT CGCACGGACG CTGAGACCTC CGCTGAGCCC TGGGACAAGC    3600

CCCAAATGCA ACTGCGATTG CAGGCTTCGC AAGACCCGCC TCCTCCCAAG GCCAAATTTG    3660

CCTGGGAGAA GTCATTCAGG GCCCAGACTA GAACCATGTT GGTGCCACCT CATCCATCTG    3720
```

*Fig. 3(8)*

```
GGGCATGAAGG GACCGTCCAG GGCTGCAGTT TAGCTTCTTA ATAGGAACCT GGGGGTGGGT     3780
GCAGCCTCTG TTCTCCGAGC CTCTTTGGAA ATCGGTTTTG TTTTGTTTT TGTTTTTCC        3840
AATACTCTTT TCCTCTCATC CCATCCCGGG ACTGTTTTCC TCCCTAAGGG TTGAGAGCCC      3900
TGCAGTCTTC CCTAACCTTT TCTTTGCTTC TACCCCAGGG CCTTTGCACA TGGAGTCCCA      3960
CCTCTCCCCT TGCCCAACTG GGGCTCCAGC CTTACTGCAT TTGGCTCTTG GTAACTGTCC      4020
CAGGGCCTCT CTGACACACA GGGTTGTAGC CCCAGCTCCC TCTCTTCTCC TCCCCCCTTT      4080
CTCTTTTGCT TCTGAGACTT AATTTTTTC TTTTCTTTT TGGCTTTTTG AGACAGGGTT        4140
TCTCTGTACA GCCCTGGCTG CCCTGGCACT CATTCTGTAG ACCAGGCTAG CCTCAAACTC      4200
```

*Fig. 3(9)*

```
ACAAACCTAC CTGCCTCTGC CTTTCCAGTG CTGGCACTAA AGATGTGGGC CACCACAACT    4260

AGTAGTTAAG TGTTTGCTG TGTCTTTATT CCTATAGTGA CCTCAGTTCC TGGCATATTG     4320

TAGGCGATGG ATGGATGAAT GGATGGATGG ATGGAGCAAG GAATGGAGTT AGGTTCCCAG    4380

CTTGAATCGT CCTGAGTGAA AAAAGAGACC TCAGAGAACT GAATGGAGTT AGGTTCCCAG    4440

GGCAGCCTGG CCTGCTGGTC TCATGGGAGC TCCCTGTGAA ACTTCCCCCA CACCTCCCAC    4500

CACCCTGCCA TCCTGTGTGG CTGACAAGAA AGGCCAATGG CCAGATGGGG ACACAGACTC    4560

AGGGAAGCTT GGAATATGTT CCCCTCCCTCA TATCCTAGGC CTTGTTGTCC CCCTGAGGGC   4620

CCAGCCTATG AGTAGGGCAG CTGTGGGCTG CCCTAAGGTT GGGTAGGCAA GAAGGGGGTG    4680
```

*Fig. 3(10)*

```
GTCCCTCAGG GTGGGTCACA GGATTGAGGT CATTTCCAAA GTGGCCATCA CAGTGGCCCT    4740

AGGAAATGAT TGTGGAGAGT CAGAACTCCT GTTGGGAGTT GTAGAGGGCC TTGCATGTGG    4800

GCTTCTGTGG CTGTCCCTTC TCTTGTGGTC CTTTGCACAG TCCCCTCGTG TGTGCTGGGA    4860

TGTGAGGAGG GCACGGGGAA AATGAAGGCT CAGCCCCTCA GCTTGCCCTT CACGGTTCAC    4920

CCAACAGGGC TCACCTCTCC TCTGGACAGG CTCTCACTGT ATGCACAGAT TGGCCTCACA    4980

TTTGATTCCC TTCCTTTGGT CTCCCTGGGAT GACAAACATT TACCAGGGTA GGATTTTACA    5040

TTTTAGATAT GTCCATTCTC CAGAAACACA CTTGTGAGGT TAGGGTATCA GTGAAAGGAC    5100

ACCACCAGGA CAGACAAAGA ATTGGAGAGG AAGGAAATTG GTAAGCCAGG CCATGCTTGA    5160
```

*Fig. 3(11)*

| | | | |
|---|---|---|---|
| TGGCTTATGT GTAATCCCAG | AACTCTGGAC GCTGAGGCAG | GAGGATTCCA AGTTTCAAGA | 5220 |
| CAGTGTGTTC TAGGTAATGA | GACCCTGTCA AGAAAAGAAA | AGAAATAAAG AGACAAGAAA | 5280 |
| ATGTTTATAG GCTGTGAGAC | AGCTTGGGTGG GTAAGGGGCA | CTTGCCTCCA ATCAAGATGA | 5340 |
| CCTCAGCCCC ATCCCTAGGA | ATCCATGGTA GAAGGAGAAA | GCAAACTCCA GCTGCTGACC | 5400 |
| TCCATACATG TGCTCCAATG | TGCACACACA CAGGGAGACA | TAATCAATTA ATAGGATGTA | 5460 |
| TTTGCTTAGA TTTGAGTAGG | CATTTATGAC TGATGTTTTA | AAATTTTTAT TTGATTTTAT | 5520 |
| GAAAATATAC CTGTTTGTAT | TTGGTTTGGT TTGGTTTGAG | TTTTGTTTAT TTGAGACAGG | 5580 |
| GCTTCCTCTGT GTAGTCCTGG | CTGTCCTTGG AACTCACTCT | GTAGACCAGG CTGGCCTTGA | 5640 |

Fig. 3(12)

```
ACTCAGAAAT CCGCCTGCTT GTGCTTCCCA AGTGCTTAGA TTAAAGGTGT GCACTGCCAT    5700

TCAGCAAAAT TGCATACTTT AACCCCAGTA TTTGGGAGGC AGAGGCAGAC TAATGTGTGA    5760

ATTCCAGGCT AGCCAAGGAT ACAGAGTGAG ACCCTATTCT TACCCTCCCC CCCCAAAACC    5820

CCAAAATGTA TTTTGTGCTT GTGTATGTAC ATGTGTGTTG CAGCACGTAA ATGTCCAAGG    5880

ACAACTTGTA GAAGTTCTCT CCGTTCACAG TCTAAGTCCT GAATTCAAAC TAAGGTCCTC    5940

AGGCTTAGCC ACAGTCTTCT TTATGTACTG AGCCATTTCA CTGGCCCTGG ATTGACTGAT    6000

GAATTAATTT TTGAGATAAG GTCTCTTGTA GCTCTAGCTA GGCTCAAACT ATGAACTCCC    6060

AAGGTCATCT TGAGCTGCTG GTACTCTTGC TTCCACCCCA AGTGGTGGAA TGATACTCAG    6120
```

Fig. 3(13)

```
GCAGCACTTC TCTGGGGAAG GGGCTGGCCT TGGCCTTGAT TTTGTTGCCT CAGCTTCAAT    6180

GAGTGCTTGG GTCTCGTTGT TTCTTTTCTT TATCTGTGAA ATGGGTGAAC ACCTGTTCAA    6240

GACTTCCTGA CTCTTGAAAC ATCCAGGCAG GGTGAGGGAC TTGAAGTGGG CTCATCCCAT    6300

GCCTAACAAA GTGTCGTCTT TGACCCCAGA CACAGCTGTA ATCAGCCCCC AGGACCCCAC    6360

CCTTCTCATC GGCTCCTCCC TGCAAGCTAC CTGCTCTATA CATGGAGACA CACCTGGGGC    6420

CACCGCTGAG GGGCTCTACT GGACCTTCAA TGGTCGCCGC CTGCCCTCTG AGCTGTCCCG    6480

CCTCCCTTAAC ACCTCCACCC TGGCCCTGGC CCTGGCTAAC CTTAATGGGT CCAGGCAGCA    6540

GTCAGGAGAC AATCTGGTGT GTCACGCCCG AGACGGCAGC ATTCTGGCTG GCTCCTGCCT    6600
```

Fig. 3(14)

```
CTATGTTGGC TGTAAGTGGG GCCCCAGACA CTCAGAGATA GATGGGGGTT GGCAATGACA    6660

GATTTAGAGC CTGGGTCTTC TGTCCTGGGG CAGAGCCATG GGCTCTCACT TGCATGCAGG    6720

CATGGTCATA CCCAGCACAG GCATTGCAAC TCTAGGGACA GCTGTGGCTG CACTGTCCCC    6780

TGTGTACCCC ACAGCTTTAG AAAAGCTGTC ATGTTTTCCT TGTAGTGCCC CCTGAGAAGC    6840

CCTTTAACAT CAGCTGCTGG TCCCGGAACA TGAAGGATCT CACGTGCCGC TGGACACCGG    6900

GTGCACACGG GGAGACATTC TTACATACCA ACTACTCCCT CAAGTACAAG CTGAGGTTGG    6960

TACCCAGCCA AGCCTTGCTG TGTGACTTCT GGCAATACTT ACCTTCTCTG ATCAAATATG    7020

TTCCTGTTTA TGAACTCAAA AGGGACTCTC GCACCTCCAC AGGTGGTACG GTCAGGATAA    7080
```

*Fig. 3(15)*

| | | | | |
|---|---|---|---|---|
| CACATGTGAG | GAGTACCACA | CTGTGGGCCC | TCACTCATGC | CATATCCCCA | AGGACCTGGC | 7140
| CCTCTTCACT | CCCTATGAGA | TCTGGGTGGA | AGCCACCAAT | CGCCTAGGCT | CAGCAAGATC | 7200
| TGATGTCCTC | ACACTGGATG | TCCTGGACGT | GGGTGAGCCC | CCAGTGTCCA | CCTGTGTTCT | 7260
| GCCCTAGACC | TTATAGGGCG | CCTCCCCCCC | ATCCCCCCAG | ACTTTTTGGT | TCTTCTAGAG | 7320
| GTCTTAGCCA | CAGCCACGGT | GGTTGCAGGA | CAGTGGTTGT | TCATAACTTA | ATGCAAAGAC | 7380
| TTTCCCCCAA | GACAGTCAAG | ATTTTCCCCT | CCCCACCCCC | TCCCTCTCTA | CAGCCCAGGT | 7440
| CTCTGCAGAG | AACACCTGGC | CTGACCACCC | TCCCTCTCTA | CAGCCCAGGT | GTTCAGAAGG | 7500
| GAGTCCTAGG | GGACTGAGAG | GAGGGCGCCCA | CGCCCCAGGA | AGCCGAGGCC | | 7560

*Fig. 3(16)*

```
TTGAGCTGGG GGGGGGGGCG AGGGTTGGAG GCACGAACTG GATGATCCCT GAGCACAACT    7620
GGGCCTAATC TAATTAGGGT GTTCCCAGCC CAAAGCAGCC TGGGCCATTT AACCCTTCAA    7680
GTGCCTCACT GAAGACTCAG GGAGAGATC  AGCTTGTACT CTCTCCATGG TCCCCCAGGA    7740
GGGTTCCTGG GTGCCCCTGG CTCATTCCCA CATCCAGAGG TTTTGTGTCT TCCTGGCATC    7800
TAACCCTCAG TTGTGCTCTG TGGCTGGCAC AGCTGCCCCG TGGAGGCTCT TGGTAATGTA    7860
CAAGGCATCA GAGGTGGACA TGGGATGGGG ATACATAGGG ATGGAGCCAA ATAGCACCTC    7920
AAGGTGGGGT GATATACAAT AAAGCTTGTC ACCCTGACGC TCAGAAAGCC TACTCATGAT    7980
GATCACAATT GTTGACATCA CTCTGGGACA TGTAGTGAGA CCCTAGCTCA AAACACAGAC    8040
```

Fig. 3(17)

```
AGTAGCTTTA AGAGTCAGCT TGTGACTTAA TACTGGAACT CAGGGCCTAA TAGGTGCTGG    8100

GTGATGCTCG CCTCACTCCC TGTTTAGTGA GATCTCTGCG CTAATCTCCA CCCCAGCTGG    8160

GTGGGCTGCT CTGTCCCCTT GAGGGCAGGA ATGTGTGTCT TCCATCAGAG ATAGGACCCG    8220

TGGTAGCAGC AACTGCTGCT GGCTGTTTCT GGAATATTAA ATGACAGTAA TCTATCAGGC    8280

CTGGGTGAGT AGCTAAACAGG GGTGGGGGCG TGGTCTGGAA AACGCAGATA GGGTCATAGG   8340

AGCCACTGCA GCCTAGATTA CACCACTGGG TGTTCTGTCA CTAGGCCATT CTCACCAAGC    8400

AGTCCTCAGA ACTGGGAGCA CTGTTGCCAG CATTTAATGC CAGCATTTAA TGCCAGCATT    8460

AGGGGAGGCA GAGGCAGAAG GATCTCTCTG AGTTCAAGGC CATCCTGAAT TTACATAAAG    8520
```

AGCTCCAGGC CAGCCAGGGT GCGCAGTAAA ACCTTGTCTC AAAAAACAAA GCATCTTTAG    8580

TGACCAGGCT TGCTCCACCC CCAGTGACCA CGGACCCCCC ACCCGACGTG CACGTGAGCC    8640

GCGTTGGGGG CCTGGAGGAC CAGCTGAGTG TGCGCTGGGT CTCACCACCA GCTCTCAAGG    8700

ATTTCCTCTT CCAAGCCAAG TACCAGATCC GCTACCGCGT GGAGGACAGC GTGGACTGGA    8760

AGGTGCCCGT CCCGCCCCGG ACCCGCCCCT GACCCCGCCC CCGGCATCTG ACTCCCTCCT    8820

CACCGTGCAG GTGGTGGATG ACGTCAGCAA CCAGACCTCC TGCCGTCTCG CGGGCCTGAA    8880

GCCCGGCACC GTTTACTTCG TCCAAGTGCG TTGTAACCCA CCCCACCGCT GCCTCCACCC    8940

AAAGGCGGGA ATCTGGAGCG AGTGGAGCCA CCCCACCCC GCCTCCACCC CTCGAAGTGG    9000

| | | | | |
|---|---|---|---|---|
| TGAGCACCTC | TCCAGGGCTG | GCTGGCCCAT | GGAATCCCCA | ATCCATCCTG | TTCCTTCCCC | 9060 |
| CCCACCCTTT | TTTTGAGACA | GCGTCTTCAG | GTAGCGCATG | CTGGCCTTAA | ATTCAGTATG | 9120 |
| TAGTCAAGGA | TGACCTCGAG | CTCCTGGTCT | TTTTGTCTCC | ACTTAGAGAC | AATGGCCAGT | 9180 |
| GGCCATCACC | ACCTTTGGGA | GACTAGCCAT | GGAGTCTATT | TAGCCTGTCA | TTTGGTGACA | 9240 |
| GATGGAGTAC | AACAGTGTGA | CCTCTTGTAA | GAGAACTGAA | GACAGGCTGT | TTTTAACCCC | 9300 |
| AATATCCTAG | GCTCTCTAGA | GGTTAACTTT | ATATAAAATA | GAGACTATTA | CAGCCAGTTA | 9360 |
| TCACATGGTC | CCACAGAACC | TTTTGTCACA | CAACCTATAG | ACCACAGTGC | CTGTGCCTAC | 9420 |
| CACATAAGGG | TCTCTACTGC | TGGCCCACCC | CTCCAACCCT | TAAAAGGTAA | CCTAGGCAGC | 9480 |

Fig. 3(20)

```
CTTAATATATT GCAATCCTCC TACCTCAGCC TCTTGAATGC TCAGAAACCA GGCATTAACC   9540
CAAGTTCTC TTCTCTGGGT CCCTTTCTTA AGGTGGGAGG GCCTAAAGAT GACTTCCTTT    9600
GTCCTGAAGA CTCTCCGAGC CCATGGATCT GCACTCTCTA ATATGAAATA TATTGCATAA   9660
AATGTCTGGC CTCAGTTTCC CCACCTGTCA GGTTTAGGCA GCACAGTCGG TCCAAGACAC   9720
TTCATTATTT GCAGGCAGTA TAAGAAGAAG CTCCCATCCC CCACCCGCTT CCTCCGGTCC   9780
CTAAGACAGA ATACTTCTAC ACTGAAACTG AACTCTCGCA DACGCATATG CTCACTTTAA    9840
TGATGATGAA ATAATGGGGA AACTGAGGCT CCTGGAGGAA GAGGGTCAAA               9900
ACCAGCTCCA GGAAGCTCTC CAGCCCCCAT CCGGGCCTCT CCAGGTTCTG GGCTTGGGCGG   9960
```

*Fig. 3(21)*

```
GAGTGAACAC AGCTGGGAGG GGCTGGAGCC TGGGAGCTTT GGCCCTTGCT CGTGCCCAGC    10020

ACCTGCGATT CTTGCACGGG AGCCAGCAGG CGGCTGCGTC CGCCCGAGAG ACTGAAGAAG    10080

CCGGGGGTAG GGTTGGAGGG AGTAAGCAG GGGCTGTGGG GGCCGAAGCT TGTGCCAGGG     10140

CCTGTCAGCG AGTCCCCAGT TTTATTTATG GCGTGAGGCC GATGTCCTTA TCCGCTGGCC    10200

TGCTGGGGA TGGCTGCGGC TGGGGATTGG ACCCAAGGGC TGGCTTCCCA CTCAGTCCTC     10260

CAGCCCCACTC CATGTCACAC CCGTGCATTC TCTGAGGCTT ATCTTGGGAA CCCGCCCTTG   10320

TTCTGTGCTG TCTGTCTCTA TTTCTGTCAT TCACTTTCCC AGAGCCTTTT TTTTATGCTT    10380

TTAATATAAC TACGTTTTAA AAATTGCTTT TGTATAATGT GTGTGCCTTC GTGAGCGTGC    10440
```

GTGCCACAAC ACACACGTGA AGGTTAGAGA ACTTTGTTGA GTAGGCTCCT TCCACCATGT    10500

GGGACTAGGG CTGGCGACAA GAGCAATTAC TGAGTCATCT CGCCAGCCCC TCACCCCTCA    10560

CTTCCCATCC TGTTTGGATA GTCATAGGTA ATCGAAGGTA AATCGCTGGC TTTAATTTCG    10620

TAGCTATCCT GCCTCAGCCT ACCAAGTGCT GTGCTACCAC GTTTGTGGGA GGGGCTCTCC    10680

TCCCAGTGTC TGGGGGTACA CAGTCCCAAG ATCTCTGCTT TCTAGGTCTT TGTCTTAGTT    10740

TGCCCCTTGC TTTGTCCGTG TCCCTAGAGT CTCCGGCCCC ACTTAGTCTC CATTGATTTC    10800

CTTTCTGACC GAATACTCGG TTTTACCTCC CACTGATTTG ACTCCCTCCT TTGCTTGTCT    10860

CCATCGCCGT GGCATTGCCA TTCCTCTGGG TGACTCTGGG TCCACACCTG ACACCTTTCC    10920

```
CAACTTTCCC CAGCCGAAGC TGGTCTGGTA TGGGAGGCCG CCGTCCCGCG CGGCCTCCT    10980

GCTGGCCGCG CCCCAACACT GCCGCTCCAT TCTCTTTAGA GCGCCCGGGC CCGGGGCGCG   11040

GGGTGTGCGA GCCGCGGGGC GGCGAGCCCA GCTCGGGCCC GGTGCGGGCGC GAGCTCAAGC  11100

AGTTCCTCGG CTGGCTCAAG AAGCACGGCAT ACTGCTCGAA CCTTAGTTTC CGCCTGTACG  11160

ACCAGTGGCG TGCTTGGATG CAGAAGTCAC ACAAGACCCG AAACCAGGTA GGAAAGTTGG   11220

GGGAGGCTTG CGTGGGGGGT AAAGGAGCAG AGGAAGAGAG AGACCCGGGT GAGCAGCCTC   11280

CACAACACCG CACTCTTCTT TCCAAGCACA GGACGAGGGG ATCCTGCCCT CGGGCAGACG   11340

GGGTGCGGCG AGAGGTAAGG GGGTCTGGGT GAGTGGGGCC TACAGCAGTC TAGATGAGGC   11400
```

*Fig. 3(24)*

```
CCTTTCCCCT CCTTCGGTGT TGCTCAAAGG GATCTCTTAG TGCTCATTTC ACCCACTGCA    11460

AAGAGCCCCA GGTTTACTG CATCATCAAG TTGCTGAAGG GTCCAGGCTT AATGTGGCCT    11520

CTTTTCTGCC CTCAGGTCCT GCCGGCTAAA CTCTAAGGAT AGGCCATCCT CCTGCTGGGT    11580

CAGACCTGGA GGCTCACCTG AATTGGAGCC CCTCTGTACC AACCACAGCT CAAAGAAACC    11640

TACCAGAGGC TGGGCACAAT GAGCTCCCAC AACCACAGCT TTGGTCCACA TGATGGTCAC    11700

ACTTGGATAT ACCCCAGTGT GGGTAGGGTT GGGGTATTGC AGGGCCTCCC AAGAGTCTCT    11760

TTAAATAAAT AAAGGAGTTG TTCAGGTCCC GATGGCCAGT GTGTTTGGGG CCTATGTGCT    11820

GGGGTGGGGG GA    11832
```

```
G----CCGTTGCTGCCCTG--------CTGCTGCTCTGC  Human NR6
GCGGCCGTGTCCTGGTGCGCTGTGCTCTG            Mouse NR6

TCCCCAGGATCCCACGCTTCTCATGGCTCCCCTGCTG    Human NR6
CCCCAGGAGCCCACACTTCTCATGGCTCCCCTGCAA     Mouse NR6

CTACTGACCCTCAATGGCGCCCTGCCCCCTGAGCTC     Human NR6
CTACTGACCCTCAATGGCGCCCTGCCCCTGAGCTG      Mouse NR6

TGGGTCCAGGCAGCGGTCGGGGACAACCTCGTGTGCCAC  Human NR6
TGGGTCCAGGCAGCGGTCGGAGACAATCTGGTGTGCAC   Mouse NR6

CCCAGAGAAACCCGTCAACATCAGCTGTGGTCCAAGAAC  Human NR6
CCCGGAGAAGCCCGTCAACATCAGCTGTGGTCCGGAAC   Mouse NR6

CCTCCACCAACTACTCCCCTCAAGTACACAAGCTTAGGTGG Human NR6
CTTCCACCAACTACTCCCCTCAAGTACACAAGCTGAGGTGG Mouse NR6

CTGCCACATCCCCAAGGACCTGGCTCTCTTTACGCCCTAT Human NR6
ATGCCAATCCCCAAGGACCTGGCTCTCTTGACCCCTAT   Mouse NR6
```

*Fig. 6(2)*

```
519   GAGATCTGGGTGGAGGCCACCAACCGCTGGCTGCCCGATGT
531   GAGATCTGGGTGGA[A]GCCACCAA[T]CG CCTG[A]GCTC[A][A][A]GATGT

709   CCGCCCGACGTGCACGTGAGCCCGGTTCGGAGGACCAGCTGAG
721   cc[A]CCCGACGTGCACGTGAGCCCGCGT[T]GGGGGCCTGGAGGACCAGCTGAG

799   TTTCAAGCCAAATACCAGATCCGCTACCGAGTGGAGGACAGTGTGGACTG
811   TT[G]CAAGCCAA[G]TACCAGATCCGCTACCG[G]GTGGAGGACAG[T]GTGGACTG

889   CTGGCCGGCCTGAAACCCGGCACCGTGTACTTCGTGCAAGTGCGCTGCAA
901   CT[G]GC[G]GGCCTGAA[G]CCCGGCACCG[T]TACTTCGT[G]CAAGTGCG[C][T]G[T]AA

979   AGTGAGTGGAGCCACCCCACAGCCGCTCCACTCCCCGCAGTGAGCGCCC
991   AG[G]GAGTGGAGCCACCCCACAGC[G]G[C]CCTCCAC[G]C[C][T]C[G]A[A][T]GAGCGCCC

1069  CCGAGCTCGGGGCCGGTGCGGAGCTCAAGCAGTTCCTGGCT
1081  CC[G]AGCTCGG[G][C]CCGGTGCGGGAGCTCAAGCAGTTCCT[G]GGCT
```

*Fig. 6(3)*

```
ACTCACGCTGGATATCCTGGATGTGGTGACCACGGACCCC  Human NR6
[C]CTCAC[A][C]TGGAT[C]TCCTGGA[C]GTGGTGACCACGGACCCC  Mouse NR6

CGTGCGCTGGGTGTCGCCACCCGCCCTCAAGGATTTCCTC  Human NR6
[T]GTGCGCTGGGT[G]T[C][A]CCACC[G]GC[C]CTCAAGGATTTCCTC  Mouse NR6

GAAGGTGGTGGACGATGTGAGCAACCAGACCCTCCTGCCGC  Human NR6
GAAGGTGGTGGA[G]GA[G]GT[G]AGCAACCAGACCCTCCTGCC[G][T]  Mouse NR6

CCCCCTTTGGCATCTATGGCTCCAAGAAAGCCGGGATCTGG  Human NR6
CC[G][T]T[T]GG[C][A]T[C]TATGG[C]T[C][A]A[A][G][AA]AGCCGG[A]ATCTGG  Mouse NR6

GGGCCCGGGGCCGGGGCCGTGCGAACCGGGGGAGAG  Human NR6
GGGCCCGGGGCCGGGGCC[T]GTGC[C]AACCGGGGG[C][G]GAG  Mouse NR6

CAAGAAGCACGCGTACTGCTCCAACCTCAGCTTCCGCCTC  Human NR6
CAAGAAGCACGC[A]TACTGCTC[C]AACCT[A][AG][T]TTCCGCCT[G]  Mouse NR6
```

*Fig. 6(4)*

```
F·····················G----------------------------G
1159 TACGACCAGTGGCGAGCCTGGATGCAGAAGTCGCACAAGACCCGCAACCA
1171 TACGACCAGTGGCGAGCCTGGATGCAGAAGTCGCACAAGACCCGCAAACCA

1249 AGAGGTCCTGCCAGATAAGCTGTAGGGCTCAGGCCACCCTCCCTGCCAC
1261 AGAGGTCCTGCCAGATAAGCTGTAAGCTTAAGGATAGCCATCCTGCTGGTC

1339 GTACCCTCACTTCAGGCCACCTCAGCCCTGAGCCACCTCAGCAGGAGCTGGGGTGG
1351 TCTGGGCAACAAAGAAACTTACAGAGGTGGGGCACAATGAGCTCCCAC

1429 TGAGGCCACCTTTGGGTGCACCCCAGTGTGGGTGTGTGTGTGTGAGGG
1441 ACCCCAGTGTGGGTAGGGTTGGGGTATTGCAGGGCTTCCAAGAGTCTTC

1519 AGAAGGGGAGTCATTACTCCCCATTACCTAGGGCCCCTCCAAAAGATCC
1504
```

Fig. 6(5)

```
GGACGAGGGGATCCTGCCCTCGGGCAGAGACGGGCACGGGCG   Human NR6
GGACGAGGGGATCCTGCCTTCGGGCAGAGACGGGGTGGGCG    Mouse NR6

GTGGAGACGCAGAGGCCGAAACCAAACTGGGGCCACCTCT     Human NR6
AGACCTGGAGGCTCACCTGAATGGAGCCCCTCTGTAGCA      Mouse NR6

CCCCTGAGCTCCAACGGCCATAAACAGCTCTGACTCCCACG    Human NR6
AACCACAGCTTTGGTCCACATGATGTCACACTTGGATATA     Mouse NR6

TTGGTTGAGTTGCCTAGAACCCCTGCCAGGGCTGGGGGTG     Human NR6
GTGTGCCGAATTC                                Mouse NR6

Human NR6
                                             Mouse NR6
```

Fig. 6(6)

```
  1  MetProAlaGlyArgArgGlyProAlaAlaGlnSerAlaArgArgPro
  1  MetProAlaGlyArgGlyProGlyProValAlaGlnSerAlaArgArgPro

27  ValLeuGlyAlaProArgArgAlaGlySerGlyAlaHisThrAlaValIle
 31  ValLeuGlyValProArgGlyGlySerGlyAlaHisThrAlaValIle

57  AlaThrCysSerValHisGlyAspProProGlyAlaThrAlaGluGly
 61  AlaThrCysSerHisGlyAspThrProGlyAlaThrAlaGluGly

87  SerArgValLeuAsnAlaSerThrLeuAlaLeuAlaLeuAlaAsnLeu
 91  SerArgLeuLeuAsnThrSerThrLeuAlaLeuAlaLeuAlaAsnLeu

117  AlaArgAspGlySerIleLeuAlaGlySerCysLeuCysLeuTyrValGlyLeu
121  AlaArgAspGlySerIleLeuAlaGlySerCysLeuCysLeuTyrValGlyLeu

147  MetLysAspLeuThrCysArgTrpThrProGlyAlaHisGlyGluThr
151  MetLysAspLeuThrCysArgTrpThrProGlyAlaHisGlyGluThr
```

Fig. 7(1)

```
Pro - ProLeuLeuProLeu - - - LeuLeuLeuCys        Human NR6
ProArgProLeuSerSerLeuTrpSerProLeuLeuLeuCys     Mouse NR6

SerProGlnAspProThrLeuLeuIleGlySerSerLeuLeu      Human NR6
SerProGlnAspProThrLeuLeuIleGlySerSerLeuGln      Mouse NR6

LeuTyrTrpThrLeuAsnGlyArgArgLeuProProGluLeu      Human NR6
LeuTyrTrpThrLeuAsnGlyArgArgLeuProSerGluLeu      Mouse NR6

AsnGlySerArgGlnSerGlyAspAsnLeuValCysHis         Human NR6
AsnGlySerArgGlnSerGlyAspAsnLeuValCysHis         Mouse NR6

ProProLysProValAsnIleSerCysTrpSerLysAsn         Human NR6
ProProLysProPheAsnIleSerCysTrpSerArgAsn         Mouse NR6

PheLeuHisThrAsnTyrSerLeuLysTyrLeuArgTrp         Human NR6
PheLeuHisThrAsnTyrSerLeuLysTyrLeuArgTrp         Mouse NR6
```

Fig. 7(2)

177 TyrGlyGlnAspAsnThrCysGluGluTyrHisThrValGlyProHis
181 TyrGlyGlnAspAsnThrCysGluGluTyrHisThrValGlyProHis

207 GluIleTrpValGluAlaThrAsnArgLeuGlySerAlaArgSerAsp
211 GluIleTrpValGluAlaThrAsnArgLeuGlySerAlaArgSerAsp

237 ProProAspValHisValSerArgValGlyGlyLeuGluAspGlnLeu
241 ProProAspValHisValSerArgValGlyGlyLeuGluAspGlnLeu

267 PheGlnAlaAlaLysTyrGlnIleArgTyrArgValGluAspSerValAsp
271 PheGlnAlaAlaLysTyrGlnIleArgTyrArgValGluAspSerValAsp

297 LeuAlaGlyLeuLeuLysProGlyThrValTyrPheValGlnValArgCys
301 LeuAlaGlyLeuLeuLysProGlyThrValTyrPheValGlnValArgCys

*Fig. 7(3)*

```
SerCysHisIleProLysAspLeuAlaLeuPheThrProTyr  Human NR6
SerCysHisIleProLysAspLeuAlaLeuPheThrProTyr  Mouse NR6

ValLeuThrLeuAspIleLeuAspValThrThrAspPro     Human NR6
ValLeuThrLeuAspValLeuAspValThrThrAspPro     Mouse NR6

SerValArgTrpValSerProProAlaLeuLysAspPheLeu  Human NR6
SerValArgTrpValSerProProAlaLeuLysAspPheLeu  Mouse NR6

TrpLysValAlaAspValSerAsnGlnThrSerCysArg     Human NR6
TrpLysValAlaAspValSerAsnGlnThrSerCysArg     Mouse NR6

AsnProPheGlyIleTyrGlySerLysLysAlaGlyIleTrp  Human NR6
AsnProPheGlyIleTyrGlySerLysLysAlaGlyIleTrp  Mouse NR6
```

Fig. 7(4)

327 SerGluTrpSerHisProThrAlaAlaSerThrProArgSerGluArg
331 SerGluTrpSerHisProThrAlaAlaSerThrProArgAsnGluArg

357 ProSerSerGlyProValArgArgGluLeuLysGlnPheLeuGlyTrp
361 ProSerSerGlyProValArgArgGluLeuLysGlnPheLeuGlyTrp

387 TyrAspGlnTrpArgAlaTrpMetGlnLysSerHisLysThrArgAsn
391 TyrAspGlnTrpArgAlaTrpMetGlnLysSerHisLysThrArgAsn

417 ArgGlyProAlaArgter
421 ArgGlyProAla - Gly

Fig. 7(5)

ProGlyProGlyGlyGlyAlaCysGluProArgGlyGlyGlu Human NR6
ProGlyProGlyGlyGly[Val]Cys[Gln]ProArgGlyGlyGlu Mouse NR6

LeuLysLysHisAlaTyrCysSerAsnLeuSerPheArgLeu Human NR6
LeuLysLysHisAlaTyrCysSerAsnLeuSerPheArgLeu Mouse NR6

GlnAspGluGlyIleLeuProSerGlyArgArgGlyThrAla Human NR6
GlnAspGluGlyIleLeuProSerGlyArgArgGly[Ala]Ala Mouse NR6

Human NR6
Mouse NR6

*Fig. 7(6)*

Western Blot Analysis of M2 Eluted Fractions

WESTERN Conditions:

| | |
|---|---|
| Gel: | Novex gel 8-16% |
| Sample buffer: | Non reducing |
| Transfer: | 25mM Glycine, 192mM Glycine, 20% MeOH |
| Transfer conditions: | 100V, 1 Hour |
| Blocking buffer: | 1% non fat skim, in TBS Overnight agitation, cold room |
| 1' Ab: | 1:500 in TBS 1hr, RT |
| Wash: | 6x5min |
| 2' Ab: | Streptavidin Peroxidase 1:5000 in TBS 1hr, RT |

SEQUENCE LISTING

<160> NUMBER OF SEQ ID NOS: 54

<210> SEQ ID NO 1

```
<211> LENGTH: 5
<212> TYPE: PRT
<213> ORGANISM: Unknown
<220> FEATURE:
<223> OTHER INFORMATION: Description of Unknown Organism: haemopoietin
      receptor
<220> FEATURE:
<221> NAME/KEY: UNSURE
<222> LOCATION: (3)
<223> OTHER INFORMATION: Unsure at position 3

<400> SEQUENCE: 1

Trp Ser Xaa Trp Ser
  1               5

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: M116 probe

<400> SEQUENCE: 2
actcgctcca gattcccgcc tttt                                         24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:M108 probe

<400> SEQUENCE: 3
tcccgccttt ttcgacccat agat                                         24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:M159 probe

<400> SEQUENCE: 4
ggtacttggc ttggaagagg aaat                                         24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:M242 probe

<400> SEQUENCE: 5
cggctcacgt gcacgtcggg tggg                                         24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:M112 probe

<400> SEQUENCE: 6
agctgctgtt aaagggcttc tc                                           22

<210> SEQ ID NO 7
<211> LENGTH: 15
```

```
<212> TYPE: DNA
<213> ORGANISM: Unknown
<220> FEATURE:
<223> OTHER INFORMATION: Description of Unknown Organism:Unsure
<220> FEATURE:
<221> NAME/KEY: unsure
<222> LOCATION: (1)
<223> OTHER INFORMATION: Unsure at position 1
<220> FEATURE:
<221> NAME/KEY: unsure
<222> LOCATION: (7)
<223> OTHER INFORMATION: Unsure at position 7
<220> FEATURE:
<221> NAME/KEY: unsure
<222> LOCATION: (10)
<223> OTHER INFORMATION: Unsure at position 10

<400> SEQUENCE: 7
rctccartcr ctcca                                                15

<210> SEQ ID NO 8
<211> LENGTH: 15
<212> TYPE: DNA
<213> ORGANISM: Unknown
<220> FEATURE:
<223> OTHER INFORMATION: Description of Unknown Organism:Unsure
<220> FEATURE:
<221> NAME/KEY: unsure
<222> LOCATION: (1)
<223> OTHER INFORMATION: Unsure at position 1
<220> FEATURE:
<221> NAME/KEY: unsure
<222> LOCATION: (7)
<223> OTHER INFORMATION: Unsure at position 7
<220> FEATURE:
<221> NAME/KEY: unsure
<222> LOCATION: (10)
<223> OTHER INFORMATION: Unsure at position 10

<400> SEQUENCE: 8
rctccaytcr ctcca                                                15

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:1944 probe

<400> SEQUENCE: 9
aagtgtgacc atcatgtgga c                                         21

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:2106 probe

<400> SEQUENCE: 10
ggaggtgtta aggaggcg                                             18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:2120 probe

<400> SEQUENCE: 11
```

```
atgcccgcgg gtcgcccg                                                      18
```

<210> SEQ ID NO 12
<211> LENGTH: 1629
<212> TYPE: DNA
<213> ORGANISM: Unknown
<220> FEATURE:
<221> NAME/KEY: CDS
<222> LOCATION: (124)..(1362)
<220> FEATURE:
<223> OTHER INFORMATION: Description of Unknown Organism:Murine NR6.1

<400> SEQUENCE: 12

```
ggcacgagct tcgctgtccg cgcccagtga cgcgcgtgcg gacccgagcc ccaatctgca      60
ccccgcagac tcgcccccgc cccataccgg cgttgcagtc accgcccgtt gcgcgccacc     120 ccc atg ccc gcg ggt cgc ccg ggc ccc gtc gcc caa tcc gcg cgg cgg       168
    Met Pro Ala Gly Arg Pro Gly Pro Val Ala Gln Ser Ala Arg Arg
    1               5                   10                  15 ccg ccg cgg ccg ctg tcc tcg ctg tgg tcg cct ctg ttg ctc tgt gtc       216
Pro Pro Arg Pro Leu Ser Ser Leu Trp Ser Pro Leu Leu Leu Cys Val
                20                  25                  30 ctc ggg gtg cct cgg ggc gga tcg gga gcc cac aca gct gta atc agc       264
Leu Gly Val Pro Arg Gly Gly Ser Gly Ala His Thr Ala Val Ile Ser
            35                  40                  45 ccc cag gac ccc acc ctt ctc atc ggc tcc tcc ctg caa gct acc tgc       312
Pro Gln Asp Pro Thr Leu Leu Ile Gly Ser Ser Leu Gln Ala Thr Cys
        50                  55                  60 tct ata cat gga gac aca cct ggg gcc acc gct gag ggg ctc tac tgg       360
Ser Ile His Gly Asp Thr Pro Gly Ala Thr Ala Glu Gly Leu Tyr Trp
    65                  70                  75 acc ctc aat ggt cgc cgc ctg ccc tct gag ctg tcc cgc ctc ctt aac       408
Thr Leu Asn Gly Arg Arg Leu Pro Ser Glu Leu Ser Arg Leu Leu Asn
80                  85                  90                  95 acc tcc acc ctg gcc ctg gcc ctg gct aac ctt aat ggg tcc agg cag       456
Thr Ser Thr Leu Ala Leu Ala Leu Ala Asn Leu Asn Gly Ser Arg Gln
                100                 105                 110 cag tca gga gac aat ctg gtg tgt cac gcc cga gac ggc agc att ctg       504
Gln Ser Gly Asp Asn Leu Val Cys His Ala Arg Asp Gly Ser Ile Leu
            115                 120                 125 gct ggc tcc tgc ctc tat gtt ggc ttg ccc cct gag aag ccc ttt aac       552
Ala Gly Ser Cys Leu Tyr Val Gly Leu Pro Pro Glu Lys Pro Phe Asn
        130                 135                 140 atc agc tgc tgg tcc cgg aac atg aag gat ctc acg tgc cgc tgg aca       600
Ile Ser Cys Trp Ser Arg Asn Met Lys Asp Leu Thr Cys Arg Trp Thr
    145                 150                 155 ccg ggt gca cac ggg gag aca ttc tta cat acc aac tac tcc ctc aag       648
Pro Gly Ala His Gly Glu Thr Phe Leu His Thr Asn Tyr Ser Leu Lys
160                 165                 170                 175 tac aag ctg agg tgg tac ggt cag gat aac aca tgt gag gag tac cac       696
Tyr Lys Leu Arg Trp Tyr Gly Gln Asp Asn Thr Cys Glu Glu Tyr His
                180                 185                 190 act gtg ggc cct cac tca tgc cat atc ccc aag gac ctg gcc ctc ttc       744
Thr Val Gly Pro His Ser Cys His Ile Pro Lys Asp Leu Ala Leu Phe
            195                 200                 205 act ccc tat gag atc tgg gtg gaa gcc acc aat cgc cta ggc tca gca       792
Thr Pro Tyr Glu Ile Trp Val Glu Ala Thr Asn Arg Leu Gly Ser Ala
        210                 215                 220 aga tct gat gtc ctc aca ctg gat gtc ctg gac gtg gtg acc acg gac       840
Arg Ser Asp Val Leu Thr Leu Asp Val Leu Asp Val Val Thr Thr Asp
    225                 230                 235
```

-continued

| | | |
|---|---|---|
| ccc cca ccc gac gtg cac gtg agc cgc gtt ggg ggc ctg gag gac cag<br>Pro Pro Pro Asp Val His Val Ser Arg Val Gly Gly Leu Glu Asp Gln<br>240                        245                    250                    255 | 888 |
| ctg agt gtg cgc tgg gtc tca cca cca gct ctc aag gat ttc ctc ttc<br>Leu Ser Val Arg Trp Val Ser Pro Pro Ala Leu Lys Asp Phe Leu Phe<br>                    260                    265                    270 | 936 |
| caa gcc aag tac cag atc cgc tac cgc gtg gag gac agc gtg gac tgg<br>Gln Ala Lys Tyr Gln Ile Arg Tyr Arg Val Glu Asp Ser Val Asp Trp<br>            275                    280                    285 | 984 |
| aag gtg gtg gat gac gtc agc aac cag acc tcc tgc cgt ctc gcg ggc<br>Lys Val Val Asp Asp Val Ser Asn Gln Thr Ser Cys Arg Leu Ala Gly<br>290                        295                    300 | 1032 |
| ctg aag ccc ggc acc gtt tac ttc gtc caa gtg cgt tgt aac cca ttc<br>Leu Lys Pro Gly Thr Val Tyr Phe Val Gln Val Arg Cys Asn Pro Phe<br>            305                    310                    315 | 1080 |
| ggg atc tat ggg tcg aaa aag gcg gga atc tgg agc gag tgg agc cac<br>Gly Ile Tyr Gly Ser Lys Lys Ala Gly Ile Trp Ser Glu Trp Ser His<br>320                        325                    330                    335 | 1128 |
| ccc acc gct gcc tcc acc cct cga agt gag cgc ccg ggc ccg ggc ggc<br>Pro Thr Ala Ala Ser Thr Pro Arg Ser Glu Arg Pro Gly Pro Gly Gly<br>                    340                    345                    350 | 1176 |
| ggg gtg tgc gag ccg cgg ggc ggc gag ccc agc tcg ggc ccg gtg cgg<br>Gly Val Cys Glu Pro Arg Gly Gly Glu Pro Ser Ser Gly Pro Val Arg<br>            355                    360                    365 | 1224 |
| cgc gag ctc aag cag ttc ctc ggc tgg ctc aag aag cac gca tac tgc<br>Arg Glu Leu Lys Gln Phe Leu Gly Trp Leu Lys Lys His Ala Tyr Cys<br>370                        375                    380 | 1272 |
| tcg aac ctt agt ttc cgc ctg tac gac cag tgg cgt gct tgg atg cag<br>Ser Asn Leu Ser Phe Arg Leu Tyr Asp Gln Trp Arg Ala Trp Met Gln<br>            385                    390                    395 | 1320 |
| aag tca cac aag acc cga aac cag gtc ctg ccg gct aaa ctc<br>Lys Ser His Lys Thr Arg Asn Gln Val Leu Pro Ala Lys Leu<br>400                        405                    410 | 1362 |
| taaggatagg ccatcctcct gctgggtcag acctggaggc tcacctgaat tggagcccct | 1422 |
| ctgtaccatc tgggcaacaa agaaacctac cagaggctgg ggcacaatga gctcccacaa | 1482 |
| ccacagcttt ggtccacatg atggtcacac ttggatatac cccagtgtgg gtaaggttgg | 1542 |
| ggtattgcag ggcctcccaa caatctcttt aaataaataa aggagttgtt caggtaaaaa | 1602 |
| aaaaaaaaaa aaaaaaaaaa aaaaaaa | 1629 |

<210> SEQ ID NO 13
<211> LENGTH: 413
<212> TYPE: PRT
<213> ORGANISM: Unknown
<220> FEATURE:
<223> OTHER INFORMATION: Description of Unknown Organism:Murine NR6.1

<400> SEQUENCE: 13

Met Pro Ala Gly Arg Pro Gly Pro Val Ala Gln Ser Ala Arg Arg Pro
1                5                    10                    15

Pro Arg Pro Leu Ser Ser Leu Trp Ser Pro Leu Leu Leu Cys Val Leu
                    20                    25                    30

Gly Val Pro Arg Gly Gly Ser Gly Ala His Thr Ala Val Ile Ser Pro
                35                    40                    45

Gln Asp Pro Thr Leu Leu Ile Gly Ser Ser Leu Gln Ala Thr Cys Ser
        50                    55                    60

Ile His Gly Asp Thr Pro Gly Ala Thr Ala Glu Gly Leu Tyr Trp Thr
65                70                    75                    80

```
Leu Asn Gly Arg Arg Leu Pro Ser Glu Leu Ser Arg Leu Leu Asn Thr
                85                  90                  95

Ser Thr Leu Ala Leu Ala Leu Ala Asn Leu Asn Gly Ser Arg Gln Gln
            100                 105                 110

Ser Gly Asp Asn Leu Val Cys His Ala Arg Asp Gly Ser Ile Leu Ala
        115                 120                 125

Gly Ser Cys Leu Tyr Val Gly Leu Pro Pro Glu Lys Pro Phe Asn Ile
    130                 135                 140

Ser Cys Trp Ser Arg Asn Met Lys Asp Leu Thr Cys Arg Trp Thr Pro
145                 150                 155                 160

Gly Ala His Gly Glu Thr Phe Leu His Thr Asn Tyr Ser Leu Lys Tyr
                165                 170                 175

Lys Leu Arg Trp Tyr Gly Gln Asp Asn Thr Cys Glu Glu Tyr His Thr
            180                 185                 190

Val Gly Pro His Ser Cys His Ile Pro Lys Asp Leu Ala Leu Phe Thr
        195                 200                 205

Pro Tyr Glu Ile Trp Val Glu Ala Thr Asn Arg Leu Gly Ser Ala Arg
    210                 215                 220

Ser Asp Val Leu Thr Leu Asp Val Leu Asp Val Thr Thr Asp Pro Pro
225                 230                 235                 240

Pro Pro Asp Val His Val Ser Arg Val Gly Gly Leu Glu Asp Gln Leu
                245                 250                 255

Ser Val Arg Trp Val Ser Pro Pro Ala Leu Lys Asp Phe Leu Phe Gln
            260                 265                 270

Ala Lys Tyr Gln Ile Arg Tyr Arg Val Glu Asp Ser Val Asp Trp Lys
        275                 280                 285

Val Val Asp Asp Val Ser Asn Gln Thr Ser Cys Arg Leu Ala Gly Leu
    290                 295                 300

Lys Pro Gly Thr Val Tyr Phe Val Gln Val Arg Cys Asn Pro Phe Gly
305                 310                 315                 320

Ile Tyr Gly Ser Lys Lys Ala Gly Ile Trp Ser Glu Trp Ser His Pro
                325                 330                 335

Thr Ala Ala Ser Thr Pro Arg Ser Glu Arg Pro Gly Pro Gly Gly Gly
            340                 345                 350

Val Cys Glu Pro Arg Gly Gly Glu Pro Ser Ser Gly Pro Val Arg Arg
        355                 360                 365

Glu Leu Lys Gln Phe Leu Gly Trp Leu Lys Lys His Ala Tyr Cys Ser
    370                 375                 380

Asn Leu Ser Phe Arg Leu Tyr Asp Gln Trp Arg Ala Trp Met Gln Lys
385                 390                 395                 400

Ser His Lys Thr Arg Asn Gln Val Leu Pro Ala Lys Leu
                405                 410
```

<210> SEQ ID NO 14
<211> LENGTH: 1673
<212> TYPE: DNA
<213> ORGANISM: Unknown
<220> FEATURE:
<221> NAME/KEY: CDS
<222> LOCATION: (125)..(1399)
<220> FEATURE:
<223> OTHER INFORMATION: Description of Unknown Organism:Murine NR6.2

<400> SEQUENCE: 14

```
ggcacgagct tcgctgtccg cgcccagtga cgcgcgtgcg gacccgagcc ccaatctgca    60
ccccgcagac tcgcccccgc cccataccgg cgttgcagtc accgcccgtt gcgcgccacc   120
```

-continued

| | |
|---|---|
| ccca atg ccc gcg ggt cgc ccg ggc ccc gtc gcc caa tcc gcg cgg cgg<br>     Met Pro Ala Gly Arg Pro Gly Pro Val Ala Gln Ser Ala Arg Arg<br>      1               5                    10                      15 | 169 |
| ccg ccg cgg ccg ctg tcc tcg ctg tgg tcg cct ctg ttg ctc tgt gtc<br>Pro Pro Arg Pro Leu Ser Ser Leu Trp Ser Pro Leu Leu Leu Cys Val<br>                  20                    25                    30 | 217 |
| ctc ggg gtg cct cgg ggc gga tcg gga gcc cac aca gct gta atc agc<br>Leu Gly Val Pro Arg Gly Gly Ser Gly Ala His Thr Ala Val Ile Ser<br>           35                      40                    45 | 265 |
| ccc cag gac ccc acc ctt ctc atc ggc tcc tcc ctg caa gct acc tgc<br>Pro Gln Asp Pro Thr Leu Leu Ile Gly Ser Ser Leu Gln Ala Thr Cys<br>       50                      55                    60 | 313 |
| tct ata cat gga gac aca cct ggg gcc acc gct gag ggg ctc tac tgg<br>Ser Ile His Gly Asp Thr Pro Gly Ala Thr Ala Glu Gly Leu Tyr Trp<br> 65                    70                    75 | 361 |
| acc ctc aat ggt cgc cgc ctg ccc tct gag ctg tcc cgc ctc ctt aac<br>Thr Leu Asn Gly Arg Arg Leu Pro Ser Glu Leu Ser Arg Leu Leu Asn<br> 80                    85                    90                    95 | 409 |
| acc tcc acc ctg gcc ctg gcc ctg gct aac ctt aat ggg tcc agg cag<br>Thr Ser Thr Leu Ala Leu Ala Leu Ala Asn Leu Asn Gly Ser Arg Gln<br>           100                    105                  110 | 457 |
| cag tca gga gac aat ctg gtg tgt cac gcc cga gac ggc agc att ctg<br>Gln Ser Gly Asp Asn Leu Val Cys His Ala Arg Asp Gly Ser Ile Leu<br>        115                    120                  125 | 505 |
| gct ggc tcc tgc ctc tat gtt ggc ttg ccc cct gag aag ccc ttt aac<br>Ala Gly Ser Cys Leu Tyr Val Gly Leu Pro Pro Glu Lys Pro Phe Asn<br>       130                    135                  140 | 553 |
| atc agc tgc tgg tcc cgg aac atg aag gat ctc acg tgc cgc tgg aca<br>Ile Ser Cys Trp Ser Arg Asn Met Lys Asp Leu Thr Cys Arg Trp Thr<br>145                   150                    155 | 601 |
| ccg ggt gca cac ggg gag aca ttc tta cat acc aac tac tcc ctc aag<br>Pro Gly Ala His Gly Glu Thr Phe Leu His Thr Asn Tyr Ser Leu Lys<br>160                   165                    170                  175 | 649 |
| tac aag ctg agg tgg tac ggt cag gat aac aca tgt gag gag tac cac<br>Tyr Lys Leu Arg Trp Tyr Gly Gln Asp Asn Thr Cys Glu Glu Tyr His<br>                180                    185                  190 | 697 |
| act gtg ggc cct cac tca tgc cat atc ccc aag gac ctg gcc ctc ttc<br>Thr Val Gly Pro His Ser Cys His Ile Pro Lys Asp Leu Ala Leu Phe<br>           195                    200                  205 | 745 |
| act ccc tat gag atc tgg gtg gaa gcc acc aat cgc cta ggc tca gca<br>Thr Pro Tyr Glu Ile Trp Val Glu Ala Thr Asn Arg Leu Gly Ser Ala<br>       210                    215                  220 | 793 |
| aga tct gat gtc ctc aca ctg gat gtc ctg gac gtg gtg acc acg gac<br>Arg Ser Asp Val Leu Thr Leu Asp Val Leu Asp Val Val Thr Thr Asp<br>       225                    230                  235 | 841 |
| ccc cca ccc gac gtg cac gtg agc cgc gtt ggg ggc ctg gag gac cag<br>Pro Pro Pro Asp Val His Val Ser Arg Val Gly Gly Leu Glu Asp Gln<br>240                   245                    250                  255 | 889 |
| ctg agt gtg cgc tgg gtc tca cca cca gct ctc aag gat ttc ctc ttc<br>Leu Ser Val Arg Trp Val Ser Pro Pro Ala Leu Lys Asp Phe Leu Phe<br>                260                    265                  270 | 937 |
| caa gcc aag tac cag atc cgc tac cgc gtg gag gac agc gtg gac tgg<br>Gln Ala Lys Tyr Gln Ile Arg Tyr Arg Val Glu Asp Ser Val Asp Trp<br>           275                    280                  285 | 985 |
| aag gtg gtg gat gac gtc agc aac cag acc tcc tgc cgt ctc gcg ggc<br>Lys Val Val Asp Asp Val Ser Asn Gln Thr Ser Cys Arg Leu Ala Gly<br>        290                    295                  300 | 1033 |
| ctg aag ccc ggc acc gtt tac ttc gtc caa gtg cgt tgt aac cca ttc<br>Leu Lys Pro Gly Thr Val Tyr Phe Val Gln Val Arg Cys Asn Pro Phe | 1081 |

-continued

```
                   305                 310                 315
ggg atc tat ggg tcg aaa aag gcg gga atc tgg agc gag tgg agc cac       1129
Gly Ile Tyr Gly Ser Lys Lys Ala Gly Ile Trp Ser Glu Trp Ser His
320                 325                 330                 335 ccc acc gct gcc tcc acc cct cga agt gag cgc ccg ggc ccg ggc ggc       1177
Pro Thr Ala Ala Ser Thr Pro Arg Ser Glu Arg Pro Gly Pro Gly Gly
                340                 345                 350 ggg gtg tgc gag ccg cgg ggc ggc gag ccc agc tcg ggc ccg gtg cgg       1225
Gly Val Cys Glu Pro Arg Gly Gly Glu Pro Ser Ser Gly Pro Val Arg
            355                 360                 365 cgc gag ctc aag cag ttc ctc ggc tgg ctc aag aag cac gca tac tgc       1273
Arg Glu Leu Lys Gln Phe Leu Gly Trp Leu Lys Lys His Ala Tyr Cys
        370                 375                 380 tcg aac ctt agt ttc cgc ctg tac gac cag tgg cgt gct tgg atg cag       1321
Ser Asn Leu Ser Phe Arg Leu Tyr Asp Gln Trp Arg Ala Trp Met Gln
    385                 390                 395 aag tca cac aag acc cga aac cag gac gag ggg atc ctg cct tcg ggc       1369
Lys Ser His Lys Thr Arg Asn Gln Asp Glu Gly Ile Leu Pro Ser Gly
400                 405                 410                 415 aga cgg ggt gcg gcg aga ggt cct gcc ggt taaactctaa ggataggcca         1419
Arg Arg Gly Ala Ala Arg Gly Pro Ala Gly
                420                 425 tcctcctgct gggtcagacc tggaggctca cctgaattgg agcccctctg taccatctgg     1479
gcaacaaaga aacctaccag aggctggggc acaatgagct cccacaacca cagctttggt     1539
ccacatgatg gtcacacttg gatataccccc agtgtgggta aggttggggt attgcagggc    1599
ctcccaacaa tctctttaaa taataaagg agttgttcag gtaaaaaaaa aaaaaaaaaa      1659
aaaaaaaaaa aaaa                                                       1673
```

<210> SEQ ID NO 15
<211> LENGTH: 425
<212> TYPE: PRT
<213> ORGANISM: Unknown
<220> FEATURE:
<223> OTHER INFORMATION: Description of Unknown Organism:Murine NR6.2

<400> SEQUENCE: 15

```
Met Pro Ala Gly Arg Gly Pro Val Ala Gln Ser Ala Arg Pro
 1               5                  10                  15

Pro Arg Pro Leu Ser Ser Leu Trp Ser Pro Leu Leu Leu Cys Val Leu
                20                  25                  30

Gly Val Pro Arg Gly Gly Ser Gly Ala His Thr Ala Val Ile Ser Pro
            35                  40                  45

Gln Asp Pro Thr Leu Leu Ile Gly Ser Ser Leu Gln Ala Thr Cys Ser
        50                  55                  60

Ile His Gly Asp Thr Pro Gly Ala Thr Ala Glu Gly Leu Tyr Trp Thr
65                  70                  75                  80

Leu Asn Gly Arg Arg Leu Pro Ser Glu Leu Ser Arg Leu Leu Asn Thr
                85                  90                  95

Ser Thr Leu Ala Leu Ala Leu Ala Asn Leu Asn Gly Ser Arg Gln Gln
            100                 105                 110

Ser Gly Asp Asn Leu Val Cys His Ala Arg Asp Gly Ser Ile Leu Ala
        115                 120                 125

Gly Ser Cys Leu Tyr Val Gly Leu Pro Pro Glu Lys Pro Phe Asn Ile
    130                 135                 140

Ser Cys Trp Ser Arg Asn Met Lys Asp Leu Thr Cys Arg Trp Thr Pro
145                 150                 155                 160
```

```
Gly Ala His Gly Glu Thr Phe Leu His Thr Asn Tyr Ser Leu Lys Tyr
            165                 170                 175
Lys Leu Arg Trp Tyr Gly Gln Asp Asn Thr Cys Glu Glu Tyr His Thr
            180                 185                 190
Val Gly Pro His Ser Cys His Ile Pro Lys Asp Leu Ala Leu Phe Thr
            195                 200                 205
Pro Tyr Glu Ile Trp Val Glu Ala Thr Asn Arg Leu Gly Ser Ala Arg
    210                 215                 220
Ser Asp Val Leu Thr Leu Asp Val Leu Asp Val Val Thr Thr Asp Pro
225                 230                 235                 240
Pro Pro Asp Val His Val Ser Arg Val Gly Leu Glu Asp Gln Leu
            245                 250                 255
Ser Val Arg Trp Val Ser Pro Pro Ala Leu Lys Asp Phe Leu Phe Gln
            260                 265                 270
Ala Lys Tyr Gln Ile Arg Tyr Arg Val Glu Asp Ser Val Asp Trp Lys
            275                 280                 285
Val Val Asp Asp Val Ser Asn Gln Thr Ser Cys Arg Leu Ala Gly Leu
    290                 295                 300
Lys Pro Gly Thr Val Tyr Phe Val Gln Val Arg Cys Asn Pro Phe Gly
305                 310                 315                 320
Ile Tyr Gly Ser Lys Lys Ala Gly Ile Trp Ser Glu Trp Ser His Pro
            325                 330                 335
Thr Ala Ala Ser Thr Pro Arg Ser Glu Arg Pro Gly Pro Gly Gly Gly
            340                 345                 350
Val Cys Glu Pro Arg Gly Gly Glu Pro Ser Ser Gly Pro Val Arg Arg
            355                 360                 365
Glu Leu Lys Gln Phe Leu Gly Trp Leu Lys Lys His Ala Tyr Cys Ser
    370                 375                 380
Asn Leu Ser Phe Arg Leu Tyr Asp Gln Trp Arg Ala Trp Met Gln Lys
385                 390                 395                 400
Ser His Lys Thr Arg Asn Gln Asp Glu Gly Ile Leu Pro Ser Gly Arg
            405                 410                 415
Arg Gly Ala Ala Arg Gly Pro Ala Gly
            420                 425

<210> SEQ ID NO 16
<211> LENGTH: 938
<212> TYPE: DNA
<213> ORGANISM: Unknown
<220> FEATURE:
<221> NAME/KEY: CDS
<222> LOCATION: (1)..(465)
<220> FEATURE:
<223> OTHER INFORMATION: Description of Unknown Organism:Murine NR6.3

<400> SEQUENCE: 16 ggc acc gtt tac ttc gtc caa gtg cgt tgt aac cca ttc ggg atc tat      48
Gly Thr Val Tyr Phe Val Gln Val Arg Cys Asn Pro Phe Gly Ile Tyr
 1               5                  10                  15 ggg tcg aaa aag gcg gga atc tgg agc gag tgg agc cac ccc acc gct      96
Gly Ser Lys Lys Ala Gly Ile Trp Ser Glu Trp Ser His Pro Thr Ala
            20                  25                  30 gcc tcc acc cct cga agt gag cgc ccg ggc ccg ggc ggc ggg gtg tgc     144
Ala Ser Thr Pro Arg Ser Glu Arg Pro Gly Pro Gly Gly Gly Val Cys
        35                  40                  45 gag ccg cgg ggc ggc gag ccc agc tcg ggc ccg gtg cgg cgc gag ctc     192
Glu Pro Arg Gly Gly Glu Pro Ser Ser Gly Pro Val Arg Arg Glu Leu
    50                  55                  60
```

```
            50                  55                   60
aag cag ttc ctc ggc tgg ctc aag aag cac gca tac tgc tcg aac ctt      240
Lys Gln Phe Leu Gly Trp Leu Lys Lys His Ala Tyr Cys Ser Asn Leu
 65              70                   75                   80 agt ttc cgc ctg tac gac cag tgg cgt gct tgg atg cag aag tca cac      288
Ser Phe Arg Leu Tyr Asp Gln Trp Arg Ala Trp Met Gln Lys Ser His
                 85                   90                   95 aag acc cga aac cag gta gga aag ttg ggg gag gct tgc gtg ggg ggt      336
Lys Thr Arg Asn Gln Val Gly Lys Leu Gly Glu Ala Cys Val Gly Gly
                100                  105                  110 aaa gga gca gag gaa gag aga gac ccg ggt gag cag cct cca caa cac      384
Lys Gly Ala Glu Glu Glu Arg Asp Pro Gly Glu Gln Pro Pro Gln His
            115                  120                  125 cgc act ctt ctt tcc aag cac agg acg agg gga tcc tgc cct cgg gca      432
Arg Thr Leu Leu Ser Lys His Arg Thr Arg Gly Ser Cys Pro Arg Ala
        130                  135                  140 gac ggg gtg cgg cga gag gta agg ggg tct ggg tgagtggggc ctacagcagt    485
Asp Gly Val Arg Arg Glu Val Arg Gly Ser Gly
145                 150                  155 ctagatgagg ccctttcccc tccttcggtg ttgctcaaag ggatctctta gtgctcattt    545
cacccactgc aaagagcccc aggttttact gcatcatcaa gttgctgaag ggtccaggct    605
taatgtggcc tcttttctgc cctcaggtcc tgccggctaa actctaagga taggccatcc    665
tcctgctggg tcagacctgg aggctcacct gaattggagc ccctctgtac ctatctgggc    725
aacaaagaaa cctaccatga ggctggggca caatgagctc ccacaaccac agctttggtc    785
cacatgatgg tcacacttgg ataccccca gtgtgggtaa ggttggggta ttgcagggcc     845
tcccaacaat ctctttaaat aaataaagga gttgttcagg taaaaaaaaa aaaaaaaaaa    905
aaaaaaaaaa aaaaaaaaaa aaaaaaaaaa aaa                                 938
```

<210> SEQ ID NO 17
<211> LENGTH: 155
<212> TYPE: PRT
<213> ORGANISM: Unknown
<220> FEATURE:
<223> OTHER INFORMATION: Description of Unknown Organism:Murine NR6.3

<400> SEQUENCE: 17

```
Gly Thr Val Tyr Phe Val Gln Val Arg Cys Asn Pro Phe Gly Ile Tyr
  1               5                  10                  15

Gly Ser Lys Lys Ala Gly Ile Trp Ser Glu Trp Ser His Pro Thr Ala
                 20                  25                  30

Ala Ser Thr Pro Arg Ser Glu Arg Pro Gly Pro Gly Gly Val Cys
             35                  40                  45

Glu Pro Arg Gly Gly Glu Pro Ser Ser Gly Pro Val Arg Arg Glu Leu
         50                  55                  60

Lys Gln Phe Leu Gly Trp Leu Lys Lys His Ala Tyr Cys Ser Asn Leu
 65                  70                  75                  80

Ser Phe Arg Leu Tyr Asp Gln Trp Arg Ala Trp Met Gln Lys Ser His
                 85                  90                  95

Lys Thr Arg Asn Gln Val Gly Lys Leu Gly Glu Ala Cys Val Gly Gly
                100                 105                 110

Lys Gly Ala Glu Glu Glu Arg Asp Pro Gly Glu Gln Pro Pro Gln His
            115                 120                 125

Arg Thr Leu Leu Ser Lys His Arg Thr Arg Gly Ser Cys Pro Arg Ala
        130                 135                 140
```

Asp Gly Val Arg Arg Glu Val Arg Gly Ser Gly
145                 150                 155

<210> SEQ ID NO 18
<211> LENGTH: 834
<212> TYPE: DNA
<213> ORGANISM: Artificial Sequence
<220> FEATURE:
<221> NAME/KEY: CDS
<222> LOCATION: (1)..(834)
<220> FEATURE:
<223> OTHER INFORMATION: Description of Artificial Sequence: Nucleotide
      sequence of products generated by 5' RACE of brain
      cDNA using NR6 specific primers

<400> SEQUENCE: 18

```
ccc acc ctt ctc atc ggc tcc tcc ctg caa gct acc tgc tct ata cat       48
Pro Thr Leu Leu Ile Gly Ser Ser Leu Gln Ala Thr Cys Ser Ile His
 1               5                  10                  15 gga gac aca cct ggg gcc acc gct gag ggg ctc tac tgg acc ctc aat       96
Gly Asp Thr Pro Gly Ala Thr Ala Glu Gly Leu Tyr Trp Thr Leu Asn
             20                  25                  30 ggt cgc cgc ctg ccc tct gag ctg tcc cgc ctc ctt aac acc tcc acc      144
Gly Arg Arg Leu Pro Ser Glu Leu Ser Arg Leu Leu Asn Thr Ser Thr
         35                  40                  45 ctg gcc ctg gcc ctg gct aac ctt aat ggg tcc agg cag cag tca gga      192
Leu Ala Leu Ala Leu Ala Asn Leu Asn Gly Ser Arg Gln Gln Ser Gly
     50                  55                  60 gac aat ctg gtg tgt cac gcc cga gac ggc agc att ctg gct ggc tcc      240
Asp Asn Leu Val Cys His Ala Arg Asp Gly Ser Ile Leu Ala Gly Ser
 65                  70                  75                  80 tgc ctc tat gtt ggc ttg ccc cct gag aag ccc ttt aac atc agc tgc      288
Cys Leu Tyr Val Gly Leu Pro Pro Glu Lys Pro Phe Asn Ile Ser Cys
                 85                  90                  95 tgg tcc cgg aac atg aag gat ctc acg tgc cgc tgg aca ccg ggt gca      336
Trp Ser Arg Asn Met Lys Asp Leu Thr Cys Arg Trp Thr Pro Gly Ala
            100                 105                 110 cac ggg gag aca ttc tta cat acc aac tac tcc ctc aag tac aag ctg      384
His Gly Glu Thr Phe Leu His Thr Asn Tyr Ser Leu Lys Tyr Lys Leu
        115                 120                 125 agg tgg tac ggt cag gat aac aca tgt gag gag tac cac act gtg ggg      432
Arg Trp Tyr Gly Gln Asp Asn Thr Cys Glu Glu Tyr His Thr Val Gly
    130                 135                 140 ccc cac tca tgc cat atc ccc aag gac ctg gcc ctc ttc act ccc tat      480
Pro His Ser Cys His Ile Pro Lys Asp Leu Ala Leu Phe Thr Pro Tyr
145                 150                 155                 160 gag atc tgg gtg gaa gcc acc aat cgc cta ggc tca gca aga tct gat      528
Glu Ile Trp Val Glu Ala Thr Asn Arg Leu Gly Ser Ala Arg Ser Asp
                165                 170                 175 gtc ctc aca ctg gat gtc ctg gac gtg gtg acc acg gac ccc cca ccc      576
Val Leu Thr Leu Asp Val Leu Asp Val Val Thr Thr Asp Pro Pro Pro
            180                 185                 190 gac gtg cac gtg agc cgc gtt ggg ggc ctg gag gac cag ctg agt gtg      624
Asp Val His Val Ser Arg Val Gly Gly Leu Glu Asp Gln Leu Ser Val
        195                 200                 205 cgc tgg gtc tca cca cca gct ctc aag gat ttc ctc ttc caa gcc aag      672
Arg Trp Val Ser Pro Pro Ala Leu Lys Asp Phe Leu Phe Gln Ala Lys
    210                 215                 220 tac cag atc cgc tac cgc gtg gag gac agc gtg gac tgg aag gtg gtg      720
Tyr Gln Ile Arg Tyr Arg Val Glu Asp Ser Val Asp Trp Lys Val Val
225                 230                 235                 240 gat gac gtc agc aac cag acc tcc tgc cgt ctc gcg ggc ctg aag ccc      768
Asp Asp Val Ser Asn Gln Thr Ser Cys Arg Leu Ala Gly Leu Lys Pro
```

-continued

```
Asp Asp Val Ser Asn Gln Thr Ser Cys Arg Leu Ala Gly Leu Lys Pro
            245                 250                 255 ggc acc gtt tac ttc gtc caa gtg cgt tgt aac cca ttc ggg atc tat    816
Gly Thr Val Tyr Phe Val Gln Val Arg Cys Asn Pro Phe Gly Ile Tyr
            260                 265                 270 ggg tcg aaa aag gcg gga                                             834
Gly Ser Lys Lys Ala Gly
            275

<210> SEQ ID NO 19
<211> LENGTH: 278
<212> TYPE: PRT
<213> ORGANISM: Artificial Sequence
<220> FEATURE:
<223> OTHER INFORMATION: Description of Artificial Sequence:
      Haemopoietin receptor

<400> SEQUENCE: 19

Pro Thr Leu Leu Ile Gly Ser Ser Leu Gln Ala Thr Cys Ser Ile His
  1               5                  10                  15

Gly Asp Thr Pro Gly Ala Thr Ala Glu Gly Leu Tyr Trp Thr Leu Asn
             20                  25                  30

Gly Arg Arg Leu Pro Ser Glu Leu Ser Arg Leu Leu Asn Thr Ser Thr
         35                  40                  45

Leu Ala Leu Ala Leu Ala Asn Leu Asn Gly Ser Arg Gln Gln Ser Gly
     50                  55                  60

Asp Asn Leu Val Cys His Ala Arg Asp Gly Ser Ile Leu Ala Gly Ser
 65                  70                  75                  80

Cys Leu Tyr Val Gly Leu Pro Pro Glu Lys Pro Phe Asn Ile Ser Cys
                 85                  90                  95

Trp Ser Arg Asn Met Lys Asp Leu Thr Cys Arg Trp Thr Pro Gly Ala
            100                 105                 110

His Gly Glu Thr Phe Leu His Thr Asn Tyr Ser Leu Lys Tyr Lys Leu
        115                 120                 125

Arg Trp Tyr Gly Gln Asp Asn Thr Cys Glu Glu Tyr His Thr Val Gly
    130                 135                 140

Pro His Ser Cys His Ile Pro Lys Asp Leu Ala Leu Phe Thr Pro Tyr
145                 150                 155                 160

Glu Ile Trp Val Glu Ala Thr Asn Arg Leu Gly Ser Ala Arg Ser Asp
                165                 170                 175

Val Leu Thr Leu Asp Val Leu Asp Val Val Thr Thr Asp Pro Pro Pro
            180                 185                 190

Asp Val His Val Ser Arg Val Gly Gly Leu Glu Asp Gln Leu Ser Val
        195                 200                 205

Arg Trp Val Ser Pro Pro Ala Leu Lys Asp Phe Leu Phe Gln Ala Lys
    210                 215                 220

Tyr Gln Ile Arg Tyr Arg Val Glu Asp Ser Val Asp Trp Lys Val Val
225                 230                 235                 240

Asp Asp Val Ser Asn Gln Thr Ser Cys Arg Leu Ala Gly Leu Lys Pro
                245                 250                 255

Gly Thr Val Tyr Phe Val Gln Val Arg Cys Asn Pro Phe Gly Ile Tyr
            260                 265                 270

Gly Ser Lys Lys Ala Gly
        275

<210> SEQ ID NO 20
<211> LENGTH: 143
```

```
<212> TYPE: DNA
<213> ORGANISM: Artificial Sequence
<220> FEATURE:
<221> NAME/KEY: CDS
<222> LOCATION: (105)..(143)
<220> FEATURE:
<223> OTHER INFORMATION: Description of Artificial Sequence:Nucleotide
      sequence unique to 5' RACE of brain cDNA

<400> SEQUENCE: 20
ggcatgaagg cttagggtgg ggatcggtag gacccatgca cccagagaaa gggactggtg    60
gcaactttca aactctctgg ggaaggaaga agggctgaaa gagg atg aac ggg ctc   116
                                                Met Asn Gly Leu
                                                  1 aga cac agc tgt aat cag ccc cca gga                                 143
Arg His Ser Cys Asn Gln Pro Pro Gly
  5                  10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Amino Acid
      Sequence encoded by Nucleotide sequence unique to 5' RACE of brain
      cDNA

<400> SEQUENCE: 21

Met Asn Gly Leu Arg His Ser Cys Asn Gln Pro Pro Gly
  1               5                  10

<210> SEQ ID NO 22
<211> LENGTH: 1930
<212> TYPE: DNA
<213> ORGANISM: Unknown
<220> FEATURE:
<223> OTHER INFORMATION: Description of Unknown Organism:Murine NR6

<400> SEQUENCE: 22
ggcacgagct tcgctgtccg cgcccagtga cgcgcgtgcg gacccgagcc ccaatctgca    60
ccccgcagac tcgcccccgc cccataccgg cgttgcagtc accgcccgtt gcgcgccacc   120
cccaatgccc gcgggtcgcc cgggcccccgt cgcccaatcc gcgcggcggc cgccgcggcc   180
gctgtcctcg ctgtggtcgc ctctgttgct ctgtgtcctc ggggtgcctc ggggcggatc   240
gggagcccac acagctgtaa tcagccccca ggacccccacc cttctcatcg gctcctccct   300
gcaagctacc tgctctatac atggagacac acctggggcc accgctgagg ggctctactg   360
gaccctcaat ggtcgccgcc tgccctctga gctgtcccgc ctccttaaca cctccaccct   420
ggccctggcc ctggctaacc ttaatgggtc caggcagcag tcaggagaca atctggtgtg   480
tcacgcccga gacggcagca ttctggctgg ctcctgcctc tatgttggct tgccccctga   540
gaagcccttt aacatcagct gctggtcccg gaacatgaag gatctcacgt gccgctggac   600
accgggtgca cacggggaga cattcttaca taccaactac tccctcaagt acaagctgag   660
gtggtacggt caggataaca catgtgagga gtaccacact gtgggccctc actcatgcca   720
tatccccaag gacctggccc tcttcactcc ctatgagatc tgggtggaag ccaccaatcg   780
cctaggctca gcaagatctg atgtcctcac actggatgtc ctggacgtgg tgaccacgga   840 cccccccaccc gacgtgcacg tgagccgcgt tggggggcctg gaggaccagc tgagtgtgcg   900
ctgggtctca ccaccagctc tcaaggattt cctcttccaa gccaagtacc agatccgcta   960
ccgcgtggag gacagcgtgg actggaaggt ggtggatgac gtcagcaacc agaccctcctg  1020
```

```
ccgtctcgcg ggcctgaagc ccggcaccgt ttacttcgtc caagtgcgtt gtaacccatt    1080
cgggatctat gggtcgaaaa aggcgggaat ctggagcgag tggagccacc ccaccgctgc    1140 ctccaccoct cgaagtgagc gcccgggccc ggcggcggg gtgtgcgagc cgcggggcgg    1200
cgagcccagc tcgggcccgg tgcggcgcga gctcaagcag ttcctcggct ggctcaagaa    1260
gcacgcatac tgctcgaacc ttagtttccg cctgtacgac cagtggcgtg cttggatgca    1320
gaagtcacac aagacccgaa accaggtagg aaagttgggg gaggcttgcg tgggggtaa    1380 aggagcagag gaagagagag acccgggtga gcagcctcca caacaccgca ctcttctttc    1440
caagcacagg acgaggggat cctgccctcg ggcagacggg gtgcggcgag aggtaagggg    1500
gtctgggtga gtggggccta cagcagtcta gatgaggccc tttcccctcc ttcggtgttg    1560
ctcaaaggga tctcttagtg ctcatttcac ccactgcaaa gagcccagg ttttactgca     1620 tcatcaagtt gctgaagggt ccaggcttaa tgtggcctct tttctgccct caggtcctgc    1680 cggctaaaact ctaaggatag gccatcctcc tgctgggtca gacctggagg ctcacctgaa   1740
ttggagcccc tctgtaccta tctgggcaac aaagaaacct accatgaggc tggggcacaa    1800
tgagctccca caaccacagc tttggtccac atgatggtca cacttggata taccccagtg    1860
tgggtaaggt tggggtattg cagggcctcc caacaatctc tttaaataaa taaggagtt    1920 gttcaggtaa                                                           1930

<210> SEQ ID NO 23
<211> LENGTH: 560
<212> TYPE: DNA
<213> ORGANISM: Artificial Sequence
<220> FEATURE:
<223> OTHER INFORMATION: Description of Artificial Sequence:PCR product
      for human NR6

<400> SEQUENCE: 23
tccaggcagc ggtcggggga caacctcgtg tgccacgccc gtgacggcag catcctggct      60
ggctcctgcc tctatgttgg cctgccccca gagaaacccg tcaacatcag ctgctggtcc    120
aagaacatga aggacttgac ctgccgctgg acgccagggg cccacgggga gaccttcctc    180
cacaccaact actccctcaa gtacaagctt aggtggtatg ccaggacaa cacatgtgag    240 gagtaccaca cagtggggcc ccactcctgc acatccccca aggacctggc tctctttacg    300
ccctatgaga tctgggtgga ggccaccaac cgcctgggct ctgcccgctc cgatgtactc    360
acgctggata tcctggatgt ggtgaccacg gaccccccgc ccgacgtgca cgtgagccgc    420
gtcgggggcc tggaggacca gctgagcgtg cgctgggtgt cgccaccgc cctcaaggat    480 ttccttttc aagccaaata ccagatccgc taccgagtgg aggacagtgt ggaatggaag    540
gtggtggacg atgtgagcaa                                                560

<210> SEQ ID NO 24
<211> LENGTH: 1391
<212> TYPE: DNA
<213> ORGANISM: Unknown
<220> FEATURE:
<221> NAME/KEY: CDS
<222> LOCATION: (1)..(1050)
<220> FEATURE:
<223> OTHER INFORMATION: Description of Unknown Organism:Nucleotide
      sequence of clone HFK-66 encoding human NR6

<400> SEQUENCE: 24 acc ctc aac ggg cgc cgc ctg ccc cct gag ctc tcc cgt gta ctc aac        48
```

```
                Thr Leu Asn Gly Arg Arg Leu Pro Pro Glu Leu Ser Arg Val Leu Asn
                  1               5                  10                  15 gcc tcc acc ttg gct ctg gcc ctg gcc aac ctc aat ggg tcc agg cag                96
Ala Ser Thr Leu Ala Leu Ala Leu Ala Asn Leu Asn Gly Ser Arg Gln
             20                  25                  30 cgg tcg ggg gac aac ctc gtg tgc cac gcc cgt gac ggc agc atc ctg              144
Arg Ser Gly Asp Asn Leu Val Cys His Ala Arg Asp Gly Ser Ile Leu
         35                  40                  45 gct ggc tcc tgc ctc tat gtt ggc ctg ccc cca gag aaa ccc gtc aac              192
Ala Gly Ser Cys Leu Tyr Val Gly Leu Pro Pro Glu Lys Pro Val Asn
     50                  55                  60 atc agc tgc tgg tcc aag aac atg aag gac ttg acc tgc cgc tgg acg              240
Ile Ser Cys Trp Ser Lys Asn Met Lys Asp Leu Thr Cys Arg Trp Thr
 65                  70                  75                  80 cca ggg gcc cac ggg gag acc ttc ctc cac acc aac tac tcc ctc aag              288
Pro Gly Ala His Gly Glu Thr Phe Leu His Thr Asn Tyr Ser Leu Lys
                 85                  90                  95 tac aag ctt agg tgg tat ggc cag gac aac aca tgt gag gag tac cac              336
Tyr Lys Leu Arg Trp Tyr Gly Gln Asp Asn Thr Cys Glu Glu Tyr His
             100                 105                 110 aca gtg ggg ccc cac tcc tgc cac atc ccc aag gac ctg gct ctc ttt              384
Thr Val Gly Pro His Ser Cys His Ile Pro Lys Asp Leu Ala Leu Phe
         115                 120                 125 acg ccc tat gag atc tgg gtg gag gcc acc aac cgc ctg ggc tct gcc              432
Thr Pro Tyr Glu Ile Trp Val Glu Ala Thr Asn Arg Leu Gly Ser Ala
     130                 135                 140 cgc tcc gat gta ctc acg ctg gat atc ctg gat gtg gtg acc acg gac              480
Arg Ser Asp Val Leu Thr Leu Asp Ile Leu Asp Val Val Thr Thr Asp
145                 150                 155                 160 ccc ccg ccc gac gtg cac gtg agc cgc gtc ggg ggc ctg gag gac cag              528
Pro Pro Pro Asp Val His Val Ser Arg Val Gly Gly Leu Glu Asp Gln
                 165                 170                 175 ctg agc gtg cgc tgg gtg tcg cca ccc gcc ctc aag gat ttc ctc ttt              576
Leu Ser Val Arg Trp Val Ser Pro Pro Ala Leu Lys Asp Phe Leu Phe
             180                 185                 190 caa gcc aaa tac cag atc cgc tac cga gtg gag gac agt gtg gac tgg              624
Gln Ala Lys Tyr Gln Ile Arg Tyr Arg Val Glu Asp Ser Val Asp Trp
         195                 200                 205 aag gtg gtg gac gat gtg agc aac cag acc tcc tgc cgc ctg gcc ggc              672
Lys Val Val Asp Asp Val Ser Asn Gln Thr Ser Cys Arg Leu Ala Gly
     210                 215                 220 ctg aaa ccc ggc acc gtg tac ttc gtg caa gtg cgc tgc aac ccc ttt              720
Leu Lys Pro Gly Thr Val Tyr Phe Val Gln Val Arg Cys Asn Pro Phe
225                 230                 235                 240 ggc atc tat ggc tcc aag aaa gcc ggg atc tgg agt gag tgg agc cac              768
Gly Ile Tyr Gly Ser Lys Lys Ala Gly Ile Trp Ser Glu Trp Ser His
                 245                 250                 255 ccc aca gcc gcc tcc act ccc cgc agt gag cgc ccg ggc ccg ggc ggc              816
Pro Thr Ala Ala Ser Thr Pro Arg Ser Glu Arg Pro Gly Pro Gly Gly
             260                 265                 270 ggg gcg tgc gaa ccg cgg ggc gga gag ccg agc tcg ggg ccg gtg cgg              864
Gly Ala Cys Glu Pro Arg Gly Gly Glu Pro Ser Ser Gly Pro Val Arg
         275                 280                 285 cgc gag ctc aag cag ttc ctg ggc tgg ctc aag aag cac gcg tac tgc              912
Arg Glu Leu Lys Gln Phe Leu Gly Trp Leu Lys Lys His Ala Tyr Cys
     290                 295                 300 tcc aac ctc agc ttc cgc ctc tac gac cag tgg cga gcc tgg atg cag              960
Ser Asn Leu Ser Phe Arg Leu Tyr Asp Gln Trp Arg Ala Trp Met Gln
305                 310                 315                 320
```

-continued

```
aag tcg cac aag acc cgc aac cag cac agg acg agg gga tcc tgc cct     1008
Lys Ser His Lys Thr Arg Asn Gln His Arg Thr Arg Gly Ser Cys Pro
            325                 330                 335 cgg gca gac ggg gca cgg cga gag gtc ctg cca gat aag ctg             1050
Arg Ala Asp Gly Ala Arg Arg Glu Val Leu Pro Asp Lys Leu
        340                 345                 350 tagggctca ggccaccctc cctgccacgt ggagacgcag aggccgaacc caaactgggg    1110
ccacctctgt accctcactt cagggcacct gagcccctca gcaggagctg ggtggcccc    1170 tgagctccaa cggccataac agctctgact cccacgtgag gccacctttg ggtgcacccc   1230
agtgggtgtg tgtgtgtgtg tgagggttgg ttgagttgcc tagaacccct gccagggctg   1290
ggggtgagaa ggggagtcat tactccccat tacctagggc ccctccaaaa gagtccttt    1350 aaataaatga gctatttagg tgcaaaaaaa aaaaaaaaaa a                       1391
```

<210> SEQ ID NO 25
<211> LENGTH: 350
<212> TYPE: PRT
<213> ORGANISM: Unknown
<220> FEATURE:
<223> OTHER INFORMATION: Description of Unknown Organism: Haemopoietin receptor

<400> SEQUENCE: 25

```
Thr Leu Asn Gly Arg Arg Leu Pro Pro Glu Leu Ser Arg Val Leu Asn
  1               5                  10                  15

Ala Ser Thr Leu Ala Leu Ala Leu Ala Asn Leu Asn Gly Ser Arg Gln
             20                  25                  30

Arg Ser Gly Asp Asn Leu Val Cys His Ala Arg Asp Gly Ser Ile Leu
         35                  40                  45

Ala Gly Ser Cys Leu Tyr Val Gly Leu Pro Pro Glu Lys Pro Val Asn
     50                  55                  60

Ile Ser Cys Trp Ser Lys Asn Met Lys Asp Leu Thr Cys Arg Trp Thr
 65                  70                  75                  80

Pro Gly Ala His Gly Glu Thr Phe Leu His Thr Asn Tyr Ser Leu Lys
                 85                  90                  95

Tyr Lys Leu Arg Trp Tyr Gly Gln Asp Asn Thr Cys Glu Glu Tyr His
            100                 105                 110

Thr Val Gly Pro His Ser Cys His Ile Pro Lys Asp Leu Ala Leu Phe
        115                 120                 125

Thr Pro Tyr Glu Ile Trp Val Glu Ala Thr Asn Arg Leu Gly Ser Ala
    130                 135                 140

Arg Ser Asp Val Leu Thr Leu Asp Ile Leu Asp Val Val Thr Thr Asp
145                 150                 155                 160

Pro Pro Pro Asp Val His Val Ser Arg Val Gly Gly Leu Glu Asp Gln
                165                 170                 175

Leu Ser Val Arg Trp Val Ser Pro Pro Ala Leu Lys Asp Phe Leu Phe
            180                 185                 190

Gln Ala Lys Tyr Gln Ile Arg Tyr Arg Val Glu Asp Ser Val Asp Trp
        195                 200                 205

Lys Val Val Asp Asp Val Ser Asn Gln Thr Ser Cys Arg Leu Ala Gly
    210                 215                 220

Leu Lys Pro Gly Thr Val Tyr Phe Val Gln Val Arg Cys Asn Pro Phe
225                 230                 235                 240

Gly Ile Tyr Gly Ser Lys Lys Ala Gly Ile Trp Ser Glu Trp Ser His
                245                 250                 255
```

```
Pro Thr Ala Ala Ser Thr Pro Arg Ser Glu Arg Pro Gly Gly
                260                 265                 270
Gly Ala Cys Glu Pro Arg Gly Gly Glu Pro Ser Ser Gly Pro Val Arg
            275                 280                 285
Arg Glu Leu Lys Gln Phe Leu Gly Trp Leu Lys Lys His Ala Tyr Cys
        290                 295                 300
Ser Asn Leu Ser Phe Arg Leu Tyr Asp Gln Trp Arg Ala Trp Met Gln
305                 310                 315                 320
Lys Ser His Lys Thr Arg Asn Gln His Arg Thr Arg Gly Ser Cys Pro
                325                 330                 335
Arg Ala Asp Gly Ala Arg Arg Glu Val Leu Pro Asp Lys Leu
            340                 345                 350

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:UP1
      Oligonucleotide

<400> SEQUENCE: 26
tccaggcagc ggtcggggga caac                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:LP1
      Oligonucleotide

<400> SEQUENCE: 27
ttgctcacat cgtccaccac cttc                                              24

<210> SEQ ID NO 28
<211> LENGTH: 6663
<212> TYPE: DNA
<213> ORGANISM: Unknown
<220> FEATURE:
<223> OTHER INFORMATION: Description of Unknown Organism:Murine NR6 gene

<400> SEQUENCE: 28
cccagaactc ttggacgctg aggcaggagg attcccaagt ttcaagacag tgtgtttcta       60
ggtaatgaga ccctgtcaag aaaagaaaag aaataaagag acaagaaaat gtttataggc      120
tgtgagacag cttggtgggt aaggggcact tgcctccaat caagatgacc tcagccccat      180
ccctaggaat ccatggtaga aggagaaagc aaactcgcag ctgctgacct ccatacatgt      240
gctccaatgt gcacacacac agggagacat aatcaattaa taggatgtat ttgcttagat      300
ttgagtaggc atttatgact gatgttttaa aattttttatt tgattttatg aaaatatacc     360
tgtttgtatt tggtttggtt tggtttgagt tttgtttatt tgagacaggg cttctctgtg      420
tagtcctggc tgtccttgga actcactctg tagaccaggc tggccttgaa ctcagaaatc      480
cgcctgcttg tgcttcccaa gtgcttagat taaggtgtg cactgccatt cagcaaaatt       540
gcatacttta accccagtat ttgggaggca gaggcagact aatgtgtgaa ttccaggcta      600
gccaaggata cagagtgaga ccctattctt accctccccc cccaaaaccc caaaatgtat      660
tttgtgcttg tgtatgtaca tgtgtgttgc agcacgtaaa tgtccaagga caacttgtag      720
aagttctctc cgttcacagt ctaagtcctg aattcaaact aaggtcctca ggcttagcca      780
```

```
cagtcttctt tatgtactga gccatttcac tggccctgga ttgactgatg aattaattt       840 tgagataagg tctcttgtag ctctagctag gctcaaacta tgaactccca aggtcatctt      900
gagctgctgg tactcttgct tccaccccaa gtggtggaat gatactcagg cagcacttct      960
ctggggaagg ggctggcctt ggccttgatt tgttgcctc agcttcaatg agtgcttggg      1020
tctcgttgtt tcttttcttt atctgtgaaa tgggtgaaca cctgttcaag acttcctgac     1080
tcttgaaaca tccaggcagg gtgagggact tgaagtgggc tcatcccatg cctaacaaag     1140
tgtcgtcttt gacccagac acagctgtaa tcagccccca ggaccccacc cttctcatcg      1200
gctcctccct gcaagctacc tgctctatac atggagacac acctggggcc accgctgagg     1260
ggctctactg gaccttcaat ggtcgccgcc tgccctctga gctgtcccgc ctccttaaca     1320
cctccaccct ggccctggcc ctggctaacc ttaatgggtc caggcagcag tcaggagaca     1380
atctggtgtg tcacgcccga gacggcagca ttctggctgg ctcctgcctc tatgttggct     1440
gtaagtgggg ccccagacac tcagagatag atggggttg gcaatgacag atttagagcc      1500
tgggtcttct gtcctgggc agagccatgg gctctcactt gcatgcaggc atggtcatac      1560
ccagcacagg cattgcaact ctagggacag ctgtggctgc actgtcccct gtgtaccca     1620 cagctttaga aaagctgtca tgtttcctt gtagtgcccc ctgagaagcc ctttaacatc     1680
agctgctggt cccggaacat gaaggatctc acgtgccgct ggacaccggg tgcacacggg     1740
gagacattct tacataccaa ctactccctc aagtacaagc tgaggttggt acccagccaa     1800
gccttgctgt gtgacttctg caatactta ccttctctga tcaaatatgt tcctgtttat      1860
gaactcaaaa gggactctcg cacctccaca ggtggtacgg tcaggataac acatgtgagg     1920
agtaccacac tgtgggccct cactcatgcc atatccccaa ggacctggcc ctcttcactc     1980
cctatgagat ctgggtggaa gccaccaatc gcctaggctc agcaagatct gatgtcctca     2040
cactggatgt cctggacgtg ggtgagcccc cagtgtccac ctgtgttctg ccctagacct     2100
tatagggcgc ctcccccca tccccccaga cttttttggtt cttctagagg tcttagccac     2160
agccacggtg gttgcaggac agtggttgtt cataacttaa tgcaaagact ttccccaag     2220 acagtcaaga tttttcccct ccccaccccc aacacacaca tacacacaca ctctgcagag     2280
aacacctggc ctgaccaccc tccctctcta cagcccaggt gttcagaagg gagtcctagg     2340
ggactgagag gaggcgccca ggtctgaagg cgccccagga agccgaggcc ttgagctggg     2400
ggggggggcg agggttggag gcacgaactg gatgatccct gagcacaact gggcctaatc     2460
taattagggt gttcccagcc caaagcagcc tgggccattt aacccttcaa gtgcctcact     2520
gaagactcag gggagagatc agcttgtact ctctccatgg tcccccagga gggttcctgg     2580
gtgcccctgg ctcattccca catccagagg ttttgtgtct tcctggcatc taaccctcag     2640
ttgtgctctg tggctggcac agctgccccg tggaggctct tggtaatgta caaggcatca     2700
gaggtggaca tgggatgggg atacataggg atggagccaa atagcacctc aaggtgggt      2760 gatatacaat aaagcttgtc accctgacgc tcagaaagcc tactcatgat gatcacaatt     2820
gttgacatca ctctgggaca tgtagtgaga ccctagctca aaacacagac agtagcttta     2880
agagtcagct tgtgacttaa tactggaact cagggcctaa taggtgctgg gtgatgctcg     2940
cctcactccc tgtttagaga gatctctgcg ctaatctcca cccagctgg gtgggctgct     3000 ctgtccccct gagggcagga atgtgtgtct tccatcagag ataggacccg tggtagcagc     3060
aactgctgct ggctgtttct ggaatattaa atgacagtaa tctatcaggc ctgggtgagt     3120
```

```
agctaacagg ggtgggggcg tggtctggaa aacgcagata gggtcatagg agccactgca    3180
gcctagatta caccactggg tgttctgtca ctaggccatt ctcaccaagc agtcctcaga    3240
actgggagca ctgttgccag catttaatgc cagcatttaa tgccagcatt agggaggca    3300 gaggcagaag gatctctctg agttcaaggc catcctgaat ttacataaag agctccaggc    3360
cagccagggt gcgcagtaaa accttgtctc aaaaaacaaa gcatctttag tgaccaggct    3420
tgctccaccc ccagtgacca cggaccccc acccgacgtg cacgtgagcc gcgttggggg    3480
cctggaggac cagctgagtg tgcgctgggt ctcaccacca gctctcaagg atttcctctt    3540
ccaagccaag taccagatcc gctaccgcgt ggaggacagc gtggactgga aggtgcccgt    3600
cccgccccgg acccgcccct gaccccgccc ccgcatctg actcctccct caccgtgcag    3660
gtggtggatg acgtcagcaa ccagacctcc tgccgtctcg cgggcctgaa gcccggcacc    3720
gtttacttcg tccaagtgcg ttgtaaccca ttcgggatct atgggtcgaa aaaggcggga    3780
atctggagcg agtggagcca ccccaccgct gcctccaccc ctcgaagtgg tgagcacctc    3840
tccagggctg gctggcccat ggaatcccca atccatcctg ttccttcccc cccacccttt    3900
ttttgagaca gcgtcttcag gtagcgcatg ctggccttaa attcagtatg tagtcaagga    3960
tgacctcgag ctcctggtct ttttgtctcc acttagagac aatggccagt ggccatcacc    4020
acctttggga gactagccat ggagtctatt tagcctgtca tttggtgaca gatggagtac    4080
aacagtgtga cctcttgtaa gagaactgaa gacaggctgt ttttaacccc aatatcctag    4140
gctctctaga ggttaacttt atataaaata gagactatta cagccagtta tcacatggtc    4200
ccacagaacc ttttgtcaca caacctatag accacagtgc ctgtgcctac cacataaggg    4260
tctctactgc tggcccaccc ctccaaccct taaaaggtaa cctaggcagc cttaatattt    4320
gcaatcctcc tacctcagcc tcttgaatgc tcagaaacca ggcattaacc caagtttctc    4380
ttctctgggt ccctttctta aggtgggagg gcctaaagat gacttccttt gtcctgaaga    4440
ctctccgagc ccatggatct gcactctcta atatgaaata tattgcataa aatgtctggc    4500
ctcagtttcc ccacctgtca ggtttaggca gcacagtcgg tccaagacac ttcattattt    4560
gcaggcagta taagaagaag ctcccatccc ccacccgctt cctccggtcc ctaagacaga    4620
atacttctac actgaaactg aactctcgca gacgcatatg ctcactttaa tgatgatgaa    4680
ataatgggga aactgaggct ccgagagatt cctggaggaa gagggtcaaa accagctcca    4740
ggaagctctc cagcccccat ccgggcctct ccaggttctg ggcttggcgg gagtgaacac    4800
agctgggagg ggctggagcc tgggagcttt ggccttgct cgtgcccagc acctgcgatt    4860
cttgcacggg agccagcagg cggctgcgtc cgcccgagag actgaagaag ccggggtag    4920 ggttggaggg aggtaagcag gggctgtggg ggccgaagct tgtgccaggg cctgtcagcg    4980
agtccccagt tttatttatg gcgtgaggcc gatgtcctta ccgctggcc tgctggggga    5040 tggctgcggc tggggattgg acccaagggc tggcttccca ctcagtcctc cagcccactc    5100
catgtcacac ccgtgcattc tctgaggctt atcttgggaa cccgcccttg ttctgtgctg    5160
tctgtctcta tttctgtcat tcactttccc agagcctttt ttttatgctt ttaatataac    5220
tacgttttaa aaattgcttt tgtataatgt gtgtgccttc gtgagcgtgc gtgccacaac    5280
acacacgtga aggttagaga actttgttga gtaggctcct tccaccatgt gggactaggg    5340
ctggcgacaa gagcaattac tgagtcatct cgccagcccc tcaccctca cttcccatcc    5400 tgtttgata gtcataggta atcgaaggta aatcgctggc tttaatttcg tagctatcct    5460
gcctcagcct accaagtgct gtgctaccac gtttgtggga ggggctctcc tcccagtgtc    5520
```

-continued

```
tgggggtgac acagtcccaa gatctctgct ttctaggtct ttgtcttagt ttgccccttg    5580
ctttgtccgt gtccctagag tctccggccc cacttatcca ttgactggtc tttcctttac    5640
cgaatactcg gttttacctc ccactgattt gactccctcc tttgcttgtc tccatcgccg    5700
tggcattgcc attcctctgg gtgactctgg gtccacacct gacaccttc ccaactttcc     5760 ccagccgaag ctggtctggt atgggaggcc gccgtcccgc gcgcgcctcc tgctggccgc    5820
gccccaacac tgccgctcca ttctctttag agcgcccggg cccggcggc ggggtgtgcg     5880 agccgcgggg cggcgagccc agctcggcc cggtgcggcg cgagctcaag cagttcctcg     5940
gctggctcaa gaagcacgca tactgctcga accttagttt ccgcctgtac gaccagtggc    6000
gtgcttggat gcagaagtca cacaagaccc gaaaccaggt aggaaagttg ggggaggctt    6060
gcgtgggggg taaaggagca gaggaagaga gagacccggg tgagcagcct ccacaacacc    6120
gcactcttct ttccaagcac aggacgaggg gatcctgccc tcgggcagac ggggtgcggc    6180
gagaggtaag ggggtctggg tgagtggggc ctacagcagt ctagatgagg ccctttcccc    6240
tccttcggtg ttgctcaaag ggatctctta gtgctcattt cacccactgc aaagagcccc    6300
aggttttact gcatcatcaa gttgctgaag ggtccaggct taatgtggcc tcttttctgc    6360
cctcaggtcc tgccggctaa actctaagga taggccatcc tcctgctggg tcagacctgg    6420
aggctcacct gaattggagc ccctctgtac catctgggca acaaagaaac ctaccagagg    6480
ctgggcacaa tgagctccca caaccacagc tttggtccac atgatggtca cacttggata    6540
taccccagtg tgggtagggt tggggtattg cagggcctcc caagagtctc tttaaataaa    6600
taaaggagtt gttcaggtcc cgatggccag tgtgtttggg gcctatgtgc tggggtgggg    6660
gga                                                                  6663
```

<210> SEQ ID NO 29
<211> LENGTH: 186
<212> TYPE: PRT
<213> ORGANISM: Unknown
<220> FEATURE:
<223> OTHER INFORMATION: Description of Unknown Organism:Murine NR6
<220> FEATURE:
<221> NAME/KEY: UNSURE
<222> LOCATION: (136)
<223> OTHER INFORMATION: Unsure at position 136
<220> FEATURE:
<221> NAME/KEY: UNSURE
<222> LOCATION: (139)
<223> OTHER INFORMATION: Unsure at positionn 139
<220> FEATURE:
<221> NAME/KEY: UNSURE
<222> LOCATION: (162)
<223> OTHER INFORMATION: Unsure at position 162
<220> FEATURE:
<221> NAME/KEY: UNSURE
<222> LOCATION: (177)
<223> OTHER INFORMATION: Unsure at position 177

<400> SEQUENCE: 29

```
Asp Pro Thr Leu Leu Ile Gly Ser Ser Leu Gln Ala Thr Cys Ser Ile
 1               5                  10                  15

His Gly Asp Thr Pro Gly Ala Thr Ala Glu Gly Leu Tyr Trp Thr Phe
            20                  25                  30

Asn Gly Arg Arg Leu Pro Ser Glu Leu Ser Arg Leu Leu Asn Thr Ser
        35                  40                  45

Thr Leu Ala Leu Ala Leu Ala Asn Leu Asn Gly Ser Arg Gln Gln Ser
    50                  55                  60
```

```
Gly Asp Asn Leu Val Cys His Ala Arg Asp Gly Ser Ile Leu Ala Gly
 65                  70                  75                  80

Ser Cys Leu Tyr Val Gly Leu Pro Pro Glu Lys Pro Phe Asn Ile Ser
                 85                  90                  95

Cys Trp Ser Arg Asn Met Lys Asp Leu Thr Cys Arg Trp Thr Pro Gly
            100                 105                 110

Ala His Gly Glu Thr Phe Leu His Thr Asn Tyr Ser Leu Lys Tyr Lys
        115                 120                 125

Leu Arg Leu Val Arg Ser Glu Xaa His Met Xaa Gly Val Pro His Cys
    130                 135                 140

Glu Pro Ser Leu Met Pro Tyr Pro Gln Gly Pro Gly Pro Leu His Ser
145                 150                 155                 160

Leu Xaa Asp Leu Gly Gly Ser His Gln Ser Pro Arg Leu Ser Lys Ile
                165                 170                 175

Xaa Cys Pro His Thr Gly Cys Pro Gly Arg
                180                 185
```

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence:Murine 5'
      UTR

<400> SEQUENCE: 30
agctggcgcg cctcccgggc ggatcgggag cccac                              35

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence:Murine 3'
      UTR

<400> SEQUENCE: 31
agctacgcgt ttagagttta gccggcag                                      28

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence:Murine IL-3

<400> SEQUENCE: 32

```
Met Val Leu Ala Ser Ser Thr Thr Ser Ile His Thr Met Leu Leu Leu
  1               5                  10                  15

Leu Leu Met Leu Phe His Leu Gly Leu Gln Ala Ser Ile Ser
                 20                  25                  30
```

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence:3' UTR

<400> SEQUENCE: 33

```
Ile Lys Pro Ser Gly Arg Arg Gly Ala Ala Arg Gly Pro Ala Gly Asp
  1               5                  10                  15
```

Tyr Lys Asp Asp Asp Asp Lys
            20

<210> SEQ ID NO 34
<211> LENGTH: 73
<212> TYPE: DNA
<213> ORGANISM: Artificial Sequence
<220> FEATURE:
<223> OTHER INFORMATION: Description of Artificial Sequence:3' UTR

<400> SEQUENCE: 34
gatcttgccc tcgggcagac ggggtgcggc gagaggtcct gccggcgact acaaggacga        60
cgatgacaag tag                                                          73

<210> SEQ ID NO 35
<211> LENGTH: 73
<212> TYPE: DNA
<213> ORGANISM: Artificial Sequence
<220> FEATURE:
<223> OTHER INFORMATION: Description of Artificial Sequence:3' UTR

<400> SEQUENCE: 35
aacgggagcc cgtctgcccc acgccgctct ccaggacggc cgctgatgtt cctgctgcta        60
ctgttcatcc tag                                                          73

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide 2199

<400> SEQUENCE: 36
cccacgcttc tcatcggatt ctccctg                                           27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide 2200

<400> SEQUENCE: 37
cagtccacac tgtcctccac tcggtag                                           27

<210> SEQ ID NO 38
<211> LENGTH: 11832
<212> TYPE: DNA
<213> ORGANISM: Unknown
<220> FEATURE:
<223> OTHER INFORMATION: Description of Unknown Organism:Murine NR6 gene

<400> SEQUENCE: 38
gcggccgctg cagtgattac tcaccgcgtg gcgcacccca cccgcgggcc gctgagtgga        60
tttttccgtg gggggatgtg aagaagttta gggagaactc ttctgcaccg atgggaacta       120
ggaatgcagg gttcggtccc gttccccaaa ggacacacct ctcccataa gcccactcat        180 aagggctccc tgcacgcgct ccgggacatc cccatatcca atacccgcag atatgatagt       240
tgagaaggga ccagaggccg gagactccct ccctgccttc tggctttccc ccccccctgc       300
acgaaacgag actacagcga tgggagaggt ggcatgaagg cttagggtgg ggatcggtag       360

-continued

```
gacccatgca cccagagaaa gggactggtg gcaactttca aactctctgg ggaaggaaga       420
agggctgaaa gaggatgaac gggctcaggt actgctcaat gtgtgtgtgg cggaccaaag       480
tgggtatggg ggccccgtaa gaggggcggg gaaggtggat aggaaggatc ccggtagact       540 ggagggatc ctggaaaagc accagggctg cgagctagga acccattcgg agttaagggt       600
acaggatccc agatgagggg gtgggaagcc tgggacgggc gggaccagag agggaggtcc       660
cacgggctgg tggggaaaga gtgggggct tcgcgcagga ggatgggacg ttcaggagtg        720
gtaactgggc ggaggccggc cgggcggggc gcgcggtgcc cgcgggcggt gggaaggccg       780
gtgcggggcc cacgatcaac cccccccag gggccgggcc gggccggggg cggggccggg        840
cggggcgagc ggcgcattag cgccttgtca atttcggctg ctcagacttg ctccggcctt       900
cgctgtccgc gcccagtgac gcgcgtgagg acccgagccc caatctgcac cccgcagact       960
cgcccccgcc ccataccggc gttgcagtca ccgcccgttg cgcgccaccc ccatgcccgc       1020
gggtcgcccg ggccccgtcg cccaatccgc gcggcggccg ccgcggccgc tgtcctcgct       1080
gtggtcgcct ctgttgctct gtgtcctcgg ggtgcctcgg ggcggatcgg gagcccgtga       1140
gtaccgtgcg ccctgctccc cacctcccca gggaagccgg gatccggcgc cccgggggt       1200 agtcgcgggg gatggaagaa ggggcgcgag cgccacctgg acgtcccggg aacaaaggaa       1260
ggcggccctc ggggcgccct cacctgtggg gctcatggca ccaccaccca gcctcccaag       1320
agtaccccgt tatacatcag aggcctctta tctgtatccc ctttgcgagg ctgtctggcc       1380
aggctcagtt tgaaggacat cgcagtgtcc tgggaccccc ctccttcagg gtgctgggac       1440
gcttcggggc gcacgcctgt gtcttggata tcagagcgga agggaagcct ccctggccgg       1500
gggcgcacgc ttgggtgcgt tgggttgggt gctggcgcaa agtgggggtcc cctcccccat       1560 gaagtgatga tccccggggg gagggtgggg cgttatcgtg agccctcctg tccgcctggc       1620
atgcggcccg gcgtccctcg ggacttgcct ctccgtgggg tcggcgccgc cccctccccc       1680
ctatagcaga ctccatgctt tggtatcctc gaagtcctct ccactggtgg ggctcacaac       1740
cggtctcatt caggctgcgc tgggttgaga gcctctagcg actgaaattt cggtgaggag       1800
cgagagcaag cgtgtccggg caccgcgagc ccagacttca ttgtctaagg ggcacccagt       1860
gggggtcagc tgccgagaga atcccactgt cccaggagga actcctggcc ttgagccccc       1920
atcacccaac gcacacatcc ccgccaggat gcggtctcca catccagacc ctctctggga      1980
cacacccaaa gacacacaaa agagccccac tggcttatgt cccgtcaccc tgccctccga      2040
cgcgcgctgc agcccagatg cgtattcgca caccatcgcg gcgctcgcat tccatcctct     2100
acacacacac acacacacac acacacacac acacacacac acacagac acgcacacac       2160 acacgcacgc acacacacgc acgcccgcac tcgtggtccc acatttattt cacaggggag     2220
gcaacaccgg ggtacgcata tggttgagtg cactggagat ctttccccac cactctcagg     2280
accccatccg gagacacagg ccacaccgca ggggcaccac gctgcgctgc tgctctgggc     2340
tagtagtctt gtgcagtttg tccgcggtgt ctgtggacgc cctcccgctc ttgtcagggg     2400
acaggaacct acactcctgc ttgcccaagg cggctgggca ggtgatgtgg tgacacccgg     2460
gacctttccg gggagttggt gttgctgcca agcctggta gttttttgaat gccaccaata     2520 gcgctaagct ttgtttccgg gcgggctgca gagcaacagg cgaaggtggc ggagtggggg    2580
tggcgcgtgt gttttttctt ttaaggggga gagaaattaa ataagaggtt ctcacacctc    2640
tgcaatctgt ttgtacttac cgtgtgtctt aacacctgac cagccagccg gtgggtcgta    2700
aaagtgtatg caggtaccag cgggacagga gatgggggcc cctgggtat ggctgggatg     2760
```

-continued

```
gaggccacct tcccgttggc ctttcaggga atctcacact tttcccttt aaaacacatg    2820
gtgttctttt taataacggc agcaactccg cattgggaaa ggggaaata agcttgtata    2880
ggccccggct ttgtggaaag gaggggaaga gggaagaaaa aaggagggg gtctcctcca    2940
ggcttagggg gctgtcagct gctgctctgt ctagcttggc atgtgtgtgc cccagtcccc    3000
agtggctttg gcccattgtt tgtggaagcc aagagggaga ctggagtcct ctatctctgg    3060
tactccagag tcaggcttct cagtccgagc ccagagaacg tcttccctgt tttatggagg    3120
gaatcaggga agggggtgcc aggtggacta cgttctgctg aggactgtac cagtcgctcg    3180
aaggagaaag cttgggcttg cccccctccc ccctcaagcc acgaagggca gctgctaggc    3240
tagtgtggta aagggcatt actccccagc caggaccccc cagagagtcc ccttcctggc    3300
cagacaaatg ctggggaggg acagaggggt gtgatcattg cccaggagtg cagacagtgg    3360
ggtcccgggt cggcagtgc ctcccaccct gctgaggggg gcgccaggc aggaagcggt     3420
gggtgggccg gggtagagac gctggcacgt cccagttcat gccgaaggaa ttctgaatta    3480
gcggcgggct ggctgcctgg gacctccggg gcggcccct ggcccccgcc gctccgtctg     3540
gcctgctcct cctgctcctt cgcacggacg ctgagacctc cgctgagccc tgggacaagc    3600
cccaaatgca actgcgattg caggcttcgc aagacccgcc tcctcccaag gccaaatttg    3660
cctgggagaa gtcattcagg gcccagacta gaaccatgtt ggtgccacct catccatctg    3720
gggcatgaag gaccgtccag ggctgcagtt tagcttctta ataggaacct ggggtgggt    3780
gcagcctctg ttctccgagc ctctttggaa atcggttttg tttttgtttt tgttttttcc    3840
aatactcttt tcctctcatc ccatcccggg actgttttcc tccctaaggg ttgagagccc    3900
tgcagtcttc cctaacctt tctttgcttc taccccaggg cctttgcaca tggagtccca    3960
cctctccct tgcccaactg gggctccagc cttactgcat ttggctcttg gtaactgtcc    4020
cagggcctct ctgacacaca gggttgtagc cccagctccc tctcttctcc tcccccttt    4080
ctcttttgct tctgagactt aatttttttc tttttctttt tggcttttg agacagggtt    4140
tctctgtaca gccctggctg ccctggcact cattctgtag accaggctag cctcaaactc    4200
acaaacctac ctgcctctgc ctttccagtg ctggcactaa agatgtgggc caccacaact    4260
agtagttaag tgttttgctg tgtctttatt cctatagtga cctcagttcc tggcatattg    4320
taggcgatgg atggatgaat ggatggatgg atggatggat ggatggttgg atggagcaag    4380
cttgaatcgt cctgagtgaa aaagagacc tcagagaact gaatgagtt aggttcccag      4440
ggcagcctgg cctgctggtc tcatgggagc tccctgtgaa acttcccca cacctcccac     4500
caccctgcca tcctgtgtgg ctgacaagaa aggccaatgg ccagatgggg acacagactc    4560
agggaagctt ggaatatgtt cccctcctca tatcctaggc cttgttgtcc ccctgagggc    4620
ccagcctatg agtagggcag ctgtgggctg ccctaaggtt gggtaggcaa gaaggggtg     4680
gtccctcagg gtgggtcaca ggattgaggt catttccaaa gtggccatca cagtggccct    4740
aggaaatgat tgtggagagt cagaactcct gttgggagtt gtagagggcc ttgcatgtgg    4800
gcttctgtgg ctgtcccttc tcttgtggtc ctttgcacag tcccctcgtg tgtgctggga    4860
tgtgaggagg gcacgggaa aatgaaggct cagcccctca gcttgccctt cacggttcac    4920
ccaacagggc tcacctctcc tctggacagg ctctcactgt atgcacagat tggcctcaca    4980
tttgattccc ttcctttggt ctcctgggat gacaaacatt taccagggta ggatttaca     5040
ttttagatat gtccattctc cagaaacaca cttgtgaggt tagggtatca gtgaaggac    5100
```

-continued

| | |
|---|---|
| accaccagga cagacaaaga attggagagg aaggaaattg gtaagccagg ccatgcttga | 5160 |
| tggcttatgt gtaatcccag aactctggac gctgaggcag gaggattcca agtttcaaga | 5220 |
| cagtgtgttc taggtaatga gaccctgtca agaaaagaaa agaaataaag agacaagaaa | 5280 |
| atgtttatag gctgtgagac agcttggtgg gtaagggca cttgcctcca atcaagatga | 5340 |
| cctcagcccc atccctagga atccatggta gaaggagaaa gcaaactcca gctgctgacc | 5400 |
| tccatacatg tgctccaatg tgcacacaca cagggagaca taatcaatta ataggatgta | 5460 |
| tttgcttaga tttgagtagg catttatgac tgatgtttta aaattttttat ttgattttat | 5520 |
| gaaaatatac ctgtttgtat ttggtttggt ttggtttgag ttttgtttat ttgagacagg | 5580 |
| gcttctctgt gtagtcctgg ctgtccttgg aactcactct gtagaccagg ctggccttga | 5640 |
| actcagaaat ccgcctgctt gtgcttccca agtgcttaga ttaaaggtgt gcactgccat | 5700 |
| tcagcaaaat tgcatacttt aaccccagta tttgggaggc agaggcagac taatgtgtga | 5760 |
| attccaggct agccaaggat acagagtgag accctattct taccctcccc ccccaaaacc | 5820 |
| ccaaaatgta ttttgtgctt gtgtatgtac atgtgtgttg cagcacgtaa atgtccaagg | 5880 |
| acaacttgta gaagttctct ccgttcacag tctaagtcct gaattcaaac taaggtcctc | 5940 |
| aggcttagcc acagtcttct ttatgtactg agccatttca ctggccctgg attgactgat | 6000 |
| gaattaattt ttgagataag gtctcttgta gctctagcta ggctcaaact atgaactccc | 6060 |
| aaggtcatct tgagctgctg gtactcttgc ttccacccca agtggtggaa tgatactcag | 6120 |
| gcagcacttc tctggggaag gggctggcct tggccttgat tttgttgcct cagcttcaat | 6180 |
| gagtgcttgg gtctcgttgt ttcttttctt tatctgtgaa atgggtgaac acctgttcaa | 6240 |
| gacttcctga ctcttgaaac atccaggcag ggtgagggac ttgaagtggg ctcatcccat | 6300 |
| gcctaacaaa gtgtcgtctt tgaccccaga cacagctgta atcagccccc aggacccac | 6360 |
| ccttctcatc ggctcctccc tgcaagctac ctgctctata catggagaca cacctggggc | 6420 |
| caccgctgag gggctctact ggaccttcaa tggtcgccgc ctgccctctg agctgtcccg | 6480 |
| cctccttaac acctccaccc tggccctggc cctggctaac cttaatgggt ccaggcagca | 6540 |
| gtcaggagac aatctggtgt gtcacgcccg agacggcagc attctggctg gctcctgcct | 6600 |
| ctatgttggc tgtaagtggg gccccagaca ctcagagata gatgggggtt ggcaatgaca | 6660 |
| gatttagagc ctgggtcttc tgtcctgggg cagagccatg ggctctcact tgcatgcagg | 6720 |
| catggtcata cccagcacag gcattgcaac tctaggggaca gctgtggctg cactgtcccc | 6780 |
| tgtgtacccc acagctttag aaaagctgtc atgtttttcct tgtagtgccc cctgagaagc | 6840 |
| cctttaacat cagctgctgg tcccggaaca tgaaggatct cacgtgccgc tggacaccgg | 6900 |
| gtgcacacgg ggagacattc ttacatacca actactccct caagtacaag ctgaggttgg | 6960 |
| tacccagcca agccttgctg tgtgacttct ggcaatactt accttctctg atcaaatatg | 7020 |
| ttcctgttta tgaactcaaa agggactctc gcacctccac aggtggtacg gtcaggataa | 7080 |
| cacatgtgag gagtaccaca ctgtgggccc tcactcatgc catatcccca aggacctggc | 7140 |
| cctcttcact ccctatgaga tctgggtgga agccaccaat cgcctaggct cagcaagatc | 7200 |
| tgatgtcctc acactggatg tcctggacgt gggtgagccc ccagtgtcca cctgtgttct | 7260 |
| gcccctagacc ttatagggcg cctcccccc atcccccag acttttttggt tcttctagag | 7320 |
| gtcttagcca cagccacggt ggttgcagga cagtggttgt tcataactta atgcaaagac | 7380 |
| tttcccccaa gacagtcaag attttcccct cccaccccc aacacacaca tacacacaca | 7440 |
| ctctgcagag aacacctggc ctgaccaccc tccctctcta cagcccaggt gttcagaagg | 7500 |

```
gagtcctagg ggactgagag gaggcgccca ggtctgaagg cgccccagga agccgaggcc    7560
ttgagctggg ggggggggcg agggttggag gcacgaactg gatgatccct gagcacaact    7620
gggcctaatc taattagggt gttcccagcc caaagcagcc tgggccattt aacccttcaa    7680
gtgcctcact gaagactcag gggagagatc agcttgtact ctctccatgg tcccccagga    7740
gggttcctgg gtgcccctgg ctcattccca catccagagg ttttgtgtct tcctggcatc    7800
taaccctcag ttgtgctctg tggctggcac agctgccccg tggaggctct tggtaatgta    7860
caaggcatca gaggtggaca tgggatgggg atacataggg atggagccaa atagcacctc    7920
aaggtggggt gatatacaat aaagcttgtc accctgacgc tcagaaagcc tactcatgat    7980
gatcacaatt gttgacatca ctctgggaca tgtagtgaga ccctagctca aaacacagac    8040
agtagcttta agagtcagct tgtgacttaa tactggaact cagggcctaa taggtgctgg    8100
gtgatgctcg cctcactccc tgtttagtga gatctctgcg ctaatctcca ccccagctgg    8160
gtgggctgct ctgtccccft gagggcagga atgtgtgtct tccatcagag ataggacccg    8220
tggtagcagc aactgctgct ggctgtttct ggaatattaa atgacagtaa tctatcaggc    8280
ctgggtgagt agctaacagg ggtgggggcg tggtctggaa aacgcagata gggtcatagg    8340
agccactgca gcctagatta caccactggg tgttctgtca ctaggccatt ctccaccaagc   8400 agtcctcaga actgggagca ctgttgccag catttaatgc cagcatttaa tgccagcatt    8460
aggggaggca gaggcagaag gatctctctg agttcaaggc catcctgaat ttacataaag    8520
agctccaggc cagccaggt gcgcagtaaa accttgtctc aaaaaacaaa gcatctttag     8580
tgaccaggct tgctccaccc ccagtgacca cggaccccccc acccgacgtg cacgtgagcc   8640
gcgttggggg cctggaggac cagctgagtg tgcgctgggt ctcaccacca gctctcaagg    8700
atttcctctt ccaagccaag taccagatcc gctaccgcgt ggaggacagc gtggactgga    8760
aggtgcccgt cccgccccgg acccgccccct gaccccgccc cccgcatctg actcctccct   8820
caccgtgcag gtggtggatg acgtcagcaa ccagacctcc tgccgtctcg cgggcctgaa    8880
gcccggcacc gtttacttcg tccaagtgcg ttgtaaccca ttcgggatct atgggtcgaa    8940
aaaggcggga atctggagcg agtggagcca ccccaccgct gcctccaccc ctcgaagtgg    9000
tgagcacctc tccagggctg gctggcccat ggaatcccca atccatcctg ttccttcccc    9060
cccacccttt ttttgagaca gcgtcttcag gtagcgcatg ctggccttaa attcagtatg    9120
tagtcaagga tgacctcgag ctcctggtct ttttgtctcc acttagagac aatggccagt    9180
ggccatcacc acctttggga gactagccat ggagtctatt tagcctgtca tttggtgaca    9240
gatggagtac aacagtgtga cctcttgtaa gagaactgaa gacaggctgt ttttaaccccc   9300 aatatcctag gctctctaga ggttaacttt atataaaata gagactatta cagccagtta    9360
tcacatggtc ccacagaacc ttttgtcaca caacctatag accacagtgc ctgtgcctac    9420
cacataaggg tctctactgc tggcccaccc ctccaacccct taaaaggtaa cctaggcagc   9480
cttaatattt gcaatcctcc tacctcagcc tcttgaatgc tcagaaacca ggcattaacc    9540
caagtttctc ttctctgggt ccctttctta aggtgggagg gcctaaagat gacttccttt    9600
gtcctgaaga ctctccgagc ccatggatct gcactctcta atatgaaata tattgcataa    9660
aatgtctggc ctcagtttcc ccacctgtca ggtttaggca gcacagtcgg tccaagacac    9720
ttcattattt gcaggcagta taagaagaag ctcccatccc ccaccgctt cctccggtcc     9780 ctaagacaga atacttctac actgaaactg aactctcgca gacgcatatg ctcactttaa    9840
```

```
tgatgatgaa ataatgggga aactgaggct ccgagagatt cctggaggaa gagggtcaaa      9900
accagctcca ggaagctctc cagcccccat ccgggcctct ccaggttctg ggcttggcgg      9960
gagtgaacac agctgggagg ggctggagcc tgggagcttt ggcccttgct cgtgcccagc     10020
acctgcgatt cttgcacggg agccagcagg cggctgcgtc cgcccgagag actgaagaag     10080 ccggggtag ggttggaggg aggtaagcag gggctgtggg ggccgaagct tgtgccaggg      10140
cctgtcagcg agtccccagt tttatttatg gcgtgaggcc gatgtccttα tccgctggcc     10200 tgctggggga tggctgcggc tgggattgg acccaagggc tggcttccca ctcagtcctc      10260
cagcccactc catgtcacac ccgtgcattc tctgaggctt atcttgggaa cccgcccttg     10320
ttctgtgctg tctgtctcta tttctgtcat tcactttccc agagcctttt ttttatgctt    10380
ttaatataac tacgttttaa aaattgcttt tgtataatgt gtgtgccttc gtgagcgtgc     10440
gtgccacaac acacgtgα aggttagagα actttgttga gtaggctcct tccaccatgt      10500
gggactaggg ctggcgacaa gagcaattac tgagtcatct cgccagcccc tcacccctca    10560
cttcccatcc tgtttggata gtcataggta atcgaaggta aatcgctggc tttaatttcg    10620
tagctatcct gcctcagcct accaagtgct gtgctaccac gtttgtggga ggggctctcc    10680
tcccagtgtc tgggggtaca cagtcccaag atctctgctt tctaggtctt tgtcttagtt    10740
tgccccttgc tttgtccgtg tccctagagt ctccggcccc acttagtctc cattgatttc   10800
ctttctgacc gaatactcgg ttttacctcc cactgatttg actccctcct ttgcttgtct    10860
ccatcgccgt ggcattgcca ttcctctggg tgactctggg tccacacctg acacctttcc    10920
caactttccc cagccgaagc tggtctggta tgggaggccg ccgtcccgcg cgcgcctcct    10980
gctggccgcg ccccaacact gccgctccat tctctttaga gcgcccgggc ccgggcggcg   11040
gggtgtgcca gccgcggggc ggcgagccca gctcgggccc ggtgcggcgc gagctcaagc    11100
agttcctcgg ctggctcaag aagcacgcat actgctcgaa ccttagtttc cgcctgtacg    11160
accagtggcg tgcttggatg cagaagtcac acaagacccg aaaccaggta ggaaagttgg    11220
gggaggcttg cgtgggggt aaaggagcag aggaagagag agacccgggt gagcagcctc    11280
cacaacaccg cactcttctt tccaagcaca ggacgagggg atcctgccct cgggcagacg    11340
gggtgcggcg agaggtaagg gggtctgggt gagtggggcc tacagcagtc tagatgaggc    11400
cctttcccct ccttcggtgt tgctcaaagg gatctcttag tgctcatttc acccactgca    11460
aagagcccca ggttttactg catcatcaag ttgctgaagg gtccaggctt aatgtggcct    11520
cttttctgcc ctcaggtcct gccggctaaa ctctaaggat aggccatcct cctgctgggt    11580
cagacctgga ggctcacctg aattggagcc cctctgtacc atctgggcaa caaagaaacc    11640
taccagaggc tgggcacaat gagctcccac aaccacagct ttggtccaca tgatggtcac    11700
acttggatat accccagtgt gggtagggtt ggggtattgc agggcctccc aagagtctct    11760
ttaaataaat aaaggagttg ttcaggtccc gatggccagt gtgtttgggg cctatgtgct    11820
ggggtggggg ga                                                         11832
```

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence:Murine peptide

<400> SEQUENCE: 39

```
Val Ile Ser Pro Gln Asp Pro Thr Leu Leu Ile Gly Ser Ser Leu Gln
 1               5                  10                  15

Ala Thr Cys Ser Ile His Gly Asp Thr Pro
            20                  25

<210> SEQ ID NO 40
<211> LENGTH: 21
<212> TYPE: DNA
<213> ORGANISM: Oligonucleotide Sequence

<400> SEQUENCE: 40
gtccaagtgc gttgtaaccc a                                           21

<210> SEQ ID NO 41
<211> LENGTH: 24
<212> TYPE: DNA
<213> ORGANISM: Oligonucleotide Sequence

<400> SEQUENCE: 41
gctgagtgtg cgctgggtct cacc                                        24

<210> SEQ ID NO 42
<211> LENGTH: 18
<212> TYPE: DNA
<213> ORGANISM: Oligonucleotide Sequence

<400> SEQUENCE: 42
ggctccactc gctccaga                                               18

<210> SEQ ID NO 43
<211> LENGTH: 2079
<212> TYPE: DNA
<213> ORGANISM: Unknown
<220> FEATURE:
<221> NAME/KEY: CDS
<222> LOCATION: (513)..(1775)
<220> FEATURE:
<223> OTHER INFORMATION: Description of Unknown Organism: Nucleotide
      Sequence of NR6

<400> SEQUENCE: 43
gcggtatttg tgtttcaaat ctatctacag aaaagattga gaaccagaag cccttttcgt    60
tttttgaaag ctagctgact cactgttcaa gaaaggagaa cactttcaat tatgctgttt   120
gactgcagtg tcagggatcc aaaggaaatg actccatccc ttcccttca tcccaacctc    180 agtgacagca aattctgatg tgactgaggg ttggcttgtg aaggagtcat taggaaattc   240
tgcctaagcc atagcgcgat gagaaggatg tatcctatgg tggtgatttt cctgtgcccc   300
ctcagaggaa agttgtcaga tgagcaggtg gagtattcta tagcaaacag caagctaata   360
ggttacacag ataactctct gactttgcct tacagaacct gtgctattga ccttagggca   420
aggttcatgc tcagggggcc aactctgtgg gttaggattt gagtttaagc agcttctgct   480
catatttcag cgccccggc agcgccggcc cc atg ccc gcc ggc cgc cgg ggc      533
                                 Met Pro Ala Gly Arg Arg Gly
                                  1               5 ccc gcc gcc caa tcc gcg cgg cgg ccg ccg ccg ttg ctg ccc ctg ctg     581
Pro Ala Ala Gln Ser Ala Arg Arg Pro Pro Pro Leu Leu Pro Leu Leu
            10                  15                  20 ctg ctc tgc gtc ctc ggg gcg ccg cga gcc gga tca gga gcc cac aca     629
Leu Leu Cys Val Leu Gly Ala Pro Arg Ala Gly Ser Gly Ala His Thr
        25                  30                  35 gct gtg atc agt ccc cag gat ccc acg ctt ctc atc ggc tcc tcc ctg     677
```

-continued

| | | | | | | | | | | | | | | | |
|---|---|---|---|---|---|---|---|---|---|---|---|---|---|---|---|
| Ala | Val | Ile | Ser | Pro | Gln | Asp | Pro | Thr | Leu | Leu | Ile | Gly | Ser | Ser | Leu |
| 40 | | | | 45 | | | | | 50 | | | | | 55 | |

```
ctg gcc acc tgc tca gtg cac gga gac cca cca gga gcc acc gcc gag      725
Leu Ala Thr Cys Ser Val His Gly Asp Pro Pro Gly Ala Thr Ala Glu
            60                  65                  70 ggc ctc tac tgg acc ctc aat ggg cgc cgc ctg ccc cct gag ctc tcc      773
Gly Leu Tyr Trp Thr Leu Asn Gly Arg Arg Leu Pro Pro Glu Leu Ser
            75                  80                  85 cgt gta ctc aac gcc tcc acc ttg gct ctg gcc ctg gcc aac ctc aat      821
Arg Val Leu Asn Ala Ser Thr Leu Ala Leu Ala Leu Ala Asn Leu Asn
        90                  95                  100 ggg tcc agg cag cgg tcg ggg gac aac ctc gtg tgc cac gcc cgt gac      869
Gly Ser Arg Gln Arg Ser Gly Asp Asn Leu Val Cys His Ala Arg Asp
    105                 110                 115 ggc agc atc ctg gct ggc tcc tgc ctc tat gtt ggc ctg ccc cca gag      917
Gly Ser Ile Leu Ala Gly Ser Cys Leu Tyr Val Gly Leu Pro Pro Glu
120                 125                 130                 135 aaa ccc gtc aac atc agc tgc tgg tcc aag aac atg aag gac ttg acc      965
Lys Pro Val Asn Ile Ser Cys Trp Ser Lys Asn Met Lys Asp Leu Thr
                140                 145                 150 tgc cgc tgg acg cca ggg gcc cac ggg gag acc ttc ctc cac acc aac     1013
Cys Arg Trp Thr Pro Gly Ala His Gly Glu Thr Phe Leu His Thr Asn
            155                 160                 165 tac tcc ctc aag tac aag ctt agg tgg tat ggc cag gac aac aca tgt     1061
Tyr Ser Leu Lys Tyr Lys Leu Arg Trp Tyr Gly Gln Asp Asn Thr Cys
        170                 175                 180 gag gag tac cac aca gtg ggg ccc cac tcc tgc cac atc ccc aag gac     1109
Glu Glu Tyr His Thr Val Gly Pro His Ser Cys His Ile Pro Lys Asp
    185                 190                 195 ctg gct ctc ttt acg ccc tat gag atc tgg gtg gag gcc acc aac cgc     1157
Leu Ala Leu Phe Thr Pro Tyr Glu Ile Trp Val Glu Ala Thr Asn Arg
200                 205                 210                 215 ctg ggc tct gcc cgc tcc gat gta ctc acg ctg gat atc ctg gat gtg     1205
Leu Gly Ser Ala Arg Ser Asp Val Leu Thr Leu Asp Ile Leu Asp Val
                220                 225                 230 gtg acc acg gac ccc ccg ccc gac gtg cac gtg agc cgc gtc ggg ggc     1253
Val Thr Thr Asp Pro Pro Pro Asp Val His Val Ser Arg Val Gly Gly
            235                 240                 245 ctg gag gac cag ctg agc gtg cgc tgg gtg tcg cca ccc gcc ctc aag     1301
Leu Glu Asp Gln Leu Ser Val Arg Trp Val Ser Pro Pro Ala Leu Lys
        250                 255                 260 gat ttc ctc ttt caa gcc aaa tac cag atc cgc tac cga gtg gag gac     1349
Asp Phe Leu Phe Gln Ala Lys Tyr Gln Ile Arg Tyr Arg Val Glu Asp
    265                 270                 275 agt gtg gac tgg aag gtg gtg gac gat gtg agc aac cag acc tcc tgc     1397
Ser Val Asp Trp Lys Val Val Asp Asp Val Ser Asn Gln Thr Ser Cys
280                 285                 290                 295 cgc ctg gcc ggc ctg aaa ccc ggc acc gtg tac ttc gtg caa gtg cgc     1445
Arg Leu Ala Gly Leu Lys Pro Gly Thr Val Tyr Phe Val Gln Val Arg
                300                 305                 310 tgc aac ccc ttt ggc atc tat ggc tcc aag aaa gcc ggg atc tgg agt     1493
Cys Asn Pro Phe Gly Ile Tyr Gly Ser Lys Lys Ala Gly Ile Trp Ser
            315                 320                 325 gag tgg agc cac ccc aca gcc gcc tcc act ccc cgc agt gag cgc ccg     1541
Glu Trp Ser His Pro Thr Ala Ala Ser Thr Pro Arg Ser Glu Arg Pro
        330                 335                 340 ggc ccg ggc ggc ggg gcg tgc gaa ccg cgg ggc gga gag ccg agc tcg     1589
Gly Pro Gly Gly Gly Ala Cys Glu Pro Arg Gly Gly Glu Pro Ser Ser
    345                 350                 355
```

-continued

```
ggg ccg gtg cgg cgc gag ctc aag cag ttc ctg ggc tgg ctc aag aag    1637
Gly Pro Val Arg Arg Glu Leu Lys Gln Phe Leu Gly Trp Leu Lys Lys
360                 365                 370                 375 cac gcg tac tgc tcc aac ctc agc ttc cgc ctc tac gac cag tgg cga    1685
His Ala Tyr Cys Ser Asn Leu Ser Phe Arg Leu Tyr Asp Gln Trp Arg
                380                 385                 390 gcc tgg atg cag aag tcg cac aag acc cgc aac cag gac gag ggg atc    1733
Ala Trp Met Gln Lys Ser His Lys Thr Arg Asn Gln Asp Glu Gly Ile
            395                 400                 405 ctg ccc tcg ggc aga cgg ggc acg gcg aga ggt cct gcc aga            1775
Leu Pro Ser Gly Arg Arg Gly Thr Ala Arg Gly Pro Ala Arg
        410                 415                 420 taagctgtag gggctcaggc caccctccct gccacgtgga gacgcagagg ccgaacccaa  1835
actgggccca cctctgtacc ctcacttcag ggcacctgag ccaccctcag caggagctgg  1895
ggtggcccct gagctccaac ggccataaca gctctgactc ccacgtgagg ccacctttgg  1955
gtgcacccca gtgggtgtgt gtgtgtgtgt gagggttggt tgagttgcct agaaccctg   2015 ccagggctgg gggtgagaag gggagtcatt actccccatt acctagggcc cctccaaaag  2075
atcc                                                               2079
```

<210> SEQ ID NO 44
<211> LENGTH: 421
<212> TYPE: PRT
<213> ORGANISM: Unknown
<220> FEATURE:
<223> OTHER INFORMATION: Description of Unknown Organism: Amino Acid Sequence of NR6

<400> SEQUENCE: 44

```
Met Pro Ala Gly Arg Arg Gly Pro Ala Ala Gln Ser Ala Arg Arg Pro
 1               5                  10                  15

Pro Pro Leu Leu Pro Leu Leu Leu Cys Val Leu Gly Ala Pro Arg
            20                  25                  30

Ala Gly Ser Gly Ala His Thr Ala Val Ile Ser Pro Gln Asp Pro Thr
        35                  40                  45

Leu Leu Ile Gly Ser Ser Leu Leu Ala Thr Cys Ser Val His Gly Asp
    50                  55                  60

Pro Pro Gly Ala Thr Ala Glu Gly Leu Tyr Trp Thr Leu Asn Gly Arg
65                  70                  75                  80

Arg Leu Pro Pro Glu Leu Ser Arg Val Leu Asn Ala Ser Thr Leu Ala
                85                  90                  95

Leu Ala Leu Ala Asn Leu Asn Gly Ser Arg Gln Arg Ser Gly Asp Asn
            100                 105                 110

Leu Val Cys His Ala Arg Asp Gly Ser Ile Leu Ala Gly Ser Cys Leu
        115                 120                 125

Tyr Val Gly Leu Pro Pro Glu Lys Pro Val Asn Ile Ser Cys Trp Ser
    130                 135                 140

Lys Asn Met Lys Asp Leu Thr Cys Arg Trp Thr Pro Gly Ala His Gly
145                 150                 155                 160

Glu Thr Phe Leu His Thr Asn Tyr Ser Leu Lys Tyr Lys Leu Arg Trp
                165                 170                 175

Tyr Gly Gln Asp Asn Thr Cys Glu Glu Tyr His Thr Val Gly Pro His
            180                 185                 190

Ser Cys His Ile Pro Lys Asp Leu Ala Leu Phe Thr Pro Tyr Glu Ile
        195                 200                 205

Trp Val Glu Ala Thr Asn Arg Leu Gly Ser Ala Arg Ser Asp Val Leu
```

```
            210                 215                 220
Thr Leu Asp Ile Leu Asp Val Val Thr Asp Pro Pro Asp Val
225                 230                 235                 240

His Val Ser Arg Val Gly Gly Leu Glu Asp Gln Leu Ser Val Arg Trp
                245                 250                 255

Val Ser Pro Pro Ala Leu Lys Asp Phe Leu Phe Gln Ala Lys Tyr Gln
                260                 265                 270

Ile Arg Tyr Arg Val Glu Asp Ser Val Asp Trp Lys Val Val Asp Asp
                275                 280                 285

Val Ser Asn Gln Thr Ser Cys Arg Leu Ala Gly Leu Lys Pro Gly Thr
290                 295                 300

Val Tyr Phe Val Gln Val Arg Cys Asn Pro Phe Gly Ile Tyr Gly Ser
305                 310                 315                 320

Lys Lys Ala Gly Ile Trp Ser Glu Trp Ser His Pro Thr Ala Ala Ser
                325                 330                 335

Thr Pro Arg Ser Glu Arg Pro Gly Pro Gly Gly Ala Cys Glu Pro
                340                 345                 350

Arg Gly Gly Glu Pro Ser Ser Gly Pro Val Arg Arg Glu Leu Lys Gln
                355                 360                 365

Phe Leu Gly Trp Leu Lys Lys His Ala Tyr Cys Ser Asn Leu Ser Phe
370                 375                 380

Arg Leu Tyr Asp Gln Trp Arg Ala Trp Met Gln Lys Ser His Lys Thr
385                 390                 395                 400

Arg Asn Gln Asp Glu Gly Ile Leu Pro Ser Gly Arg Arg Gly Thr Ala
                405                 410                 415

Arg Gly Pro Ala Arg
                420

<210> SEQ ID NO 45
<211> LENGTH: 23
<212> TYPE: DNA
<213> ORGANISM: Artificial
<220> FEATURE:
<223> OTHER INFORMATION: Description of Artificial Sequence: Fwd Primer

<400> SEQUENCE: 45
tgcccccaga gaaacccgtc aac                                          23

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:  Rev Primer

<400> SEQUENCE: 46
cgtgagtaca tcggagcggg cagag                                        25

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
tcaggcgcgc cttgcccaca cagctgtgat c                                 31
```

```
<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
tcagggcgcg ccttatctgg caggacctct                              30

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
tcaggcgcgc ctgcccgccg gccgc                                   25

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
ataaggcgcg ccctggcagg acctctcg                                28

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
tcaggcgcgc cttgcccaca cagctgtgat c                            31

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52
tcagggcgcg ccttatctgg caggacctct                              30

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
tcaggcgcgc ctgcccgccg gccgc                                   25

<210> SEQ ID NO 54
```

-continued

```
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
ataaggcgcg ccctggcagg acctctcg                                            28
```

HAEMOPOIETIN RECEPTOR AND GENETIC SEQUENCE ENCODING SAME

CROSS REFERENCE TO RELATED APPLICATION

The present application is a continuation-in-part of application Ser. No. 08/928,720 filed Sep. 11, 1997 now abandoned.

FIELD OF THE INVENTION

The present invention relates generally to a novel haemopoietin receptor or derivatives thereof and to genetic sequences encoding same. Interaction between the novel receptor of the present invention and a ligand facilitates proliferation, differentiation and survival of a wide variety of cells. The novel receptor and its derivatives and the genetic sequences encoding same of the present invention are useful in the development of a wide range of agonists, antagonists, therapeutics and diagnostic reagents based on ligand interaction with its receptor.

Bibliographic details of the publications numerically referred to in this specification are collected at the end of the description. Sequence Identity Numbers (SEQ ID NOs.) for the nucleotide and amino acid sequences referred to in the specification are defined following the bibliography.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

BACKGROUND OF THE INVENTION

The rapidly increasing sophistication of recombinant DNA techniques is greatly facilitating research into the medical and allied health fields. Cytokine research is of particular importance, especially as these molecules regulate the proliferation, differentiation and function of a wide variety of cells. Administration of recombinant cytokines or regulating cytokine function and/or synthesis is becoming increasingly the focus of medical research into the treatment of a range of disease conditions.

Despite the discovery of a range of cytokines and other secreted regulators of cell function, comparatively few cytokines are directly used or targeted in therapeutic regimens. One reason for this is the pleiotropic nature of many cytokines. For example, interleukin (IL)-11 is a functionally pleiotropic molecule (1,2), initially characterized by its ability to stimulate proliferation of the IL-6-dependent plasmacytoma cell line, T11 65 (3). Other biological actions of IL11 include induction of multipotential haemopoietin progenitor cell proliferation (4,5,6), enhancement of megakaryocyte and platelet formation (7,8,9,10), stimulation of acute phase protein synthesis (11) and inhibition of adipocyte lipoprotein lipase activity (12, 13).

Other important cytokines in the IL-11 group include IL6, leukaemia inhibitory factor (LIF), oncostatin M (OSM) and CNTF. All these cytokines exhibit pleiotropic properties with significant activities in proliferation, differentiation and survival of cells. Members of the haemopoietin receptor family are defined by the presence of a conserved amino acid domain in their extracellular region. However, despite the low level of amino acid sequence conservation between other haemopoietin receptor domains of different receptors, they are all predicted to assume a similar tertiary structure, centred around two fibronectin-type III repeats (18,19).

The size of the haemopoietin receptor family has now become extensive and includes the cell surface receptors for may cytokines including interleukin-2 (IL2), IL-3, IL4, IL5, IL-6, IL-7, IL-9, IL-11, IL-12, IL-13, IL-15, granulocyte colony stimulating factor (G-CSF), granulocyte-macrophage-CSF (GM-CSF), erythropoietin, thrombopoietin, leptin, leukaemia inhibitory factor, oncostatin-M, ciliary neurotrophic factor, cardiotrophin, growth hormone and prolactin. Although most of the members of the haemopoietin receptor family act as classic cell surface receptors, binding their cognate ligand at the cell surface and initiating intracellular signal transduction, some receptors are also produced in naturally occurring soluble forms. These soluble receptors can either act as cytokine antagonists, by binding to cytokines and inhibiting productive interactions with cell surface receptors (eg LIF binding protein; (20) or as agonists, binding to cytokine and potentiating interaction with cell surface receptor components (eg soluble interleukin-6 receptor a-chain; (21). Still other members of the family appear to be produced only as secreted proteins, with no evidence of a cell surface form In this regard, the IL-12 p40 subunit is a useful example. The cytokine IL-12 is secreted as a heterodimer composed of a p35 subunit which shows similarity to cytokines such as IL-6 (22) and a p40 subunit which shares similarity with the IL-6 receptor a-chain (23). In this case the soluble receptor acts as part of the cytokine itself and essential to formation of an active protein. In addition to acting as cytokines (eg IL-12p40), cytokine agonists (eg IL-6 receptor a-chain) or cytokine antagonists (LIF binding protein), members of the haemopoietin receptor have been useful in the discovery of small molecule cytokine mimetics. For example, the discovery of peptide mimetics of two commercially valuable cytokines, erythropoietin and thrombopoietin, centred on the selection of peptides capable of binding to soluble versions of the erythropoietin and thrombopoietin receptors (24,25). Due to the importance and multifactorial nature of these cytokines, there is a need to identify receptors, including both cell bound and soluble, for pleiotropic cytokines. Identification of such receptors permits the identification of pleiotropic cytokines and the development of a range of therapeutic and diagnostic agents.

DETAILED DESCRIPTION OF THE INVENTION

One aspect of the present invention relates to a nucleic acid molecule comprising a sequence of nucleotides encoding or complementary to a sequence encoding a novel haemopoietin receptor or a derivative thereof.

More particularly, the present invention provides a nucleic acid molecule comprising a sequence of nucleotides encoding or complementary to a sequence encoding a novel haemopoietin receptor or a derivative thereof having the motif:

Trp Ser Xaa Trp Ser [SEQ ID NO:1], wherein Xaa is any amino acid and is preferably Asp or Glu.

Even more particularly, the present invention is directed to a nucleic acid molecule comprising a sequence of nucleotides encoding or complementary to a sequence encoding a novel haemopoietin receptor or a derivative thereof, said receptor comprising the motif:

Trp Ser Xaa Trp Ser [SEQ ID NO:1]

wherein Xaa is any amino acid and is preferably Asp or Glu, said nucleic acid molecule is identifiable by hybridisation to said molecule under low stringency conditions at 42° C. with

5' (A/G)CTCCA(A/G)TC(A/G)CTCCA 3' [SEQ ID NO:7]

and

5' (A/G)CTCCA(C/T)TC(A/G)CTCCA 3' [SEQ ID NO:8].

Still more particularly, the present invention provides an isolated nucleic acid molecule comprising a sequence of nucleotides substantially as set forth in SEQ ID NO:12 or a nucleotide sequence having at least 60% similarity to the nucleotide sequence set forth in SEQ ID NO:12 or a nucleotide sequence capable of hybridising thereto under low stringency conditions at 42° C. and wherein said nucleotide sequence encodes a novel haemopoietin receptor or a derivative thereof.

In a related embodiment, the present invention provides an isolated nucleic acid molecule comprising a sequence of nucleotides substantially as set forth in SEQ ID NO:14 or a nucleotide sequence having at least 60% similarity to the nucleotide sequence set forth in SEQ ID NO:14 or a nucleotide sequence capable of hybridising thereto under low stringency conditions at 42° C. and wherein said nucleotide sequence encodes a novel haemopoietin receptor or a derivative thereof.

In another related embodiment, the present invention provides an isolated nucleic acid molecule comprising a sequence of nucleotides substantially as set forth in SEQ ID NO:16 or a nucleotide sequence having at least 60% similarity to the nucleotide sequence set forth in SEQ ID NO:16 or a nucleotide sequence capable of hybridising thereto under low stringency conditions at 42° C. and wherein said nucleotide sequence encodes a novel haemopoietin receptor or a derivative thereof.

In a further related embodiment, the present invention provides an isolated nucleic acid molecule comprising a sequence of nucleotides substantially as set forth in SEQ ID NO:18 or a nucleotide sequence having at least 60% similarity to the nucleotide sequence set forth in SEQ ID NO:18 or a nucleotide sequence capable of hybridising thereto under low stringency conditions at 42° C. and wherein said nucleotide sequence encodes a novel haemopoietin receptor or a derivative thereof.

In yet a further related embodiment, the present invention provides an isolated nucleic acid molecule comprising a sequence of nucleotides substantially as set forth in SEQ ID NO:24 or a nucleotide sequence having at least 60% similarity to the nucleotide sequence set forth in SEQ ID NO:24 or a nucleotide sequence capable of hybridising thereto under low stringency conditions at 42° C. and wherein said nucleotide sequence encodes a novel haemopoietin receptor or a derivative thereof.

Still yet a further embodiment of the present invention is directed to a sequence of nucleotides substantially as set forth in SEQ ID NO:28 or a nucleotide sequence having at least 60% similarity to the nucleotide sequence set forth in SEQ ID NO:28 or a nucleotide sequence capable of hybridising thereto under low stringency conditions at 42° C. and wherein said nucleotide sequence encodes a novel haemopoietin receptor or a derivative thereof.

In still yet another embodiment, the present invention provides an isolated nucleic acid molecule comprising a sequence of nucleotides substantially set forth in SEQ ID NO:38 or a nucleotide sequence having at least 60% similarity to the nucleotide sequence set forth in SEQ ID NO:38 or a nucleotide sequence capable of hybridising thereto under low stringency conditions at 42° C. and wherein said nucleotide sequence encodes a novel haemopoietin receptor or a derivative thereof.

Another embodiment of the present invention provides an isolated nucleic acid molecule comprising a sequence of nucleotides substantially set forth in SEQ ID NO:43 or a nucleotide sequence having at least 60% similarity to the nucleotide sequence set forth in SEQ ID NO:43 or a nucleotide sequence capable of hybridising thereto under low stringency conditions at 42° C. and wherein said nucleotide sequence encodes a novel haemopoietin receptor or a derivative thereof.

The term "receptor" is used in its broadest sense and includes any molecule capable of binding, associating or otherwise interacting with a ligand. Generally, the interaction will have a signalling effect although the present invention is not necessarily so limited. For example, the "receptor" may be in soluble form, often referred to as a cytokine binding protein. A receptor may be deemed a receptor notwithstanding that its ligand or ligands has or have not been identified.

Preferably, the novel receptor is derived from a mammal or a species of bird. Particularly, preferred mammals include humans, primates, laboratory test animals (e.g. mice, rats, rabbits, guinea pigs), livestock animals (e.g. sheep, horses, pigs, cows), companion animals (e.g. dogs, cats) or captive wild animals (e.g. deer, foxes, kangaroos). Although the present invention is exemplified with respect to mice, the scope of the subject invention extends to all animals and in particular humans.

The present invention is predicated in part on an ability to identify members of the haemopoietin receptor family with limited sequence similarity. Based on this approach, a genetic sequence has been identified in accordance with the present invention which encodes a novel receptor. The expressed genetic sequence is referred to herein as "NR6". Different forms of NR6 are referred to as, for example, NR6.1, NR6.2 and NR6.3. The nucleotide and corresponding amino acid sequences for these molecules are represented in SEQ ID NOs: 12, 14 and 16, respectively.

Preferred human and murine nucleic acid sequences for NR6 or its derivatives include sequences from brain, liver, kidney, neonatal, embryonic, cancer or tumour-derived tissues.

Reference herein to a low stringency at 42° C. includes and encompasses from at least about 1% v/v to at least about 15% v/v for amide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0. 15M salt for hybridisation, and at least about 0.01M to at least about 0.5M salt for washing conditions.

The nucleic acid molecules contemplated by the present invention are generally in isolated form and are preferably cDNA or genomic DNA molecules. In a particularly preferred embodiment, the nucleic acid molecules are in vectors and most preferably expression vectors to enable expression in a suitable host cell. Particularly useful host cells include prokaryotic cells, mammalian cells, yeast cells and insect cells. The cells may also be in the form of a cell line.

Accordingly, another aspect of the present invention provides an expression vector comprising a nucleic acid molecule encoding the novel haempoietin receptor or a derivative thereof as hereinbefore described, said expression vector capable of expression in a selected host cell.

Another aspect of the present invention contemplates a method for cloning a nucleotide sequence encoding NR6 or a derivative thereof, said method comprising searching a nucleotide data base for a sequence which encodes the amino acid sequence set forth in SEQ ID NO:1, designing one or more oligonucleotide primers based on the nucleotide sequence located in the search, screening a nucleic acid library with said one or more oligonucleotides and obtaining a clone therefrom which encodes said NR6 or part thereof.

Once a novel nucleotide sequence is obtained as indicated above encoding NR6, oligonucleotides may be designed which bind cDNA clones with high stringency. Direct colony hybridisation may be employed or PCR amplification may be used. The use of oligonucleotide primers which bind under conditions of high stringency ensures rapid cloning of a molecule encoding the novel NR6 and less time is required in screening out cloning artefacts. However, depending on the primers used, low or medium stringency conditions may also be employed.

Alternatively, a library may be screened directly such as using oligonucleotides set forth in SEQ ID NO:7 or SEQ ID NO:8 or a mixture of both oligonucleotides may be used. In addition, one or more of oligonucleotides defined in SEQ ID NO:2 to 11 may also be used.

Preferably, the nucleic acid library is a cDNA, genomic, cDNA expression or mRNA library.

Preferably, the nucleic acid library is a cDNA expression library.

Preferably, the nucleotide data base is of human or murine origin and of brain, liver, kidney, neo-natal tissue, embryonic tissue, tumour or cancer tissue origin.

Preferred percentage similarities to the reference nucleotide sequences include at least about 70% more preferably at least about 80%, still more preferably at least about 90% and even more preferably at least about 95% or above.

Another aspect of the present invention provides an isolated nucleic acid molecule comprising a sequence of nucleotides encoding a novel haempoietin receptor or derivative thereof having an amino acid sequence as set forth in SEQ ID NO:13 or having at least about 50% similarity to all or part thereof.

Still yet another aspect of the present invention provides an isolated nucleic acid molecule comprising a sequence of nucleotides encoding a novel haempoietin receptor or derivative thereof having an amino acid sequence as set forth in SEQ ID NO:15 or having at least about 50% similarity to all or part thereof.

Even yet another aspect of the present invention provides an isolated nucleic acid molecule comprising a sequence of nucleotides encoding a novel haempoietin receptor or derivative thereof having an amino acid sequence as set forth in SEQ ID NO:17 or having at least about 50% similarity to all or part thereof.

A further aspect of the present invention provides an isolated nucleic acid molecule comprising a sequence of nucleotides encoding a novel haemopoietin receptor or derivative thereof having an amino acid sequence as set forth in SEQ ID NO:19 or having at least about 50% similarity to all or part thereof.

Even yet a another aspect of the present invention provides an isolated nucleic acid molecule comprising a sequence of nucleotides encoding a novel haempoietin receptor or derivative thereof having an amino acid sequence as set forth in SEQ ID NO:25 or having at least about 50% similarity to all or part thereof.

Another aspect of the present invention provides an isolated nucleic acid molecule comprising a sequence of nucleotides encoding a novel haempoietin receptor or derivative thereof having an amino acid sequence as set forth in one or more of SEQ ID NOs: 29 or having at least about 50% similarity to all or part thereof.

Still another aspect of the present invention provides an isolated nucleic acid molecule comprising a sequence of nucleotides encoding a novel haemopoietin receptor or derivative thereof having an amino acid sequence as set forth in one or more of SEQ ID NOs: 44 or having at least about 50% similarity to all or part thereof.

Preferably, the percentage amino acid similarity is at least about 60%, more preferably at least about 70%, even more preferably at least about 80–85% and still even more preferably at least about 90–95% or greater.

The NR6 polypeptide contemplated by the present invention includes, therefore, derivatives which are components, parts, fragments, homologues or analogues of the novel haempoietin receptors which are preferably encoded by all or part of a nucleotide sequences substantially set forth in SEQ ID NO:12 or 14 or 16 or 18 or 25 or 20 or 24 or 28 or 38 or 43 or a molecule having at least about 60% nucleotide similarity to all or part thereof or a molecule capable of hybridising to the nucleotide sequence set forth in SEQ ID NO:12 or 14 or 16 or 18 or 20 or 24 or 28 or 38 or 43 or a complementary form thereof. The NR6 molecule may be glycosylated or non-glycosylated. When in glycosylated form, the glycosylation may be substantially the same as naturally occurring haempoietin receptor or may be a modified form of glycosylation. Altered or differential glycosylation states may or may not affect binding activity of the novel receptor.

The NR6 haemopoietin receptor may be in soluble form or may be expressed on a cell surface or conjugated or fused to a solid support or another molecule.

As stated above, the present invention further contemplates a range of derivatives of NR6. Derivatives include fragments, parts, portions, mutants, homologues and analogues of the NR6 polypeptide and corresponding genetic sequence. Derivatives also include single or multiple amino acid substitutions, deletions and/or additions to N6 or single or multiple nucleotide substitutions, deletions and/or additions to the genetic sequence encoding NR6. "Additions" to amino acid sequences or nucleotide sequences include fusions with other peptides, polypeptides or proteins or fusions to nucleotide sequences. Reference herein to "NR6" includes reference to all derivatives thereof including functional derivatives or NR6 immunologically interactive derivatives.

Analogues of NR6 contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-titrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

These types of modifications may be important to stabilise NR6 if administered to an individual or for use as a diagnostic reagent.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

TABLE 1

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocycloptopane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |

TABLE 1-continued

| Non-conventional amino acid | Code | Non-conventional amino acid | Code |
|---|---|---|---|
| D-α-methylisoleucine | Dmile | N-amino-α-methylbutyrate | Nmaabu |
| D-αmethylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyerhyl)glycine | Nglu |
| D-α-methy7lproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhn |
| D-N-methylcysteine | Dnmcys | N-(3,3-diphenylpropyl)glycine | Nbhe |
| D-N-methylglutamine | Dnmgln | N-(-3-guanidinopropyl)glycine | Narg |
| D-N-methylglutamate | Dnmglu | N-(1-hydroxyethyl)glycine | Nrhr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-meyhylpropyl)glycine | Nile | D-N-methylserine | Dnmser |
| N-(2-methylpropyl)glycine | Nleu | D-N-methyltheronine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhpbe |
| L-α-methylisoleucine | Mile | N-(2-methylthioethyl)glycine | Nmer |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

The present invention further contemplates chemical analogues of NR6 capable of acting as antagonists or agonists of NR6 or which can act as functional analogues of NR6. Chemical analogues may not necessarily be derived from NR6 but may share certain conformational similarities. Alternatively, chemical analogues may be specifically designed to mimic certain physiochemical properties of NR6. Chemical analogues may be chemically synthesised or may be detected following, for example, natural product screening.

The identification of NR6 permits the generation of a range of therapeutic molecules capable of modulating expression of NR6 or modulating the activity of NR6. Modulators contemplated by the present invention includes agonists and antagonists of NR6 expression. Antagonists of NR6 expression include antisense molecules, ribozymes and co-suppression molecules. Agonists include molecules which increase promoter ability or interfere with negative regulatory mechanisms. Agonists of NR6 include molecules which overcome any negative regulatory mechanism. Antagonists of NR6 include antibodies and inhibitor peptide fragments.

Other derivatives contemplated by the present invention include a range of glycosylation variants from a completely unglycosylated molecule to a modified glycosylated molecule. Altered glycosylation patterns may result from expression of recombinant molecules in different host cells.

Another embodiment of the present invention contemplates a method for modulating expression of NR6 in a subject such as a human or mouse, said method comprising contacting the genetic sequence encoding NR6 with an effective amount of a modulator of NR6 expression for a time and under conditions sufficient to up-regulate or down-regulate or otherwise modulate expression of NR6. Modulating NR6 expression provides a means of modulating NR6-ligand interaction or NR6 stimulation of cell activities.

Another aspect of the present invention contemplates a method of modulating activity of NR6 in a human, said method comprising administering to said mamma a modulating effective amount of a molecule for a time and under conditions sufficient to increase or decrease NR6 activity. The molecule may be a proteinaceous molecule or a chemical entity and may also be a derivative of NR6 or its ligand or a chemical analogue or truncation mutant of NR6 or its ligand.

The present invention, therefore, contemplates a pharmaceutical composition comprising NR6 or a derivative thereof or a modulator of NR6 expression or NR6 activity and one or more pharmaceutically acceptable carriers and/or diluents. These components are referred to as the "active ingredients".

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof, and vegetable oils. The proper fluidity can be maintained, for example, by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ug and 2000 mg of active compound. Alternative dosage amounts include from about 1 µg to about 1000 mg and from about 10 µg to about 500 mg.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules maybe coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels as well as a range of "paints" which are applied to skin and through which the active ingredients are absorbed.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

Dosages may also be expressed per body weight of the recipient. For example, from about 10 ng to about 1000 mg/kg body weight, from about 100 ng to about 500 mg/kg body weight and for about 1 µg to above 250 mg/kg body weight may be administered.

The pharmaceutical composition may also comprise genetic molecules such as a vector capable of transfecting target cells where the vector carries a nucleic acid molecule capable of modulating NR6 expression or NR6 activity. The vector may, for example, be a viral vector.

Still another aspect of the present invention is directed to antibodies to NR6 and its derivatives. Such antibodies may be monoclonal or polyclonal and may be selected from naturally occurring antibodies to NR6 or may be specifically raised to NR6 or derivatives thereof In the case of the latter, NR6 or its derivatives may first need to be associated with a carrier molecule. The antibodies and/or recombinant NR6 or its derivatives of the present invention are particularly useful as therapeutic or diagnostic agents. For example, NR6 antibodies or antibodies to its ligand may act as antagonists.

For example, NR6 and its derivatives can be used to screen for naturally occurring antibodies to NR6. These may occur, for example in some autoimmune diseases. Alternatively, specific antibodies can be used to screen for NR6. Techniques for such assays are well known in the art and include, for example, sandwich assays and ELISA. Knowledge of NR6 levels may be important for diagnosis of certain cancers or a predisposition to cancers or for monitoring certain therapeutic protocols.

Antibodies to NR6 of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regimen.

For example, specific antibodies can be used to screen for NR6 proteins. The latter would be important, for example, as a means for screening for levels of NR6 in a cell extract or other biological fluid or purifying NR6 made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of NR6.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of NR6, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting NR6 in a biological sample from a subject said method comprising contacting said biological sample with an antibody specific for NR6 or its derivatives or homologues for a time and under conditions sufficient for an antibody-NR6 complex to form, and then detecting said complex.

The presence of NR6 may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabeled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is one which might contain NR6 including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the NR6 or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes or overnight if more convenient) and under suitable conditions (e.g. from about room temperature to about 37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

In another alternative method, the NR6 ligand is immobilised to a solid support and a biological sample containing NR6 brought into contact with its immobilised ligand. Binding between NR5 and its ligand can then be determined using an antibody to NR6 which itself may be labelled with a reporter molecule or a further anti-immunoglobulin antibody labelled with a reporter molecule could be used to detect antibody bound to NR6.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect the NR6 gene or its derivatives. Alternative methods or methods used in conjunction include direct nucleotide sequencing or mutation scanning such as single stranded conformational polymorphisms analysis (SSCP) as specific oligonucleotide hybridisation, as methods such as direct protein truncation tests.

The nucleic acid molecules of the present invention may be DNA or RNA. When the nucleic acid molecule is in a DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli, Bacillus* sp and *Pseudomonas* sp. Preferred eukaryotic cells include yeast, fungal, mammalian and insect cells.

Accordingly, another aspect of the present invention contemplates a genetic construct comprising a vector portion and a mammalian and more particularly a human NR6 gene portion, which NR6 gene portion is capable of encoding an NR6 polypeptide or a functional or immunologically interactive derivative thereof.

Preferably, the NR6 gene portion of the genetic construct is operably linked to a promoter on the vector such that said promoter is capable of directing expression of said NR6 gene portion in an appropriate cell.

In addition, the NR6 gene portion of the genetic construct may comprise all or part of the gene fused to another genetic sequence such as a nucleotide sequence encoding maltose binding protein or glutathione-S-transferase or part thereof.

The present invention extends to such genetic constructs and to prokaryotic or eukaryotic cells comprising same.

The present invention also extends to any or all derivatives of NR6 including mutants, part, fragments, portions, homologues and analogues or their encoding genetic sequence including single or multiple nucleotide or amino acid substitutions, additions and/or deletions to the naturally occurring nucleotide or amino acid sequence.

NR6 may be important for the proliferation, differentiation and survival of a diverse array of cell types. Accordingly, it is proposed that NR6 or its functional derivatives be used to regulate development, maintenance or regeneration in an array of different cells and tissues in vitro and in vivo. For example, NR6 is contemplated to be useful in modulating neuronal proliferation, differentation and survival.

Soluble NR6 polypeptides are also contemplated to be useful in the treatment of a range of diseases, injuries or abnormalities.

Membrane bound or soluble NR6 may be used in vitro on nerve cells or tissues to modulate proliferation, differentiation or survival for example, in grafting procedures or transplantation.

As stated above, the NR6 of the present invention or its functional derivatives may be provided in a pharmaceutical composition comprising the NR6 together with one or more pharmaceutically acceptable carriers and/or diluents. In addition, the present invention contemplates a method of treatment comprising the administration of an effective amount of a NR6 of the present invention. The present invention also extends to antagonists and agonists of NR6s and their use in therapeutic compositions and methodologies.

A further aspect of the present invention contemplates the use of NR6 or its functional derivatives in the manufacture of a medicament for the treatment of NR6 mediated conditions defective or deficient.

Still a further aspect of the present invention contemplates a ligand for NR6 preferably, in isolated or recombinant form or a derivative of said ligand.

The present invention further contemplates knockout animals such as mice or other murine species for the NR6 gene including homozygous and heterozygous knockout animals. Such animals provide a particularly useful live in vivo model for studying the effects of NR6 as well as screening for agents capable of acting as agonists or antagonists of NR6.

According to this embodiment there is provided a transgenic animal comprising a mutation in at least one allele of the gene encoding NR6. Additionally, the present invention provides a transgenic animal comprising a mutation in two alleles of the gene encoding NR6. Preferably, the transgenic animal is a murine animal such as a mouse or rat.

The present invention is further described by the following non-limiting Figures and Examples.

BRIEF DESCRIPTION OF THE DRAWING

In the Figures:

FIG. 1A and FIG. 1B are diagrammatic representations showing expansion of sequenced region of the mouse NR6 gene indicating splicing patterns seen in the three forms of NR6 cDNA, NR6.1, NR6.2 and NR6.3.

FIG. 2 is a representation of the nucleotide sequence of the mouse NR6 gene, containing exons encoding the cDNA from nucleotide 148 encoding D50 of the cDNAs shown in SEQ ID NOs: 12 and 14 to the end of the 3' untranslated region shared by both NR6.1, NR6.2 and NR6.3. In this figure, this region encompasses nucleotides g1182 to g6617. This sequence is also defined in SEQ ID NO:28.

FIG. 3 is a representation of the nucleotide sequence of the mouse genomic NR6 gene with additional 5' sequences. The coding exons of NR6 span approximately 11 kb of the mouse genome. There are 9 coding exons separated by 8 introns:

| | |
|---|---|
| exon1 at least 239 nt | intron1 5195 nt |
| exon2 282 nt | intron2 214 nt |
| exon3 130 nt | intron3 107 nt |
| exon4 170 nt | intron4 1372 nt |
| exon5 158 nt | intron5 68 nt |
| exon6 169 nt | intron6 2020 nt |
| exon6 188 nt | intron7 104 nt |
| exon8 43 nt | intron8 181 nt |
| exon9 252 nt | |

Exon 1 encoding the signal sequence, exon 2 the Ig-like domain, exons 3 to 6 the haemopoietin domain. Exons 7, 8 and 9 are alternatively spliced.

Figure 4:
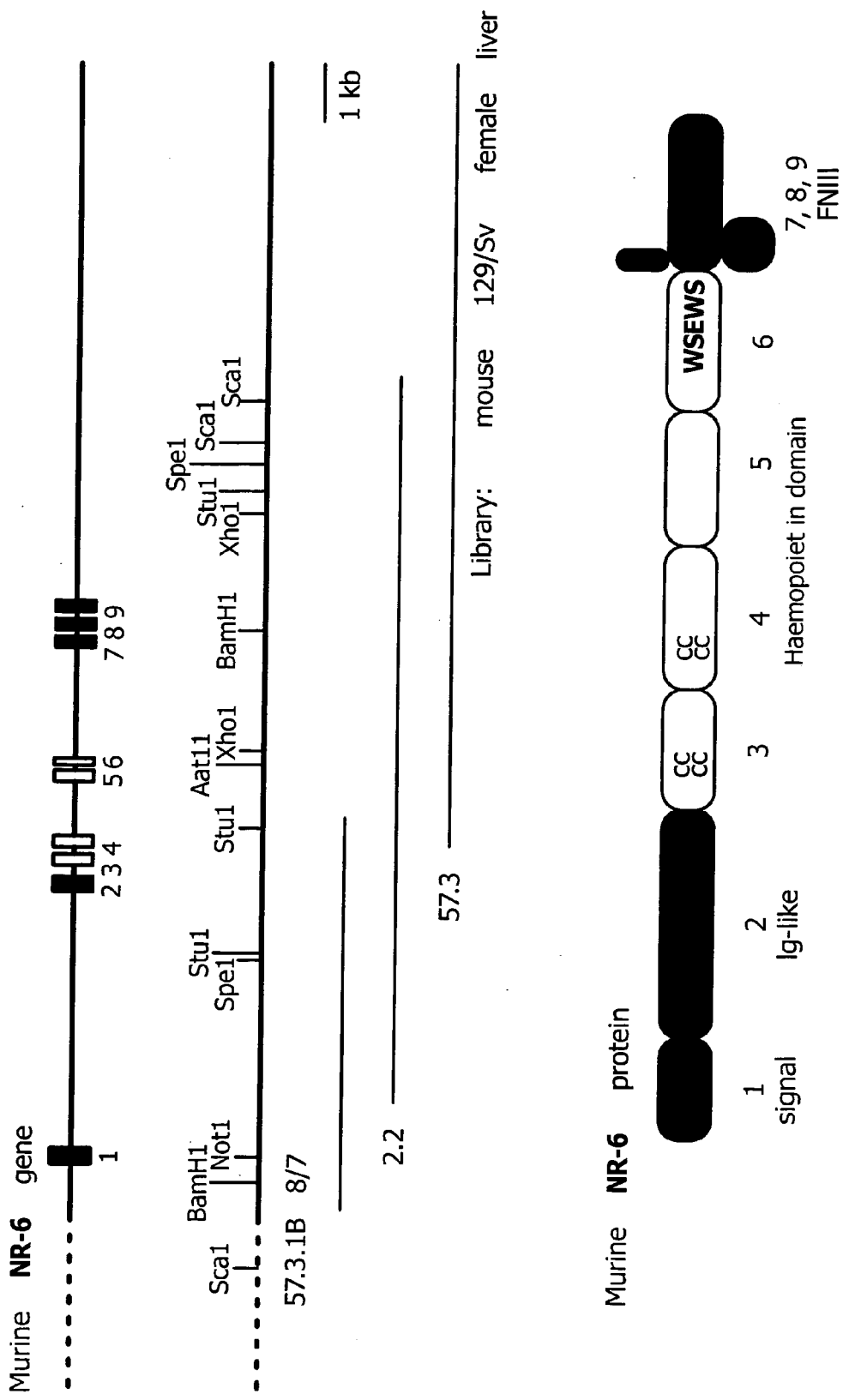

FIG. 4 is a diagrammatic representation showing the genomic structure of murine NR6.

Figure 5:
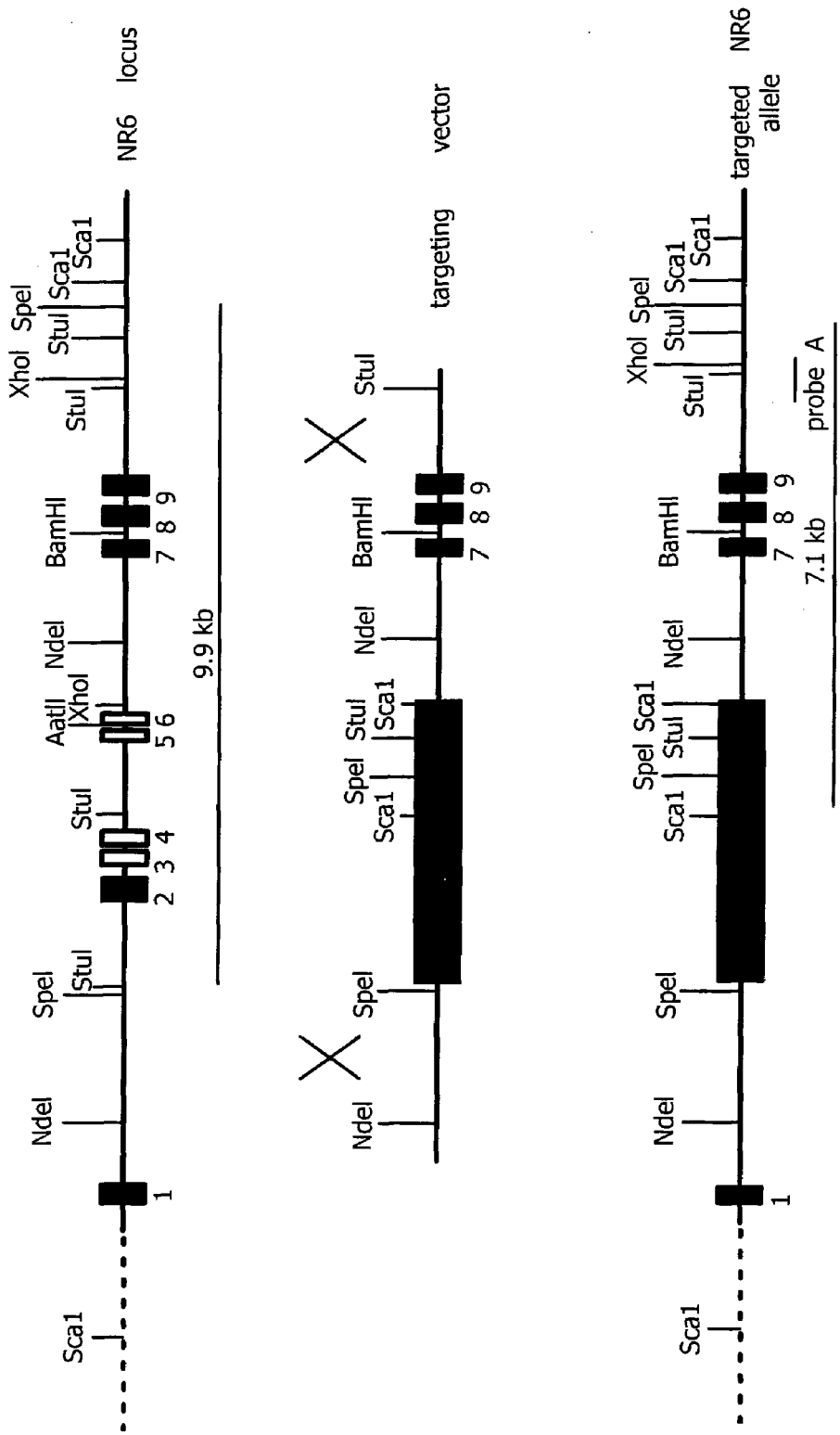

FIG. 5 is a diagrammatic representation showing targetting of the NR6 locus by homologous recombination.

Figure 6(1):
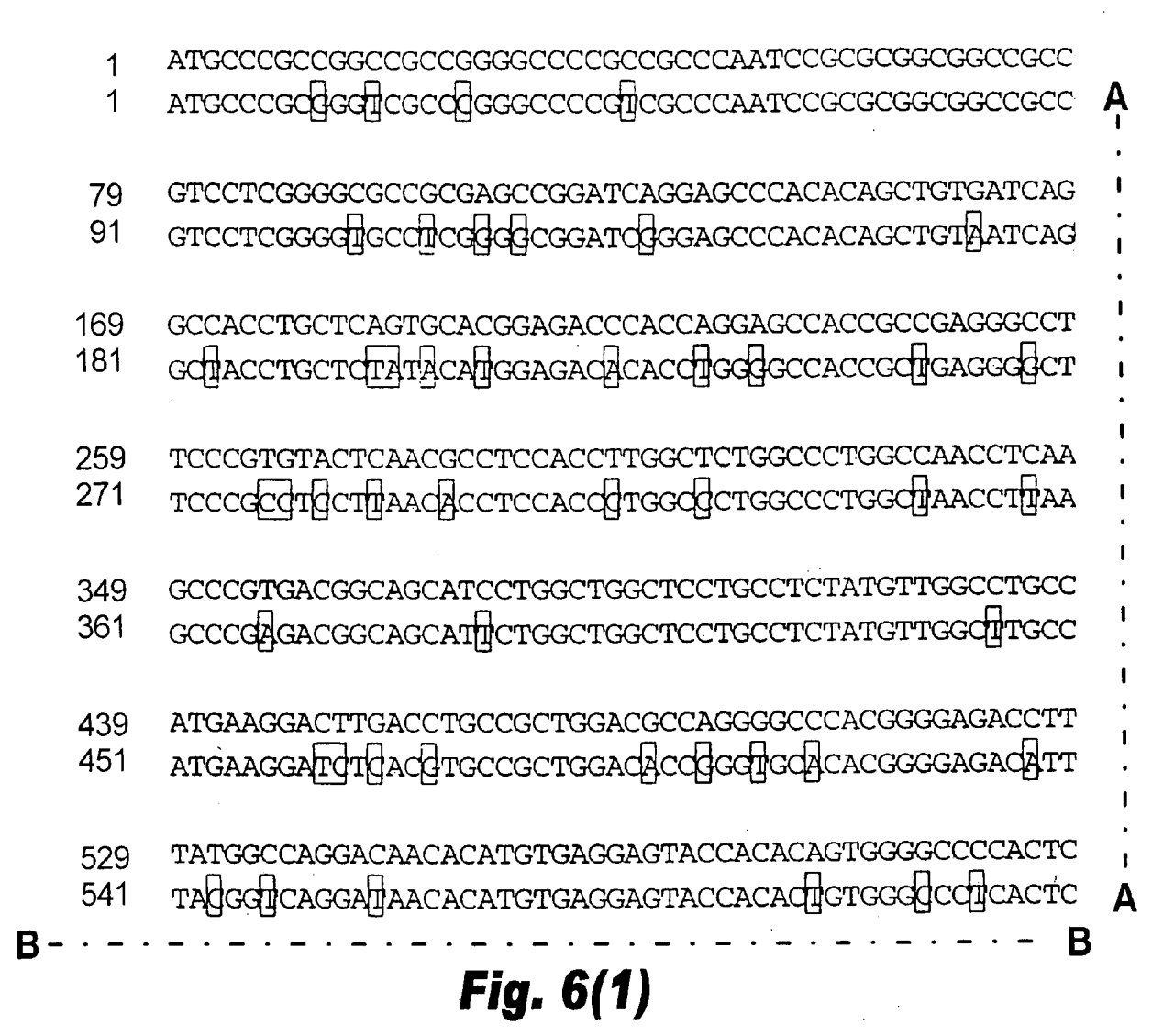

FIG. 6 is a representation of a comparison of human and mouse NR6 cDNA sequences.

FIG. 7 is a representation of a comparison of human and mouse NR6 protein sequences.

FIG. 8 is a representation showing transient expression of C-terminal FLAG tagged human NR6 in 293T cells. (A) Biosensor response, M2 immobilised; (B) SDS PAGE/silver staining analysis of M2 eluted fractions; and (C) Western blot analysis of M2 eluted fractions.

Figure 9:
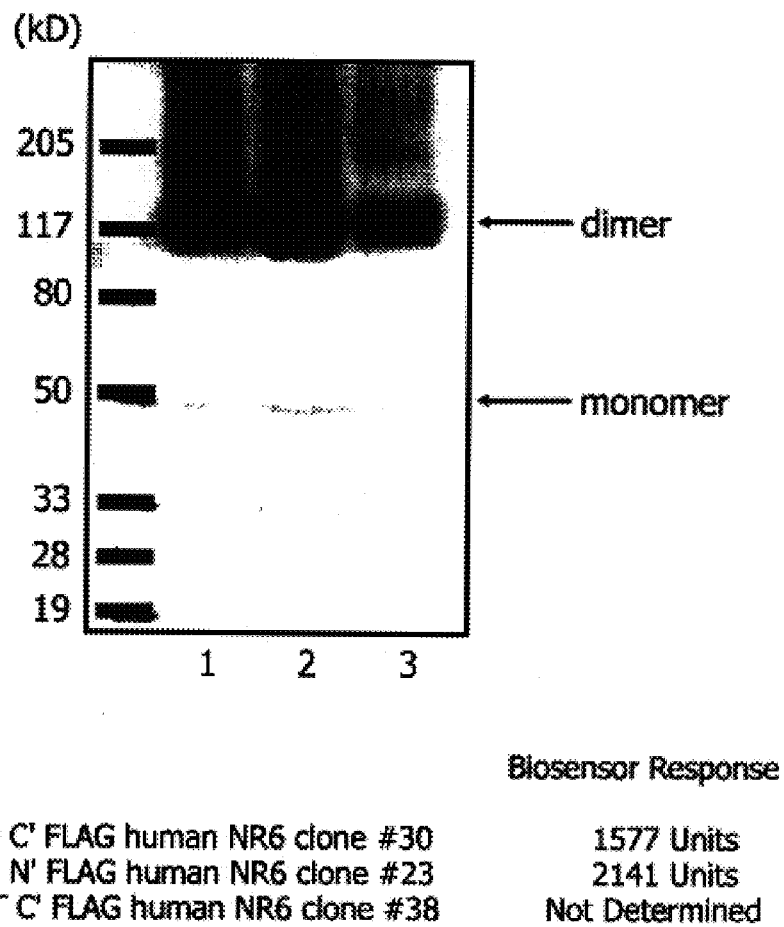

FIG. 9 a photographic representation showing biosensor analysis of supernatant fluid from each of clones CHO C' LAG human NR6 clone #30, CHO N' FLAG human NR6 clone #23 and 293T C' FLAG human NR6 clone #38 (lanes 1–3, respectively).

Single and three letter abbreviations for amino acid residues used in the specification are summarised in Table 2:

TABLE 2

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

TABLE 3

SUMMARY OF SEQ ID NO.

| Sequence | SEQ ID NO. |
|---|---|
| Amino acid sequence WSXWS | 1 |
| Oligonucleotide primers and probes listed in Example 1 | 2–11 |
| Nucleotide sequence of NR6.1[1] | 12 |
| Amino acid sequence of NR6.1 | 13 |
| Nucleotide sequence of NR6.2[2] | 14 |
| Amino acid sequence of NR6.2 | 15 |
| Nucleotide sequence of NR6.3[3] | 16 |
| Amino acid sequence of NR6.3 | 17 |
| Nucleotide sequence of products generated by 5' RACE of brain cDNA using NR6 specific primers[4] | 18 |
| Amino acid sequence of SEQ ID NO:18 | 19 |
| Nucleotide sequence unique to 5' RACE of brain cDNA | 20 |
| Amino acid sequence for SEQ ID NO:20 | 21 |
| Unspliced murine NR6 nucleotide sequence | 22 |
| PCR product for human NR6 | 23 |

TABLE 3-continued

SUMMARY OF SEQ ID NO.

| Sequence | SEQ ID NO. |
|---|---|
| Nucleotide sequence of clone HFK-66 encoding human NR6 | 24 |
| Amino acid sequence of SEQ ID NO:24 | 25 |
| Oligonucleotide sequences UPI and LPI, respectively | 26–27 |
| Genoinic nucleotide sequence of murine NR6 | 28 |
| Amino acid sequence of SEQ ID NO:28 | 29 |
| Murine NR6.1 oligonucleotide primers | 30,31 |
| Murine IL-3 signal sequence | 32 |
| Linker sequence for mouse IL-3 signal sequence and FLAG epitope | 33–35 |
| Genoinic nucleotide sequence of murine NR6 containing additonal 5' sequence | 38 |
| Oligonucleotide 2199 and 2200, respectively | 36–37 |
| N-terminal region of NR6 | 39 |
| Oligonucleotide sequences | 40–42 |
| Nucleotide sequence of NR6 | 43 |
| Amino acid sequence of NR6 | 44 |
| Oligonucleotide sequences | 45–54 |

[1] The Polyadenylation signal AATAAATAAA (SEQ ID NO:58) is at nucleotide position 1574 to 1583 of SEQ ID NO:12; the coding sequences of NR6.1 (SEQ ID NO:12) and NR6.2 (SEQ ID NO:14) are identical to the codon encoding Q407, which represents the end of an exon. NR6.1 splices out an exon present only in NR6.2 and uses a different reading frame for the final exon which is shared with NR6.2; this corresponds to amino acids VLPAKL at amino acid residue positions 408–413 of SEQ ID NO:13. The region of 3'-untranslated DNA shared by NR6.1, NR6.2, and NR6.3 is from nucleotide 1363 to 1598 of SEQ ID NO:12. The WSXWS motif is at amino acid residues 330 to 335 of SEQ ID NO:13.
[2] The polyadenylation signal AATAAATAAA (SEQ ID NO:58) is at nucleotide positions 1618 to 1627 of SEQ ID NP:14. The WSXWS motif is amino acid residues 330 to 334 of SEQ ID NO:15. NR6.1 and NR6.2 are identified to the codon encoding Q407 which represents the end of an exon. NR6.2 splices in an exon beginning at nucleotide 1348 and ends at nucleotide 1388 of SEQ ID NO:14 (corresponding to the coding sequence for amino acid residue D408 to residue G422 of SEQ ID NO:15). The region of 3' untranslated DNA shared by NR6.1, NR6.2 and NR6.3 is from nucleotide position 1407 to 1641 of SEQ ID NO:14.
[3] The WSXWS motif is at amino acid residues 24–28 of SEQ ID NO:17. The polyadenylation signal AATAAATAAA (SEQ ID NO:58) is from nucleotide 863 to 872 of SEQ ID NO:16. Amino acids 1–101 of NR6.3 (SEQ ID NO:17) are identical to amino acids 307–407 of NR6.1 (SEQ ID NO:13) and NR6.2 (SEQ ID NO:15). The codon encoding Q407 of SEQ ID NO:13 or Q101 of SEQ ID NO:17 represents the end of an exon. NR6.3 fails to splice from this position and, therefore, translation continues through the intron, giving rise to the C-termianl protein region from amino acid residues 102–155 of SEQ ID NO:17. The region of 3' untranslated DNA shared by NR6.1, NR6.2 and NR6.3 is from nucleotide 650–887 of SEQ ID NO 16.
[4] The nucleotide sequence is identical to NR6.1, NR6.2, and NR6.3 from nucleotide C151, the first nucleotide from Pro51. The numbering from the nucleotide is the same as for SEQ ID NO:14 and 16. The 5' of this point is unique to the products generated by 5' RACE not being found in NR6.1, NR6.2 and NR6.3 and is represented in SEQ ID NOs:20 and 21.

TABLE 3-continued

SUMMARY OF SEQ ID NO.

| Sequence | SEQ ID NO. |
|---|---|
| [5] Structure of the murine genomic NR6 locus. The coding exons of NR6 span approximately 11 kb of the mouse genome. There are 9 coding exons separated by 8 introns. | |

| | |
|---|---|
| exon1 at least 239 nt | intron1 5195 nt |
| exon2 282 nt | intron2 214 nt |
| exon3 130 nt | intron3 107 nt |
| exon4 170 nt | intron4 1372 nt |
| exon5 158 nt | intron5 68 nt |
| exon6 169 nt | intron6 2020 nt |
| exon7 188 nt | intron7 104 nt |
| exon8 43 nt | intron8 181 nt |
| exon9 252 nt | |

Exon 1 encodes the signal sequence, exon 2 the Ig-like domain, exons 3 to 6 the hemopoietin domain. Exons 7, 8 and 9 are alternatively spliced.

The NRG molecules of the present invention have a range of utilities referred to in the subject specification. Additional utilities include:

1. Identification of molecules that interact with NR6. These may include:

a) a corresponding ligand using standard orphan receptor techniques (26), b) monoclonal antibodies that act either as receptors antagonists or agonists, c) mimetic or antagonistic peptides isolated using phage display technology (27,28), d) small molecule natural products that act either as antagonists or agonists.

2. Development of diagnostics to detect deletions/rearrangements in the NR6 gene.

The NR6 knock-out mice studies described herein provide a useful model for this utility. There are also applications in the field of reproduction. For example, people can be tested for their NR6 status. NR6+/– carriers might be expected to give rise to offspring with developmental problems.

EXAMPLE 1

Oligonucleotides

| | | | |
|---|---|---|---|
| M116: | 5' | ACTCGCTCCAGATTCCCGCCTTTT 3' | [SEQ ID NO:2] |
| M108: | 5' | TCCCGCCTTTTTCGACCCATAGAT 3' | [SEQ ID NO:3] |
| M159: | 5' | GGTACTTGGCTTGGAAGAGGAAAT 3' | [SEQ ID NO:4] |
| M242: | 5' | CGGCTCACGTGCACGTCGGGTGGG 3' | [SEQ ID NO:5] |
| M112: | 5' | AGCTGCTGTTAAAGGGCTTCTC 3' | [SEQ ID NO:6] |
| WSDWS | 5' | (A/G)CTCCA(A/G)TC(A/G)CTCCA 3' | [SEQ ID NO:7] |
| WSEWS | 5' | (A/G)CTCCA(C/T)TC(A/G)CTCCA 3' | [SEQ ID NO:8] |
| 1944 | 5' | AAGTGTGACCATCATGTGGAC 3' | [SEQ ID NO:9] |

-continued 2106  5' GGAGGTGTTAAGGAGGCG 3'   [SEQ ID NO:10]

2120  5' ATGCCCGCGGGTCGCCCG 3'   [SEQ ID NO:11]

EXAMPLE 2

Isolation of Initial NR6 cDNA Clones Using Oligonucleotides Designed Against the Conserved WSXWS Motif Found in Members of the Haemopoietin Receptor Family (i) A commercial adult mouse testis cDNA library cloned into the UNI-ZAP bacteriophage (Stratagene, Calif., USA; Catalogue numbers 937 308) was used to infect *Escherichia coli* of the strain LE392. Infected bacteria were grown on twenty 150 mm agar plates, to give approximately 50,000 plaques per plate. Plaques were then transferred to duplicate 150 mm diameter nylon membranes (Colony/Plaque Screen, NEN Research Products, Mass., USA), bacteria were lysed and the DNA was denatured and fixed by autoclaving at 100° C. for 1 min with dry exhaust. The filters were rinsed twice in 0.1% (w/v) sodium dodecyl sulfate (SDS), 0.1×SSC (SSC is 150 mM sodium chloride, 15 mM sodium citrate dihydrate) at room temperature and pre-hybridized overnight at 42° C. in 6×SSC containing 2 mg/ml bovine serum albumin, 2 mg/ml Ficoll 2 mg/ml polyvinylpyrrolidone, 100 mM ATP, 10 mg/ml tRNA, 2 mM sodium pyrophosphate, 2 mg/ml salmon sperm DNA, 0.1% (w/v) SDS and 200 mg/ml sodium azide. The pre-hybridisation buffer was removed. 1.2 μg of the degenerate oligonucleotides for hybridizaton (WSDWS; Example 1) were phosphorylated with T4 polynucleotide kinase using 960 mCi of $y^{32}$P-ATP (Bresatec, S. A., Australia). Unincorporated ATP was separated from the labelled oligonucleotide using a pre-packed gel filtration column (NAP-5; Pharmacia, Uppsala, Sweden). Filters were hybridized overnight at 42° C. in 80 ml of the prehybridisation buffer containing 0.1%(w/v) SDS, rather than NP40, and $10^6$–$10^7$ cpm/ml of labelled oligonucleotide. Filters were briefly rinsed twice at room temperature in 6×SSC, 0.1%(v/v) SDS, twice for 30 min at 45° C. in a shaking waterbath containing 1.5 l of the same buffer and then briefly in 6×SSC at room temperature. Filters were then blotted dry and exposed to autoradiographic film at −70° C. using intensifying screens, for 7–14 days prior to development.

Plaques that appeared positive on orientated duplicate filters were picked, eluted in 1 ml of 100 mM NaCl, 10 mM MgCl$_2$, 10 mM Tris.HCl pH7.4 containing 0.5%(w/v) gelatin and 0.5% (v/v) chloroform and stored at 4° C. After 2 days LE392 cells were infected with the eluate from the primary plugs and replated for the secondary screen. This process was repeated until hybridizing plaques were pure.

Once purified, positive cDNAs were excised from the ZAP II bacteriophage according to the manufacturer's instructions (Stratagene, Calif., USA) and cloned into the plasmid pBluescript. A CsCl purified preparation of the DNA was made and this was sequenced on both strands. Sequencing was performed using an Applied Biosystems automated DNA sequencer, with fluorescent dideoxynucleotide analogues according to the manufacturer's instructions. The DNA sequence was analysed using software supplied by Applied Biosystems.

Two clones isolated from the mouse testis cDNA library shared large regions of nucleotide sequence identity 68-1 and 68-2 and appeared to encode a novel member of the haemopoietin receptor family and the inventors gave the putative receptor the working name "NR6".

(ii) In a parallel series of experiments, a commercial mouse brain cDNA library (STRATAGENE #967319, Balb/c day-20, whole brain cDNA/Uni-ZAP XR Vector) was used to infect *E. coli* strain XL1-Blue MRF'. Infected bacteria were grown on 90×135 mm square agar plates to give about 25,000 plaques per plate. Plaques were then transferred to positively charged nylon membranes, Hybond-N(+) (Amersham RPN 203B), bacteria were lysed and the DNA was denatured with denaturing 0.5 M NaOH, 1.5 M NaCl at room temperature for 7 min. The membranes were neutralized with 0.5 M Tris-HCl pH7.2, 1.5 M NaCl, 1 mM EDTA at room temperature for 10 min before the DNA fixation by UV crosslinking.

A mixture of WSDWS and WSEWS oligonucleotide probes (SEQ ID NOs: 7 and 8) were labelled with a [α-$^{32}$P]-ATP (TOYOBO #PNK-104 Kination kit). The membranes from the mouse brain cDNA library were then hybridized with the mixture of WSDWS and WSEWS oligonucleotide probes in the Rapid Hybridization Buffer (Amersham, RPN1636) at 42° C. for 16 hours. Filters were washed with 1×SSC/0.1% (w/v) SDS at 42° C. before autoradiography. Plaques that appeared positive on orientated duplicate filters were picked and replated on *E. coli*, XL1-Blue MRF' with the process of immobilization on nylon membranes, hybridization of membranes with oligonucleotide probes, washing and autoradiography repeated until pure plaques had been obtained.

The cDNA fragment from pure positively hybridizing plaques was isolated by excision with the helper phage strain ExAssist according to the manufacturer's instructions (Stratagene, #967319). Sequencing was performed after the amplification with Ampli-Taq DNA polymerase and Taq dideoxy terminator cycle sequencing kit (Perkin Elmer, #401150) by 25 cycles of 96° C. for 10 sec, 50° C. for 5 sec, 60° C. for 4 min followed by 60° C. for 5 min with the sequencing primers on an ABI model 377 DNA sequencer.

One clone, MBC-8, from the mouse brain library shared large regions of nucleotide sequence identity with both the 68-1 and 68-2 clones isolated from the mouse testis cDNA library.

(iii) In a third series of experiments, total RNA was prepared from the mouse osteoblastic cell line, KUSA, according to the method of Chirgwin et al. (15), and poly (A)+RNA was further purified by oligo(dT)-cellulose chromatography (Pharmacia Biotech). Complementary DNA was synthesized by oligo(dT) priming, inserted into the UniZAP XR directional cloning vector (Stratagene), and packaged into λ phage using Gigapack Gold (Stratagene), yielding 1.25×$10^7$ independent clones.

Approximately $10^6$ clones were screened essentially as described in (ii) above. Briefly, probes were labeled with $^{32}$P using T4 polynucleotide kinase and prehybridization was performed for 4 hr in the Rapid hybridization buffer (Amersham LIFE SCIENCE) at 42° C. Filters (Hybond N+, Amersham) were then hybridized for 19 hr under the same condition with the addition of $^{32}$P-labeled WSXWS mix oligonucleotides and washed 3 times. The final wash was for 30 min in 1×SSPE, 0.1% (w/v) SDS at 42° C. Filters were then exposed with an intensifying screen to Kodak X-OMAT AR film for 5 days.

Isolated clones were subjected to the in vivo excision of pBluescript SK(−) phagemid (Stratagene), and plasmid DNA was prepared by the standard method. DNA sequences were determined using an ABI PRISM 377 DNA Sequencer (Perkin Elmer) with appropriate synthetic oligonucleotide primers. A clone pKUSA166 shared large regions of nucleotide sequence identity with the MBC-8, 68-1 and 68-2 clones isolated from the mouse brain and testis cDNA libraries.

EXAMPLE 3

Isolation of Further NR6 cDNA Clones Using Probes Specific for NR6

(i) In order to identify other cDNA libraries containing cDNA clones for NR6, the inventors performed PCR upon 1 µl aliquots of λ-bacteriophage cDNA libraries made from mRNA from various human tissues and using oligonucleotides 2070 and 2057, designed from the sequence of 68-1 and 68-2, as primers. Reactions contained 5 µl of 10× concentrated PCR buffer (Boehringer Mannheim GmbH, Mannheim, Germany), 1 µl of 10 mM dATP, dCTP, dGTP and dTTP, 2.5 µl of the oligonucleotides HYB2 and either T3 or T7 at a concentration of 100 mg/ml, 0.5 µl of Taq polymerase (Boehringer Mannheim GmbH) and water to a final volume of 50 µl. PCR was carried out in a Perkin-Elmer 9600 by heating the reactions to 96° C. for 2 min and then for 25 cycles at 96° C. for 30 sec, 55° C. for 30 sec and 72° C. for 2 min. PCR products were resolved on an agarose gel, immobilized on a nylon membrane and hybridized with $^{32}$P-labelled oligonucleotide 1943 (SEQ ID NO:42).

In addition to the original library, a mouse brain cDNA library appeared to contain NR6 cDNAs. These were screened using a $^{32}$P-labelled oligonucleotides 1944, 2106, 2120 (Example 1) or with a fragment of the original NR6 cDNA clone from 68-1 (nucleotide 934 to the end of NR6.1 in FIG. 1) labelled with $^{32}$P using a random decanucleotide labelling kit (Bresatec). Conditions used were similar to those described in (i) above except that for the labelled oligonucleotides, filters were washed at 55° C. rather than 45° C., while for the NR6 cDNA fragment prehybridization and hybridization was carried out in 2×SSC and filters were washed at 0.2×SSC at 65° C. Again, as described in (i) above, positively hybridising plaques were purified, the cDNAs were recovered and cloned into plasmids pBluescript II or pUC19. Independent cDNA clones were sequenced on both strands.

Using this procedure, 6 further clones, 68-5, 68-35, 68-41, 68-51, 68-77 and 73-23, contained large regions of sequence identity with 68-1, 68-2, MBC-8 and pKUSA166.

In a parallel series of experiments, further screening was performed with hybridization probes prepared from the 1.7 kbp EcoRI-XhoI fragment excised from pKUSA166. This fragment was excised and labeled with $^{32}$P by using T7QuickPrime Kit (Pharmacia Biotech). Approximately 6×10$^5$ clones were screened. Hybond N+ filters (Amersham) were first prehybridized for 4 hr at 42° C. in 50% (v/v) formamide, 5×SSPE, 5×Denhardt's solution, 0.1% (w/v) SDS, and 0.1 mg/ml denatured salmon sperm DNA. Hybridization was for 16 hours under the same conditions with the addition of $^{32}$P-labelled NR6-cDNA fragment probes. Finally the filters were washed once for 1 hr in 0.2×SSC, 0.1% (w/v) SDS at 68° C. Eight clones were isolated, and phage clones were subjected to the in vivo excision of the pBluescript SK(−) phagemid (Stratagene). The plasmid DNAs were prepared by the standard method. DNA sequences were determined by an ABI PRISM 377 DNA Sequencer using appropriate synthetic oligonucleotide primers.

Using this procedure 8 further clones from the KUSA library contained large regions of sequence identity with 68-1, 68-2, MBC-8, pKUSA166, 68-5, 68-35, 68-41, 68-51, 68-77 and 73-23 were isolated.

EXAMPLE 4

Isolation of Genomic DNA Encoding NR6

DNA encoding the murine NR6 genomic locus was also isolated using the 68-1 cDNA as a probe. Two positive clones, 2-2 and 57-3, were isolated from a mouse 129/Sv strain genomic DNA library cloned into λ FIX. These clones were overlapping and the position of the restriction sites, introns and exons were determined in the conventional manner. The region of the genomic clones containing exons and the intervening introns were sequenced on both strands using an Applied Biosystems automated DNA sequencer, with fluorescent dideoxynucleotide analogues according to the manufacturer's instructions. FIG. 2 shows the nucleotide sequence and corresponding amino acid sequence of the translation regions. This is also shown in SEQ ID NOs:30 and 31. FIG. 3 provides the genomic NR6 gene sequence but with additional 5' sequence. This is also represented in SEQ ID NO:38 in relation to this sequence. The coding exons of NR6 span approximately 11 kb of the mouse genome. There are 9 coding exons separated by 8 introns:

| exon1 at least 239 nt | intron1 5195 nt |
| exon2 282 nt | intron2 214 nt |
| exon3 130 nt | intron3 107 nt |
| exon4 170 nt | intron4 1372 nt |
| exon5 158 nt | intron5 68 nt |
| exon6 169 nt | intron6 2020 nt |
| exon7 188 nt | intron7 104 nt |
| exon8 43 nt | intron8 181 nt |
| exon9 252 nt | |

Exon 1 encodes the signal sequence, exon 2 the Ig-like domain, exons 3 to 6 the hemopoietin domain. Exons 7, 8 and 9 are alternatively spliced.

EXAMPLE 5

5' RACE Analysis of NR6

5'-RACE was used to investigate the nature of the sequence 5' of nucleotide 960, encoding Ile321 of NR6.1, 2 and 3. The nucleotide and corresponding amino acid sequences are shown in SEQ ID NOs: 12, 14 and 16, respectively. 5'-RACE was performed using Advantage KlenTaq polymerase (CLONTECH, CAT NO. K1905-1) on mouse brain Marathon-ready cDNA (CLONTECH, CAT NO. 7450-1) according to the manufacturer's instructions. Briefly, the first rounds of amplification were performed using 5 µl of cDNA in a total volume of 50 µl, with 1 mM each of the primers AP1&M116 [SEQ ID NO:2] or AP1&M159 [SEQ ID NO:4] by 35 cycles of 94° C.×0.5 min, 68° C.×2.0 min on GeneAmp 2400 (Perkin-Elmer). An amount of 5 µl of 50-fold diluted product from the first amplification was then re-amplified; for the products generated with primers AP1 and M116 [SEQ ID NO:2] in the first amplification, 1 mM of the primers AP2&M108 [SEQ ID NO:3] were used in the second amplification. For the products generated with primers AP1 and M116 [SEQ ID NO:2] in the first amplification, two separate secondary reactions were performed, one reaction with 1 mM primers AP2&M242 [SEQ ID NO:5] and the other with 1 mM primers AP2&M112 [SEQ ID NO:6]. Amplification was achieved using 25 cycles of 94° C.×0.5 min, 68° C.×2.0 min. These samples were analyzed by agarose gel electrophoresis. When a single ethidium bromide staining amplification product was observed, it was purified by QIAquick PCR purification kit according to the manufacturer's instructions (QIAGEN, CAT NO. DG-0281) and its sequence was directly determined using both primers used in the secondary amplification step, that is AP2 and either M108 [SEQ ID NO:3], M242 [SEQ ID NO:5] or M112 [SEQ ID NO:6].

EXAMPLE 6

Cloning of NR6

From the initial screens of mouse brain and testis cDNA libraries with the degenerate WSXWS oligonucleotides and subsequent screening of cDNA libraries from mouse testis, mouse brain and the KUSA osteoblastic cells line a total of 18 NR6 cDNAs have been isolated. Nucleotide sequence of NR6 was also determined from 5'RACE analysis of brain cDNA. Additionally, two murine genomic DNA clones encoding NR6 have also been isolated.

Comparison of the NR6 cDNA clones revealed a common region of nucleotide sequence which included a 123 base pairs 5'-untranslated region and 1221 base pairs open reading frame, stretching from the putative initiation methionine, Met1 to Gln407 (SEQ ID NOs: 12, 14 and 16, respectively). Within this common open reading frame, a haemopoietin receptor domain was observed which contained the four conserved cysteine residues and the five amino acid motif WSXWS typical of members of the haemopoietin receptor family, was observed.

Further analyses revealed that after nucleotide 1221, three different classes of NR6 cDNAs could be found, these were termed NR6.1, NR6.2 and NR6.3 (SEQ ID NOs:12, 14 and 16, respectively). Each encoded a receptor that appeared to lack a classical transmembrane domain and, would, therefore be likely to be secreted into the extracellular environment. Although the putative C-terminal region of the three classes of NR6 proteins appear to be different, the cDNAs encoding them also had a common region of 3'-untranslated region.

With regard to SEQ ID NOs:12, 14 and 16, the number of both nucleotides and amino acids begins at the putative initiation methione. NR6.1 and NR6.2 are identical to nucleotide 1223 encoding Q407, this represents the end of an exon. NR6.1 splices out an exon present only in NR6.2 and uses a different reading frame for the final exon which is shared with NR6.2. The 3'-untranslated region is shared by NR6.1, NR6.2 and NR6.3, NR6.2 splices in an exon starting with nucleotide 1224 encoding D408 and ending with nucleotide 1264 encoding the first nucleotide in the codon for G422 and uses a different reading frame for the final exon which is shared with NR6.2 (see FIG. 1). NR6.3 fails to splice from position nucleotide 1224, therefore, translation continues through the intron, giving rise to the C-terminal protein region.

The sequence of NR6 cDNA products generated by 5'-RACE amplification from mouse brain cDNA preparation is shown in SEQ ID NO:18. The nucleotide sequence identified using 5'-RACE appeared to be identical to the sequence of cDNAs encoding NR6.1, NR6.2, and NR6.3 from nucleotide C151, the first nucleotide for the codon for Pro51. 5' of this nucleotide, the sequences diverged and the sequence is unique not being found in NR6.1, NR6.2 or NR6.3. Additionally, there is a single nucleotide difference, with the sequence from the RACE containing an G rather than an A at nucleotide 475, resulting in Thr159 becoming Ala.

Analysis of the genomic clones, revealed that they were overlapping and contained exons encoding the majority of the coding region of the three forms of NR6 (FIGS. 1, 2 and 3). These genomic clones, contained exons encoding from Asp50 (nucleotide 148) of the NR6 cDNAs. Sequence 5' of this in the cDNAs, including the 5'-untranslated region and the region encoding Met1 to Gln49 (SEQ ID NOs: 12, 14 and 16), and the 5' end predicted from analysis of 5' RACE products (SEQ ID NO:18) were not present in the two genomic clones isolated.

Analysis of the NR6 genomic DNA clones also provided an explanation of the three classes of NR6 cDNAs found. It is likely that NR6.1, NR6.2 and NR6.3 arise through alternative splicing of NR6 mRNA (FIG. 1). The last amino acid residue that these different NR6 proteins are predicted to share is Gln407. SEQ ID NO:18 shows that Gln407 is the last amino acid encoded by the exon that covers nucleotides g5850 to g6037 (see FIG. 2). Alternative splicing from the end of this exon (FIG. 1) accounts for the generation of cDNAs encoding NR6.1 (SEQ ID NO:12), NR6.2 (SEQ ID NO:14) and NR6.3 (SEQ ID NO:16). In the case of NR6.1, the region from g6038 to g6425 is spliced out, leading to juxtaposition of g6037 and g6426. In the case of NR6.2, the region from g6038 to 6141 is spliced out, an exon from 6142 to g6183 is retained and then this is followed by splicing out of the region from g6183 to g6425. NR6.3 appears to arise when there is no splicing from nucleotide g6038. For all three forms, a secreted rather then transmembrane form is generated, these differ however in their predicted C-terminal region. The genomic NR6 sequence with additional 5' sequence is shown in FIG. 3.

EXAMPLE 7

ESTs

Databases were searched with the murine NR6 corresponding to the unspliced version shown in SEQ ID NO:16. The murine NR6 sequence used is shown in SEQ ID NO:22.

The databases searched were:
(i) dbEST—Database of Expressed Sequence Tags National Center for Biotechnology Information National Library of Medicine, 38A, 8N8058600 Rockville Pike, Bethesda, Md. 20894Phone: 0011-1-301-496-2475 Fax: 0015-1-301-480-9241 USA.
(ii) DNA Data Bank of Japan DNA Database Release 3689. Prepared by Sanzo Miyazawa Manager/Database Administrator HidenoriHayashida Scientific Reviewer Yukiko Yamazaki/Eriko Hatada/Hiroaki Serizawa Annotators/reviewers Motono Horie/Shigeko Suzui/Yumiko SataoSecretaries/typists DNA Data Bank of Japan National Institute of Genetics Center for Genetic Information research Laboratory of Genetic Information Analyses 1111 Yata-Mishima, Shizuoka411 Japan.
(iii) EMBL Nucleic Acid Sequence Data Bank Release 47.0.
(iv) EMBL Nucleic Acid Sequence Data Bank Weekly Updates Since Release 44.
(v) Genetic Sequence Data Bank NCBI-GenBank Release 94 National Center for Biotechnology Information National Library of Medicine, 38A, 8N805 8600 Rockville Pike, Bethesda, Md. 20894 Phone: 0011-1-301-495-2475 Fax: 0015-1-301-480-9241 USA.
(vi) Cumulative Updates since NCBI-GenBank Release 88 National Center for Biotechnology Information National Library of Medicine, 38A, 8N805 8600 Rockville Pike, Bethesda, Md. 20894 USA.

The search of the databases with the murine probe identified several EST's having sequence similarity to the probe. The EST's were:
W66776 (murine sequence)
MM5839 (murine sequence)
AA014965 (murine sequence)
W46604 (human sequence)
W46603 (human sequence)
H14009 (human sequence)
N78873 (human sequence)
R87407 (human sequence).

EXAMPLE 8

Isolation of 3' cDNA Clones Encoding Human NR6

PCR products encoding human NR6 were generated using oligonucleotides UP1 and LP1 (see below) based on human ESTs (Genbank Acc:H14009, Genbank Acc:AA042914) that were identified from databases searched with murine NR6 sequence (SEQ ID NO:22). PCR was performed on a human fetal liver cDNA library (Marathon ready cDNA CLONTECH #7403-1) using Advantage Klen Taq Polymerase mix (CLONTECH #8417-1) in the buffer supplied at 94° C. fro 30s and 68° C. for 3 min for 35 cycles followed by 68° C. for 4 min and then stopping at 15° C. A standard PCR programme for the Perkin-Elmer GeneAmp PCT system 2400 thermal cycle was used. The PCR yielded a prominent product of approximately 560 base pairs (bp; SEQ ID NO:18), which was radiolabelled with [α-$^{32}$P] dCTP using a random priming method (Amersham, RPN, 1607, Mega prime kit) and used to screen a human fetal kidney 5'-STRETCH PLUS cDNA library (CLONTECH #HL1150x). Library screens were performed using Rapid Hybridisation Buffer (Amersham, RPn 1636) according to manufacturer's instructions and membranes washed at 65° C. for 30 min in 0.1×SSC/0.1% (w/v) SDS. Two independent cDNA clones were obtained as lambda phage and subsequently subcloned and sequenced. Both clones (HFK-63 and HFK-66) contained 1.4 kilobase (kb) inserts that showed sequence similarity with murine NR6. The sequence and corresponding amino acid translation of HFK-66 is shown in SEQ ID NO:24.

The translation protein sequences of clone HFK-66 shows a high degree of sequence similarity with the mouse NR6.

Oligonucleotides

FIX™II Stratagene 946203) with radiolabelled oligonucleotides, 2199 and 2200 (see below). These oligonucleotides were designed based on human ESTs (Genbank Acc: R87407, Genbank Acc:H14009) that were identified from databases searched with murine NR6. Filters were hybridised overnight at 37° C. in 6×SSC containing 2 mg/ml bovine serum albumin, 2 mg/ml Ficoll, 2 mg/ml polyvinylpyrrolidone, 100 mM ATP, 10 mg/ml tRNA, 2 mM sodium pyrophosphate, 2 mg/ml salmon sperm DNA, 0.1% (w/v) SDS and 200 mg/ml sodium azide and washed at 65° C. in 6×SSC/0.1% SDS. Five independent genomic clones were obtained and sequenced. The extend of sequence obtained has determined that the clones overlap and exhibit a similar genomic structure to murine NR6. Exon coding regions are almost identical over the region covered by the genomic clones while intron coding regions differ, although the size of the introns are comparable. The extent of known overlap is shown in FIG. 5.

Oligonucleotides

```
2199: 5' CCC ACG CTT CTC ATC GGA TTC TCC CTG 3' [SEQ ID NO:36]
2200: 5' CAG TCC ACA CTG TCC TCC ACT CGG TAG 3' [SEQ ID NO:37]
```

EXAMPLE 10

Northern Blot Analysis of Human NR6 mRNA Expression

Clontech Multiple Tissue Northern Blots (Human MTN Blot, CLONTECH #7760-1, Human Blot IV, CLONTECH #7766-I, Human Brain MTN Blot II, CLONTECH #7755-1, Human Brain MTN Blot III, CLONTECH #7750) were probed with a radiolabelled 3' human NR6 cDNA clone, HFK-66 (SEQ ID NO:24). The clone was labelled with [α-$^{32}$P] dCTP using a random priming method (Amersham, RPN 1607, Mega prime kit). Hybridisation was performed in Express Hybridisation Solution (CLONTECH H50910) for 3 hours at 67° C. and membranes were washed in 0.1×SSC/0.1% w/v SDS at 50° C.

A 1.8 kb transcript was detected in a variety of human tissues encompassing reproductive, digestive and neural tissues. High levels were observed in the heart, placenta, skeletal muscle, prostate and various areas of the brain, lower levels were observed in the testis, uterus, small intestine and colon. Photographs showing these Northern blots are available upon request. This expression pattern differs from the expression pattern observed with murine NR6.

EXAMPLE 11

```
UP1: 5'TCC AGG CAG CGG TCG GGG GAC AAC 3' [SEQ ID NO:26]
LP1: 5'TTG CTC ACA TCG TCC ACC ACC TTC 3' [SEQ ID NO:27]
```

EXAMPLE 9

Genomic Structure of Human NR6

Human genomic DNA clones encoding human NR6 was isoloated by screening a human genomic library (Lambda Mouse NR6 Expression Vectors pEF-FLAG/mNR6.1

The mature coding region of mouse NR6.1 was amplified using the PCR to introduce an in-frame Asc I restriction enzyme site at the 5' end of the mature coding region and an Mlu I site at the 3' end, using the following oligonucleotides:

```
5' oligo 5'-AGCTGGCGCGCCTCCCGGGCGGATCGGGAGCCCAC-3'   [SEQ ID NO:30]

3' oligo 5'-AGCTACGCGTTTAGAGTTTAGCCGGCAG-3'          [SEQ ID NO:31]
```

The resulting PCR derived DNA fragment was then digested with Asc I and Mlu I and cloned into the Mlu I site of pEF-FLAG. Expression of NR6 is under the control of the polypeptide chain elongation factor 1α promoter as described (16) and results in the secretion, using the IL3 signal sequence from pEF-FLAG, of N-terminal FLAG-tagged NR6 protein.

pEF-FLAG was generated by modifying the expression vector pEF-BOS as follows:

pEF-BOS (16) was digested with Xba I and a linker was synthesized that encoded the mouse IL3 signal sequence (MVLASSTTSIHTMLLLLLMLFHLGLQASIS)(SEQ ID NO: 32) and the FLAG epitope (DYKDDDDK)(SEQ ID NO: 55). Asc I and Mlu I restriction enzyme sites were also introduced as cloning sites.

The sequence of the linker is as follows:

```
          M  V  L  A  S  S  T  T  S  I  H  T  M
CTAGACTAGTGCTGACACAATGGTTCTTGCCAGCTCTACCACCAGCATCCACACCATG

TGATCACGACTGTGTTACCAAGAACGGTCGAGATGGTGGTCGTAGGTGTGGTAC

L  L  L  L  L  M  L  F  H  L  G  L  Q  A  S  I  S  AscI

CTGCTCCTGCTCCTGATGCTCTTCCACCTGGGACTCCAAGCTTCAATCTCGGCGCGCC

GACGAGGACGAGGACTAGCAGAAGGTGGACCCTGAGGTTCGAAGTTAGAGCCGCGCGG

D  Y  K  D  D  D  D  K  MluI

AGGACTACAAGGACGACGATGACAAGACGCGTGCTAGCACTAGT

TCCTGATGTTCCTGCTGCTACTGTTCTGCGCACGATCGTGATCAGATC
```

The two oligonucleotides (SEQ ID NOS: 56 and 57) were annealed together and ligated into the Xba I site of pEF-BOS to give pEF-FLAG.

pCOS1/FLAG/mNR6 & pCHO1/FLAG/mNR6

A DNA fragment containing the sequences encoding IL3 signal sequence/Flag/mNR6 and the poly(A) adenylation signal from human G-CSF cDNA, was excised from pEF-FLAG/mN6 using the restriction enzyme EcoR I. This DNA fragment was then inserted into the EcoR I cloning site of pCOS1 and pCHO1

The pCOSI and PCHO1 vectors were constructed as follows. PCHO1 is also described in reference (17) but with a different selectable marker.

PCOS1 was prepared by digesting HEF-12h-gα1 (see FIG. 24 of International Patent Publication No. WO 92/19759) with EcoRI and SmaI and ligating the digesting product iwht an EcoRI-NotI-BamHI adaptor (Takara 4510). The resulting plasmid comprises an EFIα promoter/enhancer, Nco$^r$ marker gene, SV40E, ori and an Amp$^r$ marker gene.

pCH01 was constructed by digesting DHFR-PMh-gr1 (see FIG. 25 of International Patent Publication No. WO 92/19759) with PvuI and Eco47III and ligating same with pCOSI digested with PvuI and Eco47III. The resulting vector, pCH01, comprises an EFIα promoter/enhancer, an DHFR marker gene, SV40E, Ori and a Amp$^r$ gene.

EXAMPLE 12 mRN6 has been expressed as an N' Flag tagged protein following transfection of CHO cells and as a C' Flag tagged protein following transfection of KUSA cells in both cases varying levels of dimeric and aggregated NR6 were secreted.

EXAMPLE 13

Murine NR6 Expression

NR6 expression studies were conducted in murine Northern Blots. At the level of sensitivity used in the adult mouse, NR6 expression was detected in salivary gland, lung, and testis. During embryonic development, NR6 is expressed in fetal tissues from day 10 of gestation through to birth. In cell lines, NR6 expression has been observed in the T-lymphoid line CTLL-2 as well as in FD-PyMT (FDC-P1 myeloid cells expressing polyoma midle T gene), and fibroblastoid cells including bone marrow and fetal liver stromal lines.

EXAMPLE 14

Expression, Purification and Characterisation of CHO and KUSA mNR6

The methods provide for the production of a dimeric form of CHO derived N' FLAG-mNR6 without refolding. All other methods are capable of producing NR6 and are encompassed by the present invention.

A. Production of CHO derived N' FLAG-mNR6 (dimeric form)

(i) Protein Production

To analyse structure and functional activity, a cDNA fragment containing the entire coding sequence of murine NR6 with an N-terminal FLAG (N' FLAG) sequence was cloned into the EcoR1 site of the expression vector pCHO1. For stable production of N-terminal FLAG-tagged NR6 the vector contains the DHFR (dihydrofolate reductase) gene as a selective marker with the NR6 gene under the control of an EF1 a promoter. CHO cells were transfected with the construct using a polycationic liposome transfection reagent (Lipofectamine, GibcoBRL).

(ii) Lipofectamine Transfection Method

Using six well tissue culture plates either $2\times10^5$ KUSA cells in 2 ml IMDM+10% (v/v) FCS or $2\times10^5$ CHO cells were cultured in 2 ml α-MEM+10% (v/v) FCS until 70% confluent. 2 μg DNA diluted in 100 μl OPTI-MEM I (Gibco BRL, USA) was mixed gently with 12 μl lipofectamine diluted in 100 μg OPTI-MEM I and incubated at room temperature for 30 min to allow DNA complex formation. DNA complexes were gently diluted in a total volume of 1 ml of OPTI-MEM I and overlaid onto washed KUSA or CHO call monolayers. A further 1 ml IMDM+20% (v/v) FCS (KUSA cells) or 1 ml α-MEM+20% (v/v) FCS (CHO cells) was added to transfected cells after 5 hours. At 24 hours, the culture medium was replaced with fresh complete growth medium. At 48 hours after transfection, selection was applied. A methotrexate resistant clone secreting comparatively high levels of NR6 was selected and expanded for further analysis.

(iii) Protein Expression

CHO cells were grown to confluence in roller bottles in nucleoside free α-MEM+10% (v/v) FCS. Selection was maintained by using 100 ng/ml Methotrexate in the conditioned media according to manufacturer instructions. Expression was monitored by Biosensor and harvesting found to be optimal at 3 to 4 days.

B. Protein Analysis (i) Biosensor Analysis

Expression and purification was monitored by Biosensor analysis (BiaCoreTM, Sweden) where anti FLAG peptide M2 antibody (Kodak Eastman, USA), specific for the FLAG peptide sequence was bound to the sensorchip. Fractions were analysed for binding to the sensor surface (resonance units) and the sample then removed from the surface using 50 mM Diethylamine pH 12.0 prior to analysis of the next fraction. Immobilisation and running conditions of the Biosensor follow the manufacturer's instructions.

(ii) Protein Production

In order to generate and characterise NR6, conditioned media (2 L) produced by CHO cells was harvested after day 3, post confluence. Conditioned media was concentrated using diafiltration with a 10,000 molecular weight cut-off. (Easy flow, Sartorius, Aus). At a volume of 200 ml (i.e. 10× concentrated) the sample was buffer exchanged into 20 mM Tris, 0.15M NaCl, 0.02% (v/v) Tween 20 pH 7.5 (Buffer A).

(iii) Immunoprecipitation and Western Blot analysis of mNR6

Concentrated conditioned media (1 ml) was immunoprecipitated with M2 affinity resin (20 μg, Kodak Eastman). To examine the structural characterisation of mNR6 SDS PAGE was performed under reducing and non-reducing conditions. Separation was performed on NOVEX 4–20% (v/v) Tris/glycine gradient gels and protein transfered on PVDF membrane. Western blots were probed with biotinylated M2 antibody (primary, 1:500) and then streptavidin peroxidase (secondary, 1:3000). Samples were visualised by autoradiography using electrochemiluminescence (ECL, Dupont, USA).

By regressional analysis of prestained standards (BIO-RAD, Aus.) the molecular weight of the monomeric unit was calculated to be 65,000 daltons. Under non-reducing conditions the molecular weight was calculated to be 127,000 indicating that NR6 is a disulphide linked dimer. A tetrameric complex running at approximately 250,000 daltons was also observed. Although a band running at approximately 50,000 daltons was observed, no monomeric NR6 was detected under non-reducing conditions indicating that the majority of NR6 expressed in this system is disulphide linked.

(iv) Affinity Chromatography of mNR6

Concentrated conditioned media (200 ml) was applied to M2 affinity resin (5 ml) under gravity. To enhance recovery the unbound fraction was reapplied to the column four times prior to extensive washing of the column with 200 volumes of Buffer A. Biosensor analysis indicates that approximately 20% of the M2 binding originally present in the concentrate remains in the unbound fraction. The bound fraction was eluted from the column using an immunodesorbant (50 ml); actisep (Sterogene Labs, USA).

(v) Ion Exchange and Desalting of mNR6

In order to buffer exchange mNR6 prior to anion chromatography, 10 ml batches of the eluted fraction (50 ml) were applied to an XK column (400×26 mm I.D.) containing G25 sepharose (Pharmacia, Sweden). Chromatography was developed at 4 ml/min using an FPLC (Pharmacia, Sweden) equipped with an online UV280 and conductivity monitor. The mobile phase was 10 mM Tris, 0.1M NaCl, 0.02% v/v Tween, pH 8.0. 10 ml fractions were collected between 12.5 min and 25 min to optimist recovery and removal of salt. Fractions were analysed by Biosensor analysis and pooled according to binding. All pooled active fractions were diluted with an equal volume of 20 mM Tris, 0.02% (v/v) Tween, pH 8.5 (Buffer B) and then loaded onto a Mono Q 5/5 (Pharmacia, Sweden) at a flow rate of 2 ml/min. The column was washed with buffer B. Elution was performed using a linear gradient between buffer B and buffer B containing 0.6M NaCl over 30 min at a flow rate of 1 ml/min. Fractions (1 minute) were collected and analysed on the Biosensor and also by SDS PAGE and Western blot analysis. Fractions 15 to 26 (approximately 0.4M NaCl) appear to contain the majority of mNR6 as indicated by the Biosensor.

C. Production of CHO Derived N' FLAG-mNR6 (monomeric form)

(i) Protein Production

A cDNA fragment containing the entire coding sequence of murine NR6 with an N-terminal FLAG™ sequence was cloned into the expression vector pCHO1 for production of N-terminal FLAG-tagged protein. This vector contains a neomycin resistance gene with expression of the NR6 gene under the control of an EF1α promoter. This expression construct was transfected into CHO cells using Lipofectamine (Gibco BRL, USA) according to the manufacturer instructions. Transfected cells were cultured in IMDM+10% (v/v) FCS with resistant cells selected in geneticin (600 μg/ml, Gibco BRL, USA). A neomycin resistant clone, secreting comparatively high levels of NR6 was selected and expanded for further analysis.

(ii) Protein Expression

N' FLAG-NR6 expressed in serum free conditioned media (10 liter) was harvested from transfected CHO and cells. Collected media was concentrated using a CH2 ultrafiltration system equipped with a S1Y10 cartridge (Amicion molecular weight cut-off 10,000). Preliminary examination of the expressed product under reducing and non-reducing SDS PAGE followed by western blot analysis was performed. Visualisation of the protein on Westerns was specific to the primary antibody anti FLAG M2. Under reducing conditions a band approximately at 65,000 daltons was observed. Under non-reducing conditions, dimer and larger molecular weight aggregates were observed. These are disulphide linked monomers as they are not present in the reducing gel. Small amounts of monomer appear to be present in non-reducing gels.

(iii) Affinity Chromatography of NR6

Concentrated conditioned media was applied to an anti FLAG M2 affinity resin (100×16 mm I.D.). After washing the unbound proteins off the column, the bound proteins were eluted using FLAG peptide (60 µg/ml) in PBS.

(iv) Ion Exchange Chromatography of NR6

Eluted fractions from affinity column were dialysed overnight against 20 mM Tris-HCl pH 8.5 (buffer C) containing 50 mM Dithiothretol (DTT) using 25,000 cut-off dialysis tubing (Spectra/Por7, Spectrum). The dialysed fractions were loaded onto Mono Q 5/5 (Pharmacia, Sweden) previously equilibrated with buffer C containing 5 mM DTT. Chromatography was developed using a linear gradient between buffer C and buffer C containing 1.0 M NaCl at a flow rate of 0.5 ml/min.

(v) Refolding of NR6

Fractions containing NR6 from the Mono Q were adjusted to 50 mM DTT and left overnight at 4° C. To initiated refolding the sample was then dialysed against 50 mM Tris-HCl (pH 8.5), 2 M Urea, 0.1% (v/v) Tween 20, 10 mM Glutathione (reduced) and 2 mM Glutathione (oxidised) at a final protein concentration of 100 µg/ml. Folding was carried out at ambient temperature with one change of the buffer over 24 hours.

(v) Reversed Phase High Performance Liquid Chromatography (RP-HPLC)

The folded product was further purified by RP-HPLC using a Vydac C4 resin (250×4.6 mm I.D.) previously equilibrated with 0.1% (v/v) Trifluoroacetic acid (TFA). Elution was carried out using a linear gradient from 0 to 80% (v/v) acetonitrile/0.1% (v/v) TFA at a flow rate of 1 ml per minute.

D. pCHO1/NR6/FLAG

In order to determine the native N termini of NR6, a C terminal FLAG NR6 CHO cell line was established.

The plasmid pKUSA166 (murine NR6 cDNA cloned into the EcoR I site of pBLUESCRIPT) was digested with BamHI to remove the sequences encoding the last 15 amino acids of murine NR6. Synthetic oligonucleotides which encode the 3' end of mouse NR6 followed by the FLAG peptide tag were annealed and ligated into the BamH I site of pKUSA166. The sequence of the oligonucleotides was as follows:

(i) Production of Polyclonal NR6 Antiserum

The following peptide from the N terminal area of NR6 was chosen for production of polyclonal antiserum to NR6

VISPQDPTLLIGSSLQATCSIHGDTP [SEQ ID NO:39]

The peptide was conjugated to KLH and injected into rabbits. Production and purification of the polyclonal antibody specific to the NR6 peptide sequence follows standard methods.

(ii) Protein Expression

KUSA cells transfected with cDNA of C terminal tagged mNR6 were grown to confluence in flasks (800 ml) using IMDM media containing 10% (v/v) FBS. Conditioned media (100 ml) was harvested 3–4 days post confluence.

(iii) Characterisation of NR6 by Immunoprecipitation and Western Blotting

In order to establish that NR6 with the predicted sequence is produced in KUSA cells transfected with the cDNA, western blot analysis using both M2 antibody and purified NR6 specific rabbit antibody were performed. Conditioned media (1 to 5 ml) was immunoprecipitated with M2 affinity resin (10–20 µl). Then after sufficient time for binding, the beads were washed with MT-PBS and subsequently NR6 eluted with 100 µg/ml FLAG peptide (40 µl (1, 5 minute incubation). The sample was then subjected to reducing and non reducing SDS PAGE followed by western blot analysis. Both purified NR6 polyclonal antibody (purified by protein G) and M2 antibody recognise a band under reducing conditions of a molecular weight size approximately 65,000 daltons. Since the two antibodies reconising resides at the N terminus and C terminus it is reasonable to assume that full length NR6 is produced. Biotinylation of the respective antibodies by standard methods reduces the background. Under non-reducing conditions polyclonal NR6 bind antibodies to a band of a molecular weight of approximately 127,000, consistent with a dimeric NR6 disulphide linked form. Minor components of tetrameric NR6 are present, no monomeric NR6 is evident using polyclonal NR6 antibodies.

EXAMPLE 15

Generation of NR6 Knockout Mice

```
I L P S G R R G A A R G P A G D Y K D D D K *          [SEQ ID NO:34]

GATCTTGCCCTCGGGCAGACGGGGTGCGGCGAGAGGTCCTGCCGGCGACT   [SEQ ID NO:33]

ACAAGGACGACGATGACAAGTA G

AACGGGAGCCCGTCTGCCCCACGCCGCTCTCCAGGACGGCCGCTGATGTT  [SEQ ID NO:35]

CCTGCTGCTACTGTTCATCCTAG
```

The 5' end of the linker introduces a silent mutation (CTG>TTG), to destroy the 5' BamH I site upon insertion of the linker. The NR6 cDNA (with native signal sequence) with the C-terminal FLAG was cut out of pKUSA166 with EcoR I and BamH I and cloned into the EcoR I—BamH I cloning sites of pCHO-1. This vector results in the secretion of NR6 protein with a C-terminal flag tag (C' FLAG-mRN6).

This vector results in the secretion of NR6 protein from KUSA cells. The vector pCHO1 has been previously described in (17) although with a different secretable marker.

To construct the NR6 targeting vector, 4.1 kb of genomic NR6 DNA containing exons 2 through to 6 was deleted and replaced with G418-resistance cassette, leaving 5' and 3' NR6 arms of 2.9 and 4.5 kb respectively. A 4.5 kb XhoI fragment of the murine genomic NR6 clone 2.2 (FIG. 3) containing exons 7, 8 and 3' flanking sequence was subcloned into the XhoI site of pBluescript generating pBSNR6Xho4.5. A 2.9 kb NotI-StuI fragment within NR6 intron 1 from the same genomic clone was inserted into NotI and EcoRV digested pBSNR6Xho4.5 creating pNR6-Ex2-6. This plasmid was digested with ClaI, which was situated between the two NR6 fragments, and following blunt ending, ligated with a blunted 6 kb HindIII fragment from placZneo, which contains the lacZgene and a PGKneo cassette, to generate the Fox targeting vector, pNR61acZneo. pNR61acZneo was linearised with NotI and electroporated into W9.5 embryonic stem cells. After 48 hours, transfected cells were selected in 175 µg/ml G418 and resistant clones picked and expanded after a further 8 days.

Clones in which the targetting vector had recombined with the endogenous NR6 gene were identified by hybridising SpeI-digested genomic DNA with a 0.6 kb XhoI-StuI fragment from genomic NR6 clone 2.2. This probe (probe A, FIG. 4), which is located 3' to the NR6 sequences in the targeting vector, distinguished between the endogenous (9.9 kb) and targeted (7.1 kb) NR6 loci (FIG. 5).

Genomic DNA was digested with SpeI for 16 hrs at 37° C., electrophoresed through 0.8% (w/v) agarose, transferred to nylon membranes and hybridised to $^{32}$P-labelled probe in a solution containing 0.5M sodium phosphate, 7% (w/v) SDS, 1 mM EDTA and washed in a solution containing 40 mM sodium posphate, 1% (w/v) SDS at 65° C. Hybridising bands were visualised by autoradiography for 16 hours at −70° C. using Kodak XAR-5 film and intensifying screens. Two targeted ES cell clones, W9.5NR6-2-44 and W9.5NR6-4-2, were injected into C57Bl/6 blastocysts to generate chimeric mice. Male chimeras were mated with C57Bl/6 females to yield NR6 heterozygotes which were subsequently interbred to produce wild-type (NR6$^{+/+}$), heterozygous (NR6$^{+/-}$) and mutant (NR6$^{-/-}$) mice. The genotypes of offspring were determined by Southern Blot analysis of genomic DNA extracted from tail biopsies.

Genotyping of mice at weaning from matings between NR$^{+/-}$ heterozygous mice derived from both targated ES cell clones revealed an absence of homozygous NR6$^{-/-}$ mutants. As no unusual loss of mice was observed between birth and weaning, this suggest that lack of NR6 is lethal during embryonic development or immediately after birth. Genotyping of embryonic tissues at various stages of development suggests that death occurs late in gestation (beyond day 16) or at birth.

EXAMPLE 16

Oligonucleotides

1943:

5' GTC CAA GTG CGT TGT AAC CCA 3'    [SEQ ID NO:40]

2070:

5' GCT GAG TGT GCG CTG GGT CTC    [SEQ ID NO:41]
ACC 3'

2057:

5' GGC TCC ACT CGC TCC AGA 3'    [SEQ ID NO:42]

EXAMPLE 17

Isolation of a Full-length Human NR6 cDNA Clones

PCR Amplification of a huNR6 Specific Probe:

Two human ESTs (Genbank Acc: AA042914 and H14009) showing homology with murine NR6 were used to design oligonucleotides for PCR screening of arange of commercially available human genomic and cDNA libraries. Oligonucleotide sequence:

Fwd prime: 5'-TGC CCC CAG AGA AAC CCG TCAAC-3' [SEQ ID NO:45] and

Rev primer: 5'-CGT GAG TAC ATC GGA GCG GGC AGA G-3' [SEQ ID NO:46].

The expected fragment size of 300 bp was amplified (25 cycles, 96oCdenaturation, 60° C. annealing and 72° C. extension, Stratagene Pfu DNA polymerase Cat#600159, Corbett PC-960G) from a human placental cDNA library (Clontech Human Placenta 5'-STRETCH PLUS cDNA library Cat#HL3007b, cloning vector 1gt11, oligo(dT) and random primed, source RNA25 year old Caucasian mother). PCR amplification was repeated using aproof reading polymerase (Stratagene) to generate blunt ended PCR products for cloning into pCR-Blunt vector (Invitrogen ZeroBlunt PCRCloning Kit, Cat# 440302). PCR colony analysis was used to identify transformed E. coli containing appropriately ligated vector and the identity of the inserts confirmed by sequencing.

Screening of Human Placental Library:

The huNR6 probe was excised from pCR-Blunt using EcoRI, 3' end labelled with 32P (Pharmacia Biotech Ready To Go DNA Labelling Beads Cat #27-9240-01) and used to screen the placental cDNA library (standard methods, duplicate filters, 106 plaques screened, high stringency washes—0.2×SSC, 0.1% SDS, 65° C.). Twenty positives were identified on pry screening and following two rounds of plaque purification, eighteen cloned tertiary phage stocks containing inserts ranging from ~1–3 kb in size remained. Phage clone #11 was selected for thorough sequencing and found to contain 2079 bp insert, with an ORF of 1260 bases, 515 bp of 5'UTR and 304 bp of 3'UTR. The sequence of the ORF and the corresponding amino acid translation showed a high degree of homology to the corresponding mouse NR6 cDNA and amino acid sequences (88% and 95% respectively, FIGS. 6 and 7).

EXAMPLE 18

Human NR6 Expression Vectors pEF-N'-FLAG/hNR6

The coding region of the mature human NR6 protein was amplified using PCR to introduce in frame Asc I resummon enzyme sites at the 5' and 3' ends using the following oligonucleotides:

5'Oligo 5'-TCAGGCGCGCCTTGCCCACACAGCTGT-GATC-3' [SEQ D NO:47]

3' Oligo 5'-TCAGGGCGCGCCTTATCTGGCAGGAC-CTCT-3' [SEQ ID NO:48]

The resulting PCR derived DNA fragment was then digested with Asc I and cloned into the Mlu X site of pEF-FLAG-S. Expression of NR6 is under control of the polypeptide elongation factor 1a promoter and results in the secretion, using the IL3 signal sequence from pEF-FLAG, of N-terminal FLAG-tagged NR6 protein.

pEF-C'-FLAG/hNR6

The complete coding region, including the endogenous signal sequence, of human NR6 protein was amplified using PCR to introduce in frame Asc I restriction enzyme sites at the 5' and 3' ends using the following oligonucleotides:

5'Oligo 5'-TCAGGCGCGCCTGCCCGCCGGCCGC-3' [SEQ ID NO:49]

3'Oligo 5'-ATAAGGCGCGCCCTGGCAGGACCTCTCG-3' [SEQ ID NO:50]

The resulting PCR derived DNA fragment was then digested with Asc I and cloned into the Asc I site of pEF-FLAG-I. Expression of NR6 is under control of the polypeptide elongation factor 1a promoter and results in the secretion, using the endogenous NR6 signal sequence, of C-terminal FLAG-tagged NR6 protein.

pEF-N'-I-SPY/hNR6

The coding region of the mature human NR6 protein was amplified using PCR to introduce in frame Asc I restriction enzyme sites at the 5' and 3' ends using the following oligonucleotides:

5'Oligo 5'-TCAGGCGCGCCTTGCCCACACAGCTGTGATC-3' [SEQ ID NO:51]

3'Oligo 5'-TCAGGGCGCGCCTTATCTGGCAGGACCTCT-3' [SEQ ID NO:52]

The resulting PCR derived DNA fragment was then digested with Asc I and cloned into the Mlu I site of pEF-I-SPY-S. In this vector the region encoding the FLAG tag has been excised from pEF-FLAG-S and replaced with sequence encoding an I-SPY epitope tag (QYPALT, AMRAD Biotech, Australia). Expression of NR6 is under control of the polypeptide elongation factor 1a promoter and results in the secretion, using the IL3 signal sequence from pEF-FLAG, of N-terminal FLAG-tagged NR6 protein.

pEF-C'-I-SPY/hNR6

The complete coding region, including the endogenous signal sequence, of human NR6 protein was amplified using PCR to introduce in frame Asc I restriction enzyme sites at the 5' and 3' ends using the following oligonucleotides:

5'Oligo 5'-TCAGGCGCGCCTGCCCGCCGGCCGC-3' [SEQ ID NO:53]

3'Oligo 5'-ATAAGGCGCGCCCTGGCAGGACCTCTCG-3' [SEQ ID NO:54]

The resulting PCR derived DNA fragment was then digested with Asc I and cloned into the Asc I site of pEF-I-SPY-I (see above for details). Expression of NR6 is under control of the polypeptide elongation factor 1a promoter and results in the secretion, using the endogenous NR6 signal sequence, of C-terminal FLAG-tagged NR6 protein.

EXAMPLE 19

Expression, Purification and Characterisation of CHO Human NR6

A. Transient Expression and Analysis of NR6

Transient Expression of C'-terminal FLAG-tagged Human NR6

For transient expression of human NR6 the pEF-C'-FLAG/hNR6 expression construct described above was transfected into 293T cells using Lipofectamine (Gibco BRL, USA) according to the manufacturers instructions. Briefly, cells grown to approximately 70–80% confluence in 75 cm2 tissue culture flasks were washed in serum free DMEM media then exposed to a mixture of pEF-C'-FLAG/hNR6 and Lipofectine diluted in DMEM. After 5 hours at 37° C. with 5% CO2 the cells were washed once with DMEM and incubated for a further 16 hours in DMEM supplemented with 10% v/v FCS, glutamine and antibiotics (DM10). At this time the DM10 was removed and replaced with a further 10 ml/flask of fresh DM10 and transfected cells incubated for a further 48 hours.

Figure 8A:
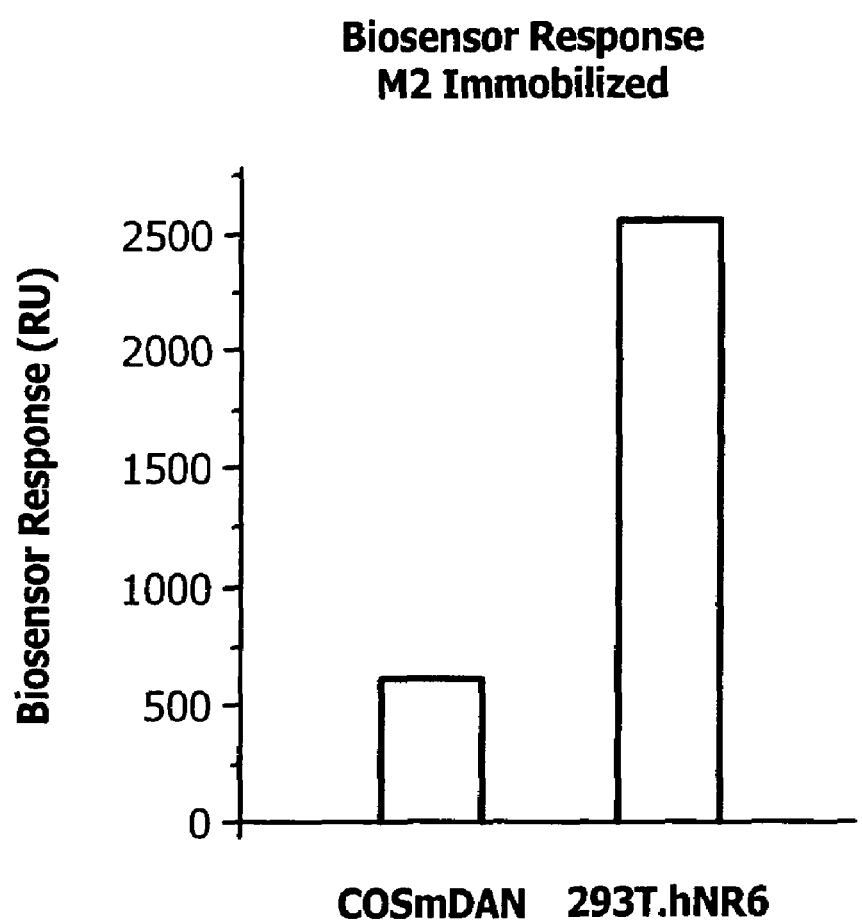

Supernatants containing secreted human NR6 were recovered, centrifuged and filtered to remove cell debri, then stored at 4° C. Expression and purification was monitored by Biosensor analysis (BiaCore TM, Sweden) where anti-FLAG peptide monoclonal antibody (M2, Kodak Eastman, USA) was bound to the sensorchip. Where multiple fractions were analysed for binding to the sensor surface (resonance units) the chip was desorbed with 50 mM Diethylamine pH 12.0 prior to application of the next sample. Biosensor analysis indicated that the transfected 293T cells secreted significant quantities of FLAG-tagged human NR6 protein into the surrounding media (FIG. 8A). The conditioned media (5 ml) was applied to M2 affinity resin (1 ml) under gravity. To enhance recovery the unbound fraction was reapplied to the column 4 times prior to extensive washing of the column with 200 volumes of Buffer A (see Example 14).

Figure 8B:
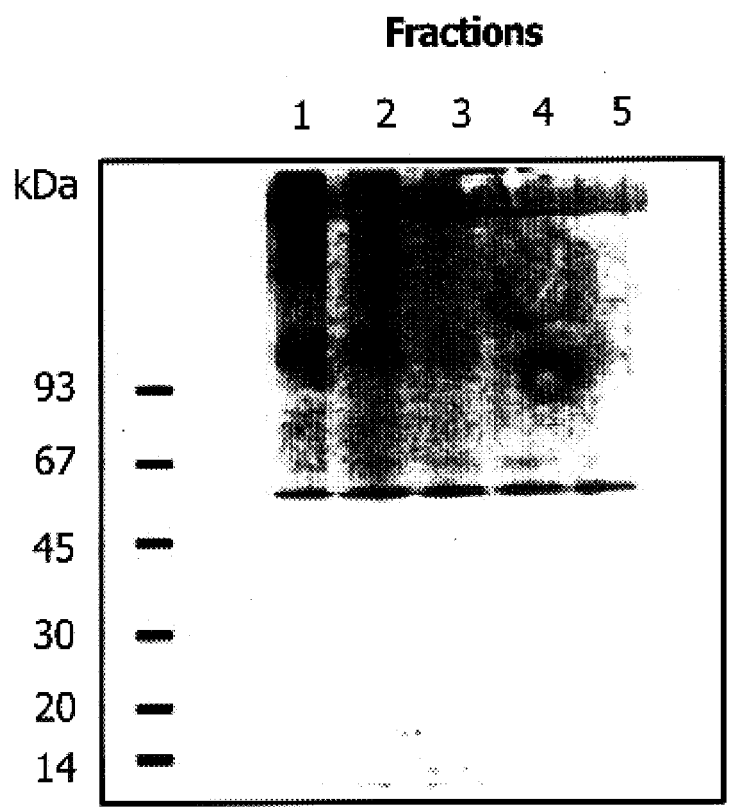
Figure 8C:
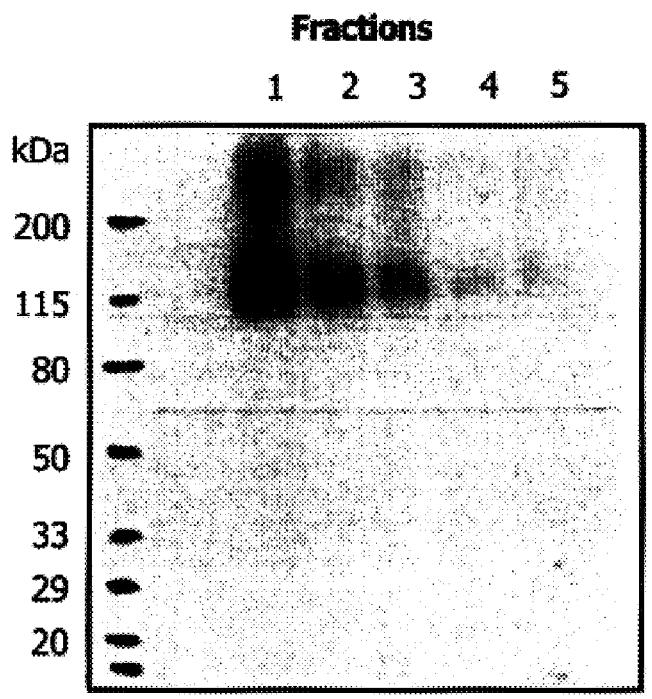

The bound fraction was eluted from the column with 10×1 ml volumes of 100 mg/ml FLAG peptide (Kodak Eastman) in Tris-buffered saline. The first 5 fractions were electrophoresed on an SDS-PAGE gel under non-reducing conditions. Silver staining revealed a band of the expected size for dimeric NR6 at approximately 120 kDa in fractions 1–3 (FIG. 8B). To confirm that this band was indeed NR6, an identical gel was subjected to Western blot analysis using the M2 monoclonal antibody. Fractions were electrophoresed under non-reducing conditions, transferred to a PVDF membrane then probed with a biotinylated M2 antibody. Bound antibody was detected using a Streptavidin-HRPO conjugate and ECL substrate. Subsequent autoradiography indicated a band of the expected size for dimeric NR6 at approximately 120 kDa (FIG. 8C).

N-terminal Amino Acid Sequence of C-terminal FLAG-tagged NR6

For determination of the N-terminal amino acid sequence, C-terminal FLAG-tagged NR6 was purified from 75 ml of transfected 293T cell supernatant by M2 affinity chromatography as described above. Peak fractions (as determined by SDS-PAGE) were concentrated by lyophillization, resuspended in 0.5 ml and applied to a Superose 12 size exclusion column (Pharmacia, Flow rate 0.5 ml/min, 1 min fractions in 1% w/v ammonium bicarbonate, pH7.8). Peak fractions containing NR6, as determined by Biosensor and SDS-PAGE analysis, were subjected to N-terminal sequence analysis using a Hewlett Packard sequencer with the indicated N-terminus at Ala40. This is identical to the N-terminus of mature CHO cell derived murine NR6.

NR6 is Secreted as a Homodimer

Western blot analysis following non-reducing and reducing SDS-PAGE and N'-terminal sequence analysis indicated that the secreted form of NR6 was as a homodimer rather than a heterodimer. To further confirm secretion of homodimeric NR6, 293 T cells were transiently cotransfected (Lipofectamine, as above) with vectors encoding C'-terminal FLAG-tagged NR6 and C'-terminal I-SPY-tagged NR6. For control purposes 293T cells were also transfected with each vector alone.

Supernatants from each transfection were immunoprecipitated with resin coupled—monoclonal antibody specific for either I-SPY or FLAG epitopes. The precipitates were then electrophoresed on SDS-PAGE, transferred to PVDF and probed with anti-FLAG antibody according to the standard protocol FLAG specific reactivity of the appropriate molecular weight was detected in appropriate controls and in supernatants from cotransfections following precipitation with both anti-FLAG and anti-I-SPY coupled resins (results not shown). This indicates that FLAG-tagged and I-SPY tagged monomers are associating to form homodimers.

B. Production of Stable Cell Lines Secreting Dimeric Human NR6

For the generation of stable cell lines expressing human NR6, CHO cells and 293T cells were cotransfected with the pEF-C'-FLAG/hNR6 or pEF-N'-FLAG/hNR6 expression constructs and a vector incorporating a gene encoding puromycin resistance using Lipofectamine (Gibco BRL, USA) according to the manufacturers instructions. Following selection in puromycin (25 mg/ml, Sigma) resistant cells were cloned in 96 well microtitre plates by limiting dilution and clones assayed for NR6 production by a combination of Dot-blot analysis and Biosensor analysis (as above). For Dot-blot analysis 50 ml of supernatant from each clone was transferred to nitrocellulose membrane using a Dot-blot apparatus (BioRad, USA). The nitrocellulose was then incubated in blocking buffer (Phosphate buffered saline, PBS+ 1% Casein) for 30 min, washed in PBS and then probed with anti-FLAG M2 antibody (1:1000 in blocking buffer, 60 min), washed again and bound M2 detected using a HRPO conjugated anti-mouse antibody (Silenus, 1:2000 in blocking buffer, 60 in) used in conjunction with TMB substrate (Boehringer Mannheim). Following Dot-blot and Biosensor analysis 6 CHO cell clones expressing C-terminal FLAG-tagged human NR6, 6 CHO cell clones expressing N-terminal FLAG-tagged human NR6, and 6 293T cell clones expressing C-terminal FLAG-tagged human NR6 were selected and expanded for further analysis. Following further analysis a single clone was selected from each group of 6 for expansion and production of human NR6 for subsequent biological analysis. Biosensor analysis of supernatant from each of these clones indicated relatively high level production of NR6 (FIG. 9) and Western blot analysis confirmed that the dominant form of FLAG-tagged protein was a dimer of molecular weight approx. 120 kDa (FIG. 9).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Du, X. X. and Williams, D. A. (1994) *Blood* 83: 2023–2030.
2. Yang, Y. C. and Yin, T. (1992) *Biofactors* 4: 15–21.
3. Paul, S. R, Bennett, F., Calvetti, J. A., Kelleher, K., Wood, C. R., O'Hara, R. J. J., Leary, A. C., Sibley, B., Clark, S. C., Williams, D. A and Yang, Y.-C. (1990) *Proc. Natl. Acad. Sci. USA* 87: 7512.
4. Musashi, M., Clark, S. C., Sudo, T., Urdal, D. L., and Ogawa, M. (1991) *Blood* 78: 1448–1451.
5. Schibler, K. R., Yang, Y. C. and Christensen, R. D. (1992) *Blood* 80: 900–3.
6. Tsuji, K, Lyman, S. D., Sudo, T., Clark, S. C., and Ogawa, M. (1992) *Blood* 79: 2855–60.
7. Burstein, S. A., Mei, R. L., Henthorn, J., Friese, P. and turner, K (1992) *J. Cell. Physiol.* 153: 305–12.
8. Hangoc, G., Yin, T., Cooper, S., Schendel, P., Yang, Y. C. and Broxmeyer, H. E. (1993) *Blood* 81: 965–72.
9. Teramura, M., Kobayashi S., Hoshino, S., Oshimi, K. and Mizoguchi, H. (1992) *Blood* 79: 327–31.
10. Yonemura, Y., Kawakita, N, Masuda, T., Fujimoto, K, Kato, K. and Takatsuki, K. (1992) *Exp. Hematol.* 20: 1011–6.
11. Baumann, H. and Schendel, P. (1991) *J. Biol. Chem.* 266. 20424–7.
12. Kawashima, L, Ohsumi, J., Mita-Honjo, K., Shimoda-Takano, K, Ishikawa, H., Sakakibara, S., Miyadai, K and Takiguchi, Y. (1991) *Febs. Lett.* 283: 199–202.
13. Keller, D. C., Du, X. X., Srour, E. f., Hoffman, R. and Williams, D. A. (1993) *Blood* 82: 1428–35.
14. Sambrook et al (1989) Cloning: A Laboratory Manual. Cold Spring Harbour Laboratory, Cold Spring Harbour, N.Y.
15. Chirgwin et al (1979) *Biochemistry* 18: 5294–5299.
16. Mizushima and Nagata (1990) *Nucl. Acids Res.*, 12: 5322.
17. *FEBS Lett* (1994) 356: 244–248.
18. Bazan, J. F. (1990) *Proc Natl Acad Sci USA*, 87, 6934–8
19. de Vos, A. M., Ultsch, M. and Kossiakoff, A. A. (1992) *Science*, 255, 306–12
20. Layton, M. J., Cross, B. A., Metcalf, D., Ward, L. D., Simpson, R. J. and Nicola, N. A. (1992) *Proceedings of the National Academy of Sciences of the United States of America* 89: 8616–8620
21. Taga, T., Hibi, M., Hirata, T., Tamasaki, K, Tasukawa, K, Matsuda, T., Hirano, T. and Kishimoto, T. (1989) *Cell* 58: 573–581
22. Merberg, D. M., Wolf, S. F. and Clark, S. C. (1992) Sequence similarity between NKSF and the IL6/G-CSF family (1992) *Immunology Today* 13: 77–78
23. Cearing, D. P. and Cosman, D. (1991) *Cell* 66:9–10
24. Wrighton, N. C., Farrell, F. X., Chang, R., Kashyap, A. W, Barbone, F. P., Mulcahy, L. S., Johnson, D. L., Barrett, R. W., Jolliffe, L. K. and Dower, W. J. (1996) *Science* 273: 458–464.
25. Cwirla, S. E., Balasubramanian, P., Duffin, D. J., Wagstrom, C. R., Gates, C. M., Singer, S. C., Davis, A. M., Tansik, R. L, Mattheakis, L. C., Boytos, C. M., Schatz, P. J., Baccanari, D. P., Wrighton, N. C., Barret, R. W. and Dower, W. J. (1997) *Science* 276: 1696–9, 1997
26. Samuel Davis et al (1996) *Cell* 87:1161–1169.
27. Chitra Suri et al (1996) *Cell* 87: 1171–1180.
28. Nicholas C. Wrighton et al (1996) *Science* 273: 458–463.
29. Oded Livnah et al (1996) *Science* 273: 464–471.
30. Cwirla, Steven E. et al (1997) *Science* 276: 1696–1699.

The invention claimed is:

1. An isolated haemopoietin receptor comprising an amino acid sequence encoded by a nucleic acid molecule which hybridizes under high stringency conditions to the full complement of the nucleotide sequence set forth in any one of SEQ ID NO: 12, 14, 18 and 28 wherein said high stringency conditions comprise from at least about 31% v/v to at least about 50% v/v formamide for hybridisation, and 0.1×SSC/0.1% (w/v) SDS at 65° C. for 30 min for washing conditions, and wherein said receptor comprises the amino acid motif:

Trp Ser Xaa Trp Ser (SEQ ID NO:1)

wherein Xaa is any amino acid.

2. The isolated haemopoietin receptor according to claim 1, wherein Xaa is Asp or Glu.

3. An isolated haemopoietin receptor comprising the amino acid sequence set forth in SEQ ID NO:13.

4. An isolated haemopoietin receptor comprising the amino acid sequence set forth in SEQ ID NO:15.

5. An isolated haemopoietin receptor comprising an amino acid sequence encoded by a nucleic acid molecule which hybridises under high stringency conditions to the full complement of the nucleotide sequence set forth in SEQ ID NO:24, wherein said high stringency conditions comprise from at least about 31% v/v to at least about 50% v/v formamide for hybridisation, and 0.1×SSC/0.1% (w/v) SDS at 65° C. for 30 min for washing, and wherein said receptor further comprises the amino acid motif:

Trp Ser Xaa Trp Ser (SEQ ID NO:1)

wherein Xaa is any amino acid.

6. An isolated haemopoietin receptor comprising the amino acid sequence set forth in SEQ ID NO:44.

7. An isolated haemopoietin receptor comprising an amino acid sequence encoded by a nucleic acid molecule which hybridises under high stringency conditions to the full complement of the nucleotide sequence coding for a polypeptide as set forth in SEQ ID NO:44, wherein said high stringency conditions comprise from at least about 31% v/v to at least about 50% v/v formamide for hybridisation, and 0.1×SSC/0.1% (w/v) SDS at 65° C. for 30 min for washing, and wherein said receptor further comprises the amino acid motif:

Trp Ser Xaa Trp Ser (SEQ ID NO:1)

wherein Xaa is any amino acid.

* * * * *